US006066778A

United States Patent [19]
Ginsburg et al.

[11] Patent Number: 6,066,778
[45] Date of Patent: May 23, 2000

[54] TRANSGENIC MICE EXPRESSING APC RESISTANT FACTOR V

[75] Inventors: David Ginsburg, Ann Arbor, Mich.; Jisong Cui, South Plains, N.J.

[73] Assignee: The Regents of the University of Michigan, Ann Arbor, Mich.

[21] Appl. No.: 08/746,111

[22] Filed: Nov. 6, 1996

[51] Int. Cl.[7] .............................. C12N 5/00; A61K 49/00
[52] U.S. Cl. ................. 800/2; 800/DIG. 1; 800/DIG. 4; 424/9.2; 435/172.3
[58] Field of Search .................. 424/9.1, 9.2; 435/172.3; 800/2, DIG. 1–4

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,873,191 | 10/1989 | Wagner et al. | 435/172.3 |
| 4,959,317 | 9/1990 | Sauer | 435/172.3 |
| 4,965,188 | 10/1990 | Mullis et al. | 435/6 |
| 5,545,808 | 8/1996 | Hew et al. | 800/2 |

FOREIGN PATENT DOCUMENTS

| | | |
|---|---|---|
| WO 86/06745 | 11/1986 | WIPO . |
| WO 90/08832 | 8/1990 | WIPO . |

OTHER PUBLICATIONS

Yang et al. cDNA cloning and functional analysis of recombinant murine factor V. Blood vol. 86, No. 10, Suppl. 1, p. 280, Nov. 15, 1995.

Fassler et al. Knockout mice—how to make them and why—the immunological approach. Int. Arch. of Allergy and Immun. vol. 106, No. 4, pp. 323–334, Apr. 1995.

Houdebine, L. M. Production of pharmaceutical proteins from transgenic animals. J. of Biotech. vol. 34, pp. 269–287, 1994.

Salter et al. Transgenic chickens: insertion of retroviral genes into the chicken germ line. Virol. vol. 157, pp. 236–240, 1987.

Pursel et al. Genetic engineering of livestock. Science, vol. 244, pp. 1281–1288, Jun. 16, 1989.

Bradley et al. Modifying the mouse: design and desire. Biotechnology, vol. 10, pp. 534–539, 1992.

Goodman and Gilman's *The Pharmacological Basis of Therapeutics* (1990) 8th ed., Pergamon Press, New York, pp. 1311–1331.

AHFS Drug Information (1995) Gerald K. McKevoy, ed., pp. 931–937.

AHFS Drug Information (1995) Gerald K. McKevoy, ed., pp. 924–929.

Barbanti et al. (1993) "Therapeutic Effect of Low Molecular Weight Dermatan Sulphate (Desmin 370) in Rat Venous Thrombosis—Evidence for an Anticoagulant–Independent Mechanism," Thrombosis and Haemostasis 69(2)147–151.

Reyers et al. (1983) "Stasis Induced Venous Thrombosis," In *Standardization of Animal Models of Thrombosis*, Breddin and Zimmerman (eds.) Schattauer, Stuttgart, pp. 99–104.

Evans et al. (1981) "Establishment in culture of pluripotential cells from mouse embryos," Nature 292:154–156.

Bradley et al. (1984) "Formation of germ–line chimaeras from embryo–derived teratocarcinoma cell lines," Nature 309:255–256.

Gossler et al. (1986) "Transgenesis by means of blastocyst–derived embryonic stem cell lines," Proc. Acad. Sci. USA 83:9065–9069.

Robertson et al. (1986) "Germ–line transmission of genes introduced into cultured pluripotential cells by retroviral vector," Nature 323:445–448.

Jaenisch (1988) "Transgenic Animals," Science 240:1468–1474.

Brinster et al. (1985) "Factors affecting the efficiency of introducing foreign DNA into mice by microinjecting eggs," Proc. Natl. Acad. Sci. USA 82:4438–4442.

Jaenisch (1976) "Germ line integragion and Mendelian transmission of the exogenous Moloney leukemia virus," Proc. Natl. Acad. Sci. USA 73:1260–1264.

Jahner et al. (1985) "Insertion of the bacterial gpt gene into the germ line of mice by retroviral infection," Proc. Natl. Acad Sci. USA 82:6297–6931.

Van der Putten et al. (1985) "Efficient insertion of genes into the mouse germ line via retroviral vectors," Proc. Natl. Acad Sci. USA 82:6148–6152.

Stewart et al. (1987) "Expression of retroviral vectors in transgenic mice obtained by embryo infection," EMBO J. 6:383–388.

Jahner et al. (1982) "De novo methylation and expression of retroviral genomes during mouse embryogenesis," Nature 298:623–628.

Haskell and Bowen (1995) "Efficient Production of Transgenic Cattle by Retroviral Infection of Early Embryos," Mol. Reprod. Dev. 40:386–390.

Sauer and Henderson (1988) "Site–specific DNA recombination in mammalian cells by the Cre recombinase of bateriophage P1," Proc. Natl. Acad. Sci. USA 85:5166–5170.

Jenny et al. (1987) "Complete cDNA and derived amino acid sequence of human factor V," Proc. Natl. Acad. Sci. USA 84:4846–4850.

Cripe et al. (1992) "Structure of the Gene for Human Coagulation Factor V," Biochem 31:3777–3785.

(List continued on next page.)

*Primary Examiner*—Jasemine C. Chambers
*Assistant Examiner*—Deborah J. R. Clark
*Attorney, Agent, or Firm*—Medlen & Carroll, LLP

[57] ABSTRACT

The present invention relates to compositions and methods for the screening of compounds for anticoagulant activity. In particular, the present invention relates to non-human transgenic animals expressing activated protein C ("APC")-resistant factor V proteins which display a predisposition toward spontaneous thrombosis. The present invention also provides methods for using these transgenic animals to screen compounds for anticoagulant activity.

20 Claims, 23 Drawing Sheets

OTHER PUBLICATIONS

Guinto et al. (1992) "The Complete cDNA Sequence of Bovine Coagulation Factor V," J. Biol. Chem. 267:2971–2978.

Pittman and Kaufman (1993) "Site–Directed Mutagenesis and Expression of Coagulation Factors VIII and V in Mammalian Cells," Methods Enzymol. 222:236–260.

Pittman et al. (1994) "Posttranslational Sulfation of Factor V is Required for Efficient Thrombin Cleavage and Activation and for Full Procoagulant Activity," Biochem. 33:6952–6959.

Toole et al. (1986) "A large region (≈95 kDa) of human factor VIII is dispensable for in vitro procoagulant activity," Proc. Natl. Acad. Sci. USA 83:5939–5942.

Marquete et al. (1995) "The Factor V B–Domain Provides Two Functions to Facilitate Thrombin Cleavage and Release of the Light Chain," Blood 86:3026–3034.

Pittman et al. (1994) "Role of the B Domain for Factor VIII and Factor V Expression and Function," Blood 84:4214–4225.

Mazzorana et al. (1991) "Expression of coagulation factor V gene by normal adult human hepatocytes in primary culture," Br. J. Haematol. 78:229–235.

Giddings et al. (1975) "The Immunological Localization of Factor V in Human Tissue," Br. J. Haematol. 29:57–65.

Chiu et al. (1985) "Biosynthesis of Factor V in Isolated Guinea Pig Megakaryocytes," J. Clin. Invest. 75:339–346.

Chesney et al. (1981) "Subcellular localization and secretion of factor V from human platelets," Proc. Natl. Acad. Sci. USA 78:5180–5184.

Ortel et al. (1992) "Deletion Analysis of Recombinant Human Factor V," J. Biol. Chem. 267:4189–4198.

Tracy et al. (1982) "Radioimmunoassay of Factor V in Human Plasma and Platelets," Blood 60:59–63.

Cerveny et al. (1984) "Synthesis of Coagulation Factor V by Cultured Aortic Endoehtlium," Blood 63:1467–1474.

Shen et al. (1993) "The Serine Protease Cofactor Factor V is Synthesized by Lymphocytes," J. Immunol. 150:2992–3001.

Rodgers (1988) "Vascular smooth muscle cells synthesize, secrete and express coagulation factor V," Biochim. Biophys. Acta 968:17–23.

Tracy et al. (1984) "Factor V (Quebec): a Bleeding Diathesis Associated with a Qualitative Platelet Factor V Deficiency," J. Clin. Invest. 74:1221–1228.

Roberts and Eberst (1994) Thrombosis and Hemorrhage, Loscalzo and Schafer, eds., Blackwell Scientific Publications, Boston, pp. 701–728.

Murray et al. (1995) "Factor $V_{New\ Brunswick}$: $Ala_{221}$–to–Val Substitution Results in Reduced Cofactor Activity," Blood 86:1820–1827.

Tracy and Mann (1987) "Abnormal Formation of the Prothrombinase Complex: Factor V Deficiency and Related Disorders," Hum. Pathol. 18:162–169.

Krishnaswany et al. (1987) "Activation of Human Prothrombin by Human Prothrombinase," J. Biol. Chem. 262:329–3299.

Krishnaswamy et al. (1993) "Assembly of Prothrombinase Complex," Methods Enzymol. 222:260–281.

Seligsohn et al. (1982) "Combined Factor V and Factor VIII Deficiency Among Non–Ashkenazi Jews," N. Engl. J. Med. 307:1191–1195.

Marlar and Griffin (1980) "Deficiency of Protein C Inhibitor in Combined Factor V/VIII Deficiency Disease," J. Clin. Invest. 66:1186–1189.

Gardiner and Griffin (1984) "Studies on Human Protein C Inhibitor in Normal and Factor V/VIII Deficient Plasmas," Thromb. Res. 36:197–203.

Malm et al. (1992) "Thrombembolic Disease—Critical Evaluation of Laboratory Investigation," Thromb. Haemost. 68:7–13.

Bauer (1994) Thrombosis and Hemorrhage, Loscalzo and Schafer, eds., Blackwell Scientific Publications, Boston, pp. 809–834.

Dehlbäck et al. (1993) "Familial thrombophila due to a previously unrecognized mechanism characterized by poor anticoagulant response to activated protein C: Prediction of a cofactor to activated protein C," Proc. Natl. Acad. Sci. USA 90:1004–1008.

Svensson and Dahlbäck (1994) "Resistance to Activated Protein C as a Basis for Venous Thrombosis," N. Engl. J. Med. 330:517–522.

Griffin et al. (1993) "Anticoagulant Protein C Pathway Defective in Majority of Thrombophilic Patients," Blood 82:1989–1993.

Koster et al. (1993) "Venous thrombosis due to poor anticoagulant response to activated protein C: Leiden Thrombophilla Study," Lancet 342:1503–1506.

Dahlbäck and Hildebrand (1994) "Inherited resistance to activated protein C is corrected by anticoagulant cofactor activity found to be a property of factor V," Proc. Natl. Acad. Sci. USA 91:1396–1400.

Sun et al. (1994) "Blood Coagulation Factor Va Abnormality Associated with Resistance to Activated Protein C in Venous Thrombophilia," Bllod 83:3120–3125.

Bertina et al. (1994) "Mutation in blood coagulation factor V associated with resistance to activated protein C," Nature 369:64–67.

Zöller and Dahlbäck (1994) "Linkage between inherited resistance to activated protein C and factor V gene mutation in venous thrombosis," Lancet 343:1536–1538.

Greengard et al. (1994) "Activated protein C resistance caused by Arg506Gln mutation in factor Va," Lancet 343:1361–1362.

Voorberg et al. (1994) "Association of idiopathic venous thromboembolism with single point–mutation at $Arg^{508}$ of factor V," Lancet 343:1535–1536.

Greengard et al. (1994) "Brief Report: Variability of Thrombosis Among Homozygous Siblings with Resistance to Activated Protein C due to an Arg→Gln Mutation in the Gene for Factor V," N. Engl. J. Med. 331:1559–1562.

Rosendaal (1995) "High Risk of Thrombosis in Patients Homozygous for Factor V Leiden (Activated Protein C Resistance)," Blood 85:1504–1508.

Koeleman et al. (1994) "Activated Protein C Resistance as an Additional Risk Factor for Thrombosis in Protein C–Deficient Families," Blood 84:1031–1035.

Koeleman et al. (1995) "Factor V Leiden: An Additional Risk Factor for Thrombosis in Protein S Deficient Families?" Thromb. Haemost. 74:580–583.

Nichols et al. (1996) "Moderation of Hemophilia A Phenotype by the Factor V R506Q Mutation," Blood 88:1183–1187.

Arbini et al. (1995) "Low Prevalence of the Factor V Leiden Mutation Among "Severe" Hemophiliacs with a "Milder" Bleeding Diathesis," Thromb. Haemost (1995) 74:1255–1258.

Bronson and Smithies (1994) "Altering Mice by Homologous Recombination Using Embryonic Stem Cells," J. Biol. Chem. 269:27155–27158.

Rossant and Nagy (1995) "Genome engineering: the new mouse genetics," Nature Med. 1:592–594.

Barinaga (1994) "Knockout Mice: Round Two," Science 265:26–28.

Lin et al. (1995) "Heart and lung disease in engeineered mice," Nature Med. 1:749–751.

Bi et al. (1995) "Tarteted disruption of the mouse factor VIII gene produces a model of haemophila A," Nature Genet. 10:119–121.

Suh et al. (1995) "Resolution of spontaneous bleeding events but failure of pregnancy in fibronogen–deficient mice," Genes Dev. 9:2020–2033.

Bugge et al. (1995) "Plasminogen deficiency causes severe thrombosis but is compatible with development and reproduction," Genes Dev. 9:794–807.

Ploplis et al. (1995) "Effects of Disruption of The Plasminogen Gene on Thrombosis, Growth, and Health in Mice," Circulation 92:2585–2593.

Carmeliet et al. (1994) "Physiological consequences of loss of plasminogen activator gene function in mice," Nature 368:419–424.

Carmeliet et al. (1993) "Plasminogen Activator Inhibitor–1 Gene–deficient Mice, I. Generation by Homologous Recombination and Characterization," J. Clin. Invest. 92:2746–2755.

Carmeliet et al. (1993) "Plasminogen Activator Inhibitor–a Gene–deficient Mice, II. Effects on Hemostasis, Thrombosis, and Thrombolysis," J. Clin. Invest. 92:2756–2760.

Bugge et al. (1995) "The Receptor for Urokinase–type Plasminogen Activator Is Not Essential for Mouse Development or Fertility," J. Biol. Chem. 270:16886–16893.

Healy et al. (1995) "Absence of the blood–clotting regulator thrombodulin causes embryonic lethality in mice before development of a functional cardiovascular system," Proc. Natl. Acad. Sci. USA 92:850–854.

Sambrook et al. (1989) Molecular Cloning: A Laboratory Manual, Cold Spring Harbor, Plainview, NY, pp. 8.3–8.86.

Huang (1993) "Gene Targeting Technology for Creating Transgenic Models of Lymphopoiesis," Lab. Animal Sci. 43:156–159.

Cole–Strauss et al. (1996) "Correction of the Mutation Responsible for Sickle Cell Anemia by an RNA–DNA Oligonucleotide," Science 273:1386–1389.

Ravid et al. (1991) "Selective targeting of gene products with the megakaryocyte platelet factor 4 promoter," Proc. Natl. Acad. Sci. USA 88:1521–1525.

Heckel et al. (1990) "Neonatal Bleeding in Transgenic Mice Expressing Urokinase–Type Plasminogen Activator," Cell 62:447–456.

Pinkert et al. (1992) "An albumin enhancer located 10 kb upstream functions along with its promoter to direct efficient, liver–specific expression in transgenic mice," Genes Dev. 1:268–276.

Eitzman (1996) "Bleomycin–induced Pulmonary Fibrosis in Transgenic Mice that either Lack or Overexpress the Murine Plasminogen Activator Inhibitor–1 Gene," J. Clin. Invest. 97:232–237.

Suzuki et al. (1982) "Thrombin–catalyzed Activation of Human Coagulation Factor V," J. Biol. Chem. 257:6556–6564.

Ginsburg et al. (1986) cDNA Cloning of Human Plasminogen Activator–Inhibitor from Endothelial Cells, J. Clin. Invest. 78:1673–1680.

Kozak (1991) "Structural Features in Eukaryotic mRNAs that Modulate the Initiation of Translation," J. Biol. Chem. 266:19867–19869.

Keller et al.(1995) "Thrombin–Catalyzed Activation of Recombinant Human Factor V," Biochemistry 34:4118–4124.

Mount (1982) "A catalogue of splice junction sequences," Nucl. Acids Res, 10:459–472.

Andersson et al. (1989) Cloning, Structure, and Expression of the Mitochondrial Cytochrome P–450 Sterol 26–Hydroxylase, a Bile Acid Biosynthetic Enzyme, J. Biol. Chem. 264:8222–8229.

Chen et al. (1987) "High–Efficiency Transformation of Mammalian Cells by Plasmid DNA," Mol. Cell. Biol. 2745–2752.

Nicolas et al. (1995) "Peptide Bond Cleavages and Loss of Functional Activity during Inactivation of Factor Va and Factor Va$^{R506Q}$ by Activated Protein C," J. Biol. Chem. 270:21158–21166.

Heeb et al. (1995) "Activated Protein C Resistance: Molecular Mechanisms Based on Studies Using Purified Gln$^{506}$–Factor V," Blood 85:3405–3411.

Camire et al. (1995) "The Mechanism of Inactivation of Human Platelet Factor Va from Normal and Activated Protein C–resistant Individuals," J. Biol. Chem. 270:20794–20800.

Zheng et al. (1995) "Vitronectin is not essential for normal mammalian development and fertility," Proc. Natl. Acad. Sci. USA 92:12426–12430.

Swiatek and Gridley (1993) "perinatal lethality and defects in hindbrain development in mice homozygous for a targeted mutation of the zinc finger gene Krox20," Genes Dev. 7:2071–2084.

Han et al. (1993) "Sex Determination in Single Mouse Blastomers by Polymerase Chain Reaction," J. Assist. Reprod. Genet. 10:151–156.

Galanakis (1992) "Fibrinogen Anomalies and Disease, A Clinical Update," Hematol. Oncol. Clin. North Am. 6:1171–1187.

Vu et al. (1991) "Molecular Cloning of a Functional Thrombin Receptor Reveals a Novel Porteolytic Mechanism of Receptor Activation," Cell 64:1057–1068.

Hanson et al.(1988) "Interruption of acute platelet–dependent thrombosis by thesynthetic antithrombin D–phenylalanyl–L–prolyl–L–arginyl chloromethyl ketone," Proc. Natl. Acad. Sci. USA 85:3184–3188.

Shivdasani et al. (1995) "Transcription Factor NF–E2 is Required for Platelet Formation Independent of the Actions of Thrombopoietin/MGDF in Megakaryocyte Development," Cell 81:695–704.

Gu et al. (1994) "Deletion of a DNA Polymerase β Gene Segment in T Cells Using Cell Type–Specific Gene Targeting," Science 265:103–106.

Kalafatis et al. (1995) "Characterization of the Molecular Defect in Factor V$^{R506Q}$," J. Biol. Chem. 270:4053–4057.

Ausubel et al. (eds.) (1994) Current Protocols in Molecular Biology, John Wiley & Sons, Inc., pp. 16.8.1–16.8.14.

Bagdy et al. (1992) "Comparative Studies In Vitro and Ex Vivo on the Anticoagulant Effect of a Reversible and an Irreversible Tripeptide Inhibitor of Thrombin," Thrombosis Research 67:221–231.

Cui et al. (1996) "Fatal haemorrhage and imcomplete block to embryogenesis in mice lacking coagulation factor V," Nature 384:66–68.

Gu et al. (1993) "Independent Control of Immunoglobulin Switch Recombination at Individual Switch Regions Evidenced through Cre–lox–Mediated Gene Targeting," Cell 73:1155–1164.

Iyengar et al. (1996) "Regulation and expression of transgenes in fish—a review" Transgenic–Res. 5:147–166.

Kane and Davie (1986) "Cloning of a cDNA coding for human factor V, a blood coagulation factor homologous to factor VIII and ceruloplasmin," Proc. Natl. Acad. Sci. 83:6800–6804.

Li et al. (1996) "Generation of mice with a 200–kb amyloid precursor protein gene deletion by Cre recombinase–mediated site–specific recombination in embryonic stem cells," Proc. Natl. Acad. Sci. 93:6158–6162.

McMartin (1977) "Spontaneous Atrial Thrombosis in Aged Syrian Hamsters. I. Incidence and Pathology," Thrombos. Haemostas. 38:447–456.

Mansour et al. (1988) "Disruption of the proto–oncogene int–2 in mouse embryo–derived stem cells: a general strategy for targeting mutations to non–selectable genes," Nature 336:348–352.

Meuleman (1989) "Synopsis of the Anticoagulant and Antithrombotic Profile of the Low Molecular Weight Heparinoid Org 10172 in Experimental Models," Seminars in Throm. and Hemo. 15:370–372.

Mullins and Mullins (1993) "Transgenesis in nonmurine species," Hypertension 22:630–633.

Shuman (1991) "Production of Transgenic Birds," Experientia 47:897–905.

Stassen et al. (1995) "Characterisation of a Novel Series of Aprotinin–derived Anticoagulants, II. Comparative antithrombotic effects on primary thrombus formation in vivo," Throm. and Haemo. 74:655–659.

Wang et al. (1996) "Functional redundancy of the muscle–specific transcription factors Myf5 and myogenin," Nature 379:823–825.

Zhang et al. (1996) "Inducible site–directed recombination in mouse embryonic stem cells," Nucl. Acids. Res. 24:543–548.

```
1    GGGCCATGCTTCCTAGTCTGCCCGTGCTTCTTCCTCCTGGTGGTTCTGGGAACCCGCTGGGC
       M  L  L  V  C  P  F  F  L  L  V  L  G  T  R  W  A

39   AGGGGATCCTCTGGAACTATCCTGAGCCCACAGATCCAAGTTTGAATTCTATACCTTC
     Q  G  I  L  W  N  Y  H  P  E  P  T  D  P  S  L  N  S  I  P  S

79   CTAGCAACTCAGGACTTCTTGGACCTACTTTATACGCTGAAGTTGGGACGTCATTAAAGT
     S  S  N  S  G  L  L  G  P  T  L  Y  A  E  V  G  D  V  I  K  V

119  GTAAATTTTCAGAAGGGGCTTCTTACGCAGACCACACATTTCCTGCCGAGAGGAAGGATGA
     S  K  F  S  E  G  A  S  Y  A  D  H  T  F  P  A  E  R  K  D  D

159  CCACACCTGATGACCACCACCATGCCTCACCACCACATCTACTATTCCTATGAAAACCTGACCCA
     P  T  P  D  D  P  P  C  L  T  H  I  Y  Y  S  Y  E  N  L  T  Q

199  AGGATGGGACTCAGAAGATGTTTGACAAGCAGCATGTGCTCCTATTTGCTGTGTTTGATGA
     E  D  G  T  Q  K  M  F  D  K  Q  H  V  L  L  F  A  V  F  D  E

239  AGACGATGCCAGATATAACAGTCTGTGCCCATGACCACGTCAGCTCATCTGATCGGGAT
     K  T  M  P  D  I  T  V  C  A  H  D  H  V  S  W  H  L  I  G  M

279  AGCATAAAGTGTCCACCGTCAGGCAACATCACTACGACTACTGCAAACATGACTAT
     Q  H  K  V  S  T  T  V  L  V  S  A  T  S  T  T  A  N  M  T  M

319  TGCAGGCTTACATTGACATTAAAAACTGCCCAAAGAAAACGAGGAGCCCCAAGACCCTCAC
     M  Q  A  Y  I  D  I  K  N  C  P  K  K  T  R  S  P  K  T  L  T
                                            Exon 7 ▶ Exon 8

359  TTTGGAACTATGCACCCGTGATACCTGCGAATATGGACAAAATTTACAGGTCTCAGCACTT
     I  W  N  Y  A  P  V  I  P  A  N  M  D  K  I  Y  R  S  Q  H  L

399  AAGAAGAGACCTTCACCCAAACGCACTGACAACCCCAGCATCAAACAAAGTGGGATTCTGG
     E  E  E  T  F  T  K  R  T  D  N  P  S  I  K  Q  S  G  I  L  G

439  GCCGACCCTACAGCATTTACCCTCACGGGGTGACCTTCTCTTCTTACGAAGATGGAATCAA
     S  R  P  Y  S  I  Y  P  H  G  V  T  F  S  P  Y  E  D  G  I  N

479  TCACTTACAAATGGAACATTCTAGAGTTTGATGAACCCACGGAAAACGATGCCCAGTGCCT
     F  T  Y  K  W  N  I  L  E  F  D  E  P  T  E  N  D  A  Q  C  L
                                      Exon 10 ▶ Exon 11

519  GGCTGCTTCTAATTTGTAAGAGACAGGTCCCTGGACCAGGGGTGTACAGAGGGTGGCAGA
     G  L  L  L  I  C  K  S  R  S  L  D  Q  R  G  V  Q  R  V  A  D
```

FIG. 2B

FROM FIG. 2A

```
GGGCTGGGGCAGCCACCAGGCAGGAGCCGCGCCAACTAAGGCAGTTCTATGTGGCAGCTC    120
 G  W  G  S  H  Q  A  E  A  A  Q  L  R  Q  F  Y  V  A  A
CTTCAAGAAATTGTCTACAGAGAGTATGAACAGTATTTAAGAAAGAAAGCCACGAT        240
 F  K  K  I  V  Y  R  E  Y  E  Q  Y  F  K  E  K  P  R
TCACTTTAGAAACAAAGCAGACAAACCACTAAGCATCCTCAAGGATTAAATACA          360
 H  F  R  N  K  A  D  K  P  L  S  I  H  P  Q  G  I  K  Y
TGCCGTGGCTCCTGGAGAAGAATACACCTATGAATGGATCGTCAGTGAGGACAGCGGGC     480
 A  V  A  P  G  E  E  Y  T  Y  E  W  I  V  S  E  D  S  G
GGATTTCAACTCGGGTCTGATTGGGCCTCTGCTTATCTGCAAGAAAGGCACCCTGACCG     600
 D  F  N  S  G  L  I  G  P  L  L  I  C  K  K  G  T  L  T
AAGCAAGAGCCGGAGCCAGTCACCATCCCTAATGTACACAATTAATGGCTTTGTGAATA    720
 S  K  S  S  R  S  Q  S  P  S  L  M  Y  T  I  N  G  F  V  N
GAGCTCGGGGCCAGAATTGTTTCTATTCACTTCAACGGCCAAGTCCTAGAGCAGAACC     840
 S  S  G  P  E  L  F  S  I  H  F  N  G  Q  V  L  E  Q  N
GAGCCCAGAAGGAAGATGGAATTGTTTCTTCTCATCCCAAAGCATTATCAAGCTGGGA    960
 S  P  E  G  R  W  I  V  S  S  L  I  P  K  H  Y  Q  A  G
TCGGGAGCAGAGGCGGGTACATGAAGAGATGGGAGTATTTCATAGCCGCAGAGGAGGTCA   1080
 R  E  Q  R  R  Y  M  K  R  W  E  Y  F  I  A  A  E  E  V
GGATAATTTCTCAAACCAAATTGGAAAAACATTACAAGAGAAAGTTATCTACAGGCAATATG 1200
 D  N  F  S  N  Q  I  G  K  H  Y  K  K  V  I  Y  R  Q  Y
                        Exon 8 ▶ Exon 9
CCCTGTTATCAGAGCCCAGGTCAGAGACCACTCAAGATCGTGTTCAAAAATATGGCGA    1320
 P  V  I  R  A  Q  V  R  D  T  L  K  I  V  F  K  N  M  A
     Exon 9 ▶ Exon 10
TTCTTCCTCCACCTGCAGGCAGTCACACCACGATCAGACCCAGTTCAACCGGGGAAACCT   1440
 S  S  S  T  S  G  S  H  T  T  I  R  P  V  Q  P  G  E  T
AACAAGGCCATACTACTACAGTGATGTGGACGTTACAAGGGATATTGCCTCTGGGCTGATAG 1560
 T  R  P  Y  Y  S  D  V  D  V  T  R  D  I  A  S  G  L  I
CATCGAGCAGCAGGCCGTGTTTGCTGTTTGACGAGAACAAGAGCTGGTACATTGAGG     1680
 I  E  Q  Q  A  V  F  A  V  F  D  E  N  K  S  W  Y  I  E
```

FROM FIG. 2A

CONTINUED ON FIG. 2D

```
      ACAACATCAACAAGTTCTGTGAGAATCCTGATGAGGTGAAGCGTGATGATCCCAAGTTTTACGAATCA
559    D  N  I  N  K  F  C  E  N  P  D  E  V  K  R  D  D  P  K  F  Y  E  S
      GATTCTGTTTGATGACACTGTCCAGTGGCACTTCTGCAGTGTGGGAACTCATGATGATATTTTGACC
599    G  F  C  F  D  D  T  V  Q  W  H  F  C  S  V  G  T  H  D  D  I  L  T
                                                  Exon 12 ▼ Exon 13
      TGACCCTGTTCCCCATGCGTGGTGAATCTGTGACAGTTACAATGGATAATGTTGGAACTTGGATGTTG
639    L  T  L  F  P  M  R  G  E  S  V  T  V  T  M  D  N  V  G  T  W  M  L
      ATGTTAAGTGTAATCGGGATTATGACAATGAGGACTCATATGAGATTTATGAACCTCCTGCACCTACA
679    M  V  K  C  N  R  D  Y  D  N  E  D  S  Y  E  I  Y  E  P  P  A  P  T
      ACAACGAAGATGATGATTACCAGTACTTACTGGCGTCATCATTAGGAATTAGGTCATTCAAAAACTCA
719    D  N  E  D  D  Y  Q  Y  L  L  A  S  S  L  G  I  R  S  F  K  N  S
      ACAGCTCTGAGTTCATATCTCCAAGCACAGAGTTGTTGACTCAAACTCTTCGAATCCTTAGT
759    N  S  S  E  F  I  S  P  S  T  D  R  V  D  S  N  S  S  R  I  L  S
      GAGCCACCGTGGCTGGTACCCTCCTTAGAAAACCTCATTGGCTTAGATGAGAACTTCGTCCTCAACTCT
799    G  A  T  V  A  G  T  L  R  N  L  I  G  L  D  E  N  F  V  L  N  S
      AGTCAAAACATCACAATGGTATACCTTCCTCTTGGTCCAAAAGGATCTGGGAATCGAGAACAAGAT
839    Q  S  N  I  T  M  V  L  L  P  L  G  P  K  G  S  G  N  R  B  Q  D
      CCTGGATGAAAGCGCCAGCTGGTAAAACTGGCAGACACCCAAAGAATTCGTATTCTGGAATG
879    S  W  M  K  A  P  A  G  K  T  G  R  H  S  N  P  K  N  S  Y  S  G  M
      CTTCCAAATTTCTGAATAGACGATGGCGTGTGGCTTCTGAAAAGGGTAGTTATGAAATAATAGCAGCA
919    T  S  K  F  L  N  R  R  W  R  V  A  S  E  K  G  S  Y  E  I  I  A  A
      ATATCACAGTACCTCGGGGAGAGACACCTCACACAACAAGAAAGCCAAGTGACCTCCCA
959    N  I  T  P  R  G  B  S  T  S  H  T  N  T  T  R  K  P  S  D  L  P
      ACAGTGGTTTCAGAGAAAGACAGTTATTCATCAGGAAGAAGAAGAATAAGAAGCTTGCA
999    N  S  G  F  Q  K  R  Q  L  F  I  R  T  R  K  K  K  N  K  L  A
      ATTCCCCATTTCCAGACACAGGAGACTACTTACTCACTGTTACTCCACAAGTCCAATGAAACAGCT
1039   H  S  P  F  P  D  R  R  L  N  H  S  L  L  H  K  S  N  E  T  A
      TTCCTGACTATAATCAGTACTGAAAAATGACACTGAGCTCTTCTTTAGATCTTTATCAG
1079   L  P  D  Y  N  Q  Y  S  K  N  D  T  E  Q  M  S  S  L  D  L  Y  Q
```

```
                    Exon 11 ▼ Exon 12
         AACATCATGAGCACTATCAACGGCTACGTGCCCGAGAGCATTTCCACTCTGG   1800
          N  I  M  S  T  I  N  G  Y  V  P  E  S  I  S  T  L
         ATCCACTTCACTGGGCACTGGACACCT                             1920
          I  M  F  T  G  H  S  P  I  Y  G  R  R  H  E  D  T ACCACCATGAATTCCAATCCAAAACGCAGAAACCTAAGACTGAGATTCAGAG   2040
          T  T  M  N  S  N  P  K  R  R  N  L  R  L  R  F  R
         TCCATGACAACTCGGAGAATTCATGATTCCTTAGAAAATGAATTTGGCATAG   2160
          S  M  T  T  R  R  I  H  D  S  L  E  N  E  F  G  I
         TCATTGAATCCAGAGAGAAATGAGTTCAATCTCACTGCTCTCGCTCTGGAGA   2280
          S  L  N  P  E  E  N  E  F  N  L  T  A  L  A  L  E
         AAAATCATCAATAATAACCTCAAAGACTTTCAAAGAACACTTCCTGGCTCAG   2400
          K  I  I  N  N  N  L  K  D  F  Q  R  T  L  P  G  S
         TCTACAGAACATCGTTCCAGCTCATATCATGAAAATGATATGGAAAATCCAC   2520
          S  T  E  H  R  S  S  S  Y  H  E  N  D  M  E  N  P
         AAACCTAAAACCATCAAGACACAGGAGACCCCACTAGCCGAGTTGATACCCTT   2640
          K  P  K  T  I  K  T  G  R  P  H  M  M  K  H  R  F
         AAGTCTGAGGAGGACATTCCTAGCGAGTTGGATAAGCTGACCAACAGTCCTCAAAAGATCA   2760
          K  S  E  E  D  I  P  S  E  L  I  P  L  K  Q  K  I
         AATGGTGAAGACACAGATGTGGACATAAATCTCCACATGTAAGACAGGAGGAAGAAA   2880
          N  G  E  D  T  D  V  D  K  L  T  N  S  P  Q  N  Q
         ACATTTTCTGGAGTTGGACATAAATCTCCACATGTAAGACAGGAGGAAGAAA   3000
          T  F  S  S  G  V  G  H  K  S  P  H  V  R  Q  E  E  E
         CTACACAGTCCCTCTATCTCCAAGGGGCTTTGACCCTTTGAGAGGACATAACC   3120
          L  H  S  P  L  S  P  R  G  F  D  P  L  R  G  H  N
         CTTTCTCCAGACCTGAACCAGACCTCTCCTTCAATGAGTACGGACAGGTCAC   3240
          L  S  P  D  L  N  Q  T  S  P  S  M  S  T  D  R  S
         TCAGTGCCCGCCAGAGGAACACTCTCCAACATTTCCTGCCCAAGATCCTGATC   3360
          S  V  P  A  E  E  H  S  P  T  F  P  A  Q  D  D  P  D
```

```
       AAACACACTCTACCACAGATCCTAGCTACAGATCCTCCGCCAGAGCTCAGCCAGGGCTTGATTAT
1119    Q  T  H  S  T  D  P  S  Y  R  S  S  P  P  E  L  S  Q  G  L  D  Y
       CAGACCAAAGTCAAAAGTCATCTTTCTCAGATGATGACCAAGCAATCCCTTCCTCAGACTTAAGC
1159    P  D  Q  S  Q  K  S  S  F  S  S  D  D  D  Q  A  I  P  S  S  D  L  S
       ATCAGTTGCTCCTTTCTCCAGAAGACAATCAGAAGACCTCCTCCCAGACCTGGGTCAGGCCCCCTT
1199    D  Q  L  L  S  P  E  D  N  Q  K  T  S  S  P  D  L  G  Q  V  P  L
       TTTCTCCAGATGATAACCAGAAGACCTCCTCCCAGACCTGGGTCAGGTGCCCTTTCTCTAGATGAC
1239    L  S  P  D  D  N  Q  K  T  S  S  P  D  L  G  Q  V  P  L  S  D  D
       ACAACCAGATGATCACCTCCCCAGACCTGGGTCAGGTGCCCCTTTCTTCTGATAACCAGAAGACCTCT
1279    D  N  Q  M  I  T  S  P  D  L  G  Q  V  P  L  S  S  D  N  Q  K  T  S
       TCCTAGACCTGAGTCAGGTACCTCTCCAGACAATAGTCAGGTGACCGTGTCCCCAGACCTCTCCACCA
1319    F  L  D  L  S  Q  V  P  L  S  S  D  Q  N  E  T  S  S  T  D  L  L
       TGCCACTCCCCTTCAGACCTGTCAGGTGACCGTGTCCCCAGACCTCTTGACCCTCTCCACCA
1359    L  P  L  P  S  D  N  S  Q  V  T  V  S  P  D  L  S  L  L  T  L  S  P
       CAGACCTCATCCAGAGACAAACCCTGCTCTTAATCATGGACACAAAGCATCCTCTGCAGACCCTGATCAA
1399    P  D  L  I  Q  T  N  P  A  L  N  H  G  H  K  A  S  S  A  D  P  D  Q
       GGACTCTTCCTCATCCAGATCTTGACACTCCACCTCCACCATCTCCACCACTCAATAACACT
1439    R  T  L  P  H  P  D  L  T  H  I  P  P  S  P  S  P  T  L  N  T
       ATGGAGACGACGTTGAGATTGTTCCAAGTGAGGAGCCAGAGAGAATAGATGAAGATTATGCCGAGGAT
1479    B  G  D  D  V  E  I  V  P  S  E  E  P  E  R  I  D  E  D  Y  A  E  D
       ATTCCTCCAGAAATCCTGACACTATCGCAGCATGGTACCTCCGAGGCCACGGTGGACACAAAAAATTC
1519    N  S  S  R  N  P  D  T  I  A  W  Y  L  R  G  H  G  G  H  K  K  F
       GTGAAATGGACCATGAAGACACAGGCCACACTCCAAAGGACACCACATACAAGAAAGTCGTTTTCAGA
1559    S  E  M  D  H  E  D  T  G  H  T  P  K  D  T  T  Y  K  K  V  V  F  R
       AGCACCTTGGCATTCTGGTCCTGTGATCCGGGTGAAGTGGATGATGTGATCCAAGTTCGATTTAAA
1599    E  H  L  G  I  L  G  P  V  I  R  A  E  V  D  D  V  I  Q  V  R  F  K
```

FIG. 2F

FROM FIG. 2E

```
GACCTAAGTCATGACTTTTACCCTGATGACATTGGTCTAACATCTTTCTTTC    3480
 D   L   S   H   D   F   Y   P   D   D   I   G   L   T   S   F   F
CTCTTTACCATCTCTCCAGAATTGGATCAGACAATTATTTACCAGACCTGG     3600
 L   F   T   I   S   P   E   L   D   Q   T   I   I   Y   P   D   L
TCTCCAGATGACAACCAGAAGACCTCCCCAGACCTGGGTCAGGTGTCCC       3720
 S   P   D   D   N   Q   K   T   S   P   D   L   G   Q   V   S
AACCAGAAGACGACCTCCCCAGACCTGGGTCAGGTGCCCCTTTCTCCAGATG    3840
 N   Q   K   T   S   P   D   L   G   Q   V   P   L   S   P   D
TCCCCAGATCTGGGTCAGGTGCCTCTCTTTTTCCTGAAGACAACCAGAATTACT  3960
 S   P   D   L   G   Q   V   P   L   F   P   E   D   N   Q   N   Y
ACTCTCTCCTGATTTTGGTCAGACAGTCCTTTCCCAGACTTGGATCAGC       4080
 T   L   S   P   D   F   G   Q   T   V   L   S   P   D   L   D   Q
GATTTAATGAGATAATCCTAGCCCCAGACCTTGGTCAAGTGACCCTCTC       4200
 D   F   N   E   I   I   L   A   P   D   L   G   Q   V   T   L   S
GCATCCTACCCTCCAGATTCTGGTCAGGCTTCATCGCTTCCAGAACTGAATC    4320
 A   S   Y   P   P   D   S   G   Q   A   S   S   L   P   E   L   N
TCTTTGTCAAGGAAATTAACCCTCTCTTGTTGTAGTAGTCTCAGTAGAGTAG    4440
 S   L   S   R   K   F   N   P   L   V   V   G   L   S   R   V
GACTTTGTAACCTATAATGACCCCTACAGAACAGACACTAGGACAGATGTCA    4560
 D   F   V   T   Y   N   D   P   Y   R   T   D   T   R   T   D   V
TACTATATTGCAGCTGAAGAAATAACCTGGAATTACGCAGAGTTTGCACAAA    4680
 Y   Y   I   A   A   E   E   I   T   W   N   Y   A   E   F   A   Q
AAATACCTTGATAGCACGTTTACPAGTCGTGATCCTCGGGCAGAATATGAGG    4800
 K   Y   L   D   S   T   F   T   S   R   D   P   R   A   E   Y   E
AATTTGGCATCCAGACCGTATTCTTCATGCTCACGGACTTTCCTATGAAA     4920
 N   L   A   S   R   P   Y   S   L   H   A   H   G   L   S   Y   E
```

FROM FIG. 2E
CONTINUED ON FIG. 2H

```
      AATCCTCAGAGGGGAAGACTTATGAAGATGAATCTCCTGAATGGTTTCAGGAAGATGATGCTGTCCAGC
1639   N  P  Q  R  G  R  L  M  K  M  N  L  L  N  G  F  Q  E  D  D  A  V  Q
       AGAACCCTGGTTCTGCCTGCCGGGCTTGGGCCTACTATTCTGCAGTGAATGTGGAGAGGGACATCCACT
1679   E  N  P  G  S  A  C  R  A  W  A  Y  Y  S  A  V  N  V  E  R  D  I  H
       AGCGCAACCTGCCTATGGACATGAGAGAGTTTGTCTTACTCTTTATGGTCTTTGATGAAGAAGAGCT
1719   E  R  N  L  P  M  D  M  R  E  F  V  L  L  F  M  V  F  D  E  K  K  S
       AAAATGCCCACAAGTTTTACGCAATTAATGGGATGATCTACAACCTGCCCGGCCTGAGAATGTACGAGC
1759   K  N  A  H  K  F  Y  A  I  N  G  M  I  Y  N  L  P  G  L  R  M  Y  E
       ACGTGGTTCACTTCCATGGCCAGACCCTGCTGGATAATAGGACCAAACAGCACCAGTTAGGCGTCTGGC
1799   H  V  V  H  F  H  G  Q  T  L  L  D  N  R  T  K  Q  H  Q  L  G  V  W
       GCTGGTGGCTCCTAGACACAGAGGTTGGAGAAAACCAGGTAGCTGGCATGCAAACGCCATTTCTCATCA
1839   G  W  W  L  D  T  E  V  G  E  N  Q  V  A  G  M  Q  T  P  F  L  I
       ATTCACAGATCAAGGCTTCGGAATATCTGACTTATTGGGAGCCCAGATTAGCACGATTAAACAATGCTG
1879   I  H  Q  I  K  A  S  E  Y  L  T  Y  W  E  P  R  L  A  R  L  N  N  A
       AACCTTGGATCCAGGTGGACATGGAGAAGGAAGTTGTAGTCACCGGGATACAAACCCAAGGTGCTAAAC
1919   K  P  W  I  Q  V  D  M  Q  K  E  V  V  V  T  G  I  Q  T  Q  G  A  K
       ACCAAACCAACTGGCAGATCTTCAGAGGGAAGAGCGGGAAGAGCGTGATGTATTTTACTGGTAATTCAG
1959   D  Q  T  N  W  Q  I  F  R  G  K  S  G  K  S  V  M  Y  F  T  G  N  S
       ACATTAGGATACACACCCAACAAATCCTATAATAGACCCTGGGGTCGCAGGCTGCAGGGCTGTGAGG
1999   Y  I  R  I  H  P  T  K  S  Y  N  R  P  T  L  R  L  E  L  Q  G  C  E
       AGCAAATTACTGCCATCTCTTCATTTAAAAAGTCGTGTGGGAGACTACTGGGAGCCCTCCCTTGCCCGCC
2039   K  Q  I  T  A  S  S  F  K  K  S  W  G  D  Y  W  E  P  S  L  A  R
       AGCAGTGGTTACAAGTCGATCTGCTCAAAATCAAGAAGGTAACGGCCATCGTAACGCAGGGCTGTAAGT
2079   K  Q  W  L  Q  V  D  L  L  K  I  K  K  V  T  A  I  V  T  Q  G  C  K
       AGGGTGTGGCATGGAAACCTTACCGACAGAAATCCTCCATGGTGGACAAGATTTTGAAGGAAACAGCA
2119   Q  G  V  A  W  K  P  Y  R  Q  K  S  S  M  V  D  K  I  F  E  G  N  S
       TTATCCGACATCATTCCTAAAACATGGAACCAGAGCATCGCCCTTCGCCTAGAGCTCTTCGGCTGTGACA
2159   F  I  R  I  I  P  K  T  W  N  Q  S  I  A  L  R  L  E  L  F  G  C  D
```

FIG. 2H

```
CCAATAGCAGTTACACCTATGTATGGCATGCCACCAAGCGCTCAGGGCCAG     5040
 P  N  S  S  Y  T  Y  V  W  H  A  T  K  R  S  G  P
CAGGCTTGATCGGCCCCCCTTCTGATCTGCCGGAAAGGAACACTTCACATGG    5160
 S  G  L  I  G  P  L  L  I  C  R  K  G  T  L  H  M
GGTACTATGAAAAGTCCAAGGGGTCACGGAGAATTGAATCCCCAGAAGAGA     5280
 W  Y  Y  E  K  S  K  G  S  R  R  I  E  S  P  E  E
AAGAGTGGGTGAGGCTACACCTGCTGAACATGGGCGGCTCCGAGATATTC      5400
 Q  E  W  V  R  L  H  L  N  M  G  G  S  R  D  I
CCCTTCTGCCTGGTTCATTTAAAACTCTTGAAATGAAGGCATCCAAGCCTG     5520
 P  L  P  G  S  F  K  T  L  E  M  K  A  S  K  P
TAGACAAAGAGTGTAAGATGCCAATGGGACTAAGCACTGGTGTCATATCTG     5640
 I  D  K  E  C  K  M  P  M  G  L  S  T  G  V  I  S
GTTCATACAATGCTTGGAGTATAGAAAAACTGCATTAGATTTTCCCATTA      5760
 G  S  Y  N  A  W  S  I  E  K  T  A  L  D  F  P  I
ACTACCTAAAGTCCTGCTTTACCACGGAGTTCCAAGTTGGCTTACAGCTCTG    5880
 H  Y  L  K  S  C  F  T  E  F  Q  V  A  Y  S  S
ATGGCTCTACAATAAAAGAGAATCGACTTGACCCACCATTGTGGCTAGAT      6000
 D  G  S  T  I  K  E  N  R  L  D  P  P  I  V  A  R
TGAACGGATGTTCCACACCACTGGGCCTGGAAGATGGACGGATTCAAGACA     6120
 V  N  G  C  S  T  P  L  G  L  E  D  G  R  I  Q  D
TGAACGCCCAGGCCGCGTGAACGCTGGCAAGCCAAGGCAAACAACAACA       6240
 L  N  A  Q  G  R  V  N  A  W  Q  A  K  A  N  N  N
CTCTGTCCTCTGAGATGTACGTGAAGAGCTACGCATCCAGTACAGTGACC      6360
 S  L  S  S  E  M  Y  V  K  S  Y  S  I  Q  Y  S  D
ATACCAAGGGCACATGAAGAACTTTTCAACCGCCCATTATTTCCAGAT        6480
 N  T  K  G  H  M  K  N  F  F  N  P  P  I  I  S  R
TTTATTAGAATTAAATTCCAAAAAAAAAAAAAAAAAAA                  6585
 I  Y  .
```

FROM FIG. 2G

```
              306 (FV) ↓
HUM   FV      IDIKNCPKKTRNLKKITREQR        SEQ ID NO:6
BOV   FV      IDIKNCAKKTRNPKKLTRDQR        SEQ ID NO:7
MUS   FV      IDIKNCPKKTRSPKTLTREQR        SEQ ID NO:8

506(FV) ↓
HUM   FV      LICKSRSLDRRGIQRAADIEQ        SEQ ID NO:9
BOV   FV      LICKSRSLDRRGIQRAADIEQ        SEQ ID NO:10
MUS   FV      LICKSESLDQRGVQRVADIEQ        SEQ ID NO:11
HUM   FVIII   LICYKESVDQRGNQIMSDKRN        SEQ ID NO:12
MUS   FVIII   LICYKESVDQRGNQMMSDKRN        SEQ ID NO:13

679(FV) ↓
HUM   FV      EPPESRVMATRKMHDELEPED        SEQ ID NO:14
BOV   FV      EPSGSTAMTTKKIHDSSEIED        SEQ ID NO:15
MUS   FV      EPPAPTSMTTRRIHDSLENEF        SEQ ID NO:16
```

FIG. 4A

```
              709 (FV) ↓
HUM   FV      QNRLAAALGIRSFRNSSLNQE        SEQ ID NO:17
BOV   FV      QDELALILGLRSFRNSSLNQE        SEQ ID NO:18
MTJS  FV      QYLLASSLGIRSFKNSSLNPE        SEQ ID NO:19

1018 (FV) ↓
HUM   FV      KHTHHAPLSPRTFHPLRSEAY        SEQ ID NO:20
BOV   FV      KPAYHVPLSPRSFHPLRGEVN        SEQ ID NO:21
MUS   FV      KLALHSPLSPRGFDPLRGHNH        SEQ ID NO:22

1545 (FV) ↓
HUM   FV      DPDNIAAWYLRSNNGNRRNYY        SEQ ID NO:23
BOV   FV      NPDNIAAWYLRSNTGNRKYYY        SFQ ID NO:24
MUS   FV      NPDTIAAWYLRGHGGHKKFYY        SEQ ID NO:25
```

```
<EXON 7>........<EXON 8> GTAAGCAACACAGAAATACGGAAGCAAGGAAAAATTAAACAGGGC
AAGACAGATCAAGGACTGGCAGTTTTAATATATTTAAATGTATTCATCTAATTATAAAATCAAACA
TAGCTCTCAGTTTTATTAGCATTTCATTCTTGTATATCCTACTTAATTTAAAGATCTGGATCGAAAA
GTAGAAAAGAATAGAGAGAATAAAGCAGAGTCAGTATCATTGGAGGAGTAAGGAATACTATATGGGA
ACTAATTCCATCTGGTCACAAATAAGCATAATGAGACACACCCATACATCCCAAGGTTGTCTGCAAA
GTGTGTCCCAACTCTTATAGCAAAGTAAATATGACCGAGCAAGGTGCACACA CCCACTGCTGCAC
TGCACATCTGTGTGCACACCTGTCCATACATGCACACAAGCAGTGCCTTCATCTCGTCTGAAATAG
TTCTCATGAGTGACCTTAAACACGGAAATAATAACTATGACTTAACTTTTCTAG <EXON9> GTGGG
AACCTTTCACTTCTTGGAGACTACTGATCTCCGAGAGGCATCCACAGTGTTCTTCTTGTATTGTCCAGT-
GGTTATGACAAACGCAGTCATTAATACGGNAGGGTTATCTCTCCTTTCTGAGTGTCATNGGCGCCATCT
AGTGGACAGATATTGAACAGTACATGCTATCCATAGTCAGGAGTTTATTATGATGAAATAATTTTCTAAAA
CTTCATATTAATTACTCTAAATAAAAGCTAAGGTAGATATTTATTATGATGAAATAATAACCTTTAAAAAAAA
TTAAGAGCGTATATTTTCCAG <EXON 10> GTATTTTATACATAACATTAGGTCTCACTACGGAATAGGA
AAAAAAAAAAAAAAAGAGGAATTTCCCCTGCTGGCACAGATTAGGTCTCACTACGGAATAGGA
GGAT.....TCGTCCATNTGGAACACGGTCAGTCAGCCATTCTGANAAGTTTTCCAGTACTCTGACCTAC
AACCTTTCACTTCTTGGAGACTACTGATCTCCGAGAGGCATCCACAGTGTTCTTCTTGTATTGTCCAGT
GGTTATGACAAACGCAGTCATTAATACOGNAGGGTTATCTCTCCTTTCTGAGTGTCATNGGCGCCATCT
AGTGGACAGATATTGAACAGTACATGCTATCCATAGTCAGGAGTTTTAATACAAAAGAATATTTT
CTTCATATTAATTACTCTAAATAAAAGCTAAGGTAGATATTTATTATGATGAAATAATTTTCTAAAA
TTAAGAGCGTATATTTTCCAG <EXON 10> GTATTTTATACATAACATAACCTTTAAAAAAAAA
AAAAAAAAAAAAAAAGAGGAATTTCCCCTGCTGGCACAGATTAGGTCTCACTACGGAATAGGA
GGAT TCGTCCATNTGGAACACGGTCAGTCAGCCATTCTGANAAGTTTTCCAGTACTCTGACCTAC
AGTGTTATNCTAAGGGAATTTCCCCCTCAGTCTGGGTATTTTGACTGAATTCTCTGACTCCTTCTTTGT
TCACATATTAGCTTTATCTCTGACAAGGGTTTGGTAANTCATGACCTCCTAGGTGCCAGACACGTGGCT
CCTCTGGACCCCACGACAATGGGACATCGACACCCACCAGTGATCACTGCCCTTTCCCTG
CAG <EXON 11> GTAAGTCAGACTCCCGTGTCCACACTGGTCGCAGTGTGTCGTGTACCAAAGG
AAAAATGTGATGCTGGGCATAACTCTCTAA....<ENON 12>....TTTCCTGAGCTTTCAGCCTTCT
CTTCTCTGTCTCTTATGAAG <EXON 13>
```

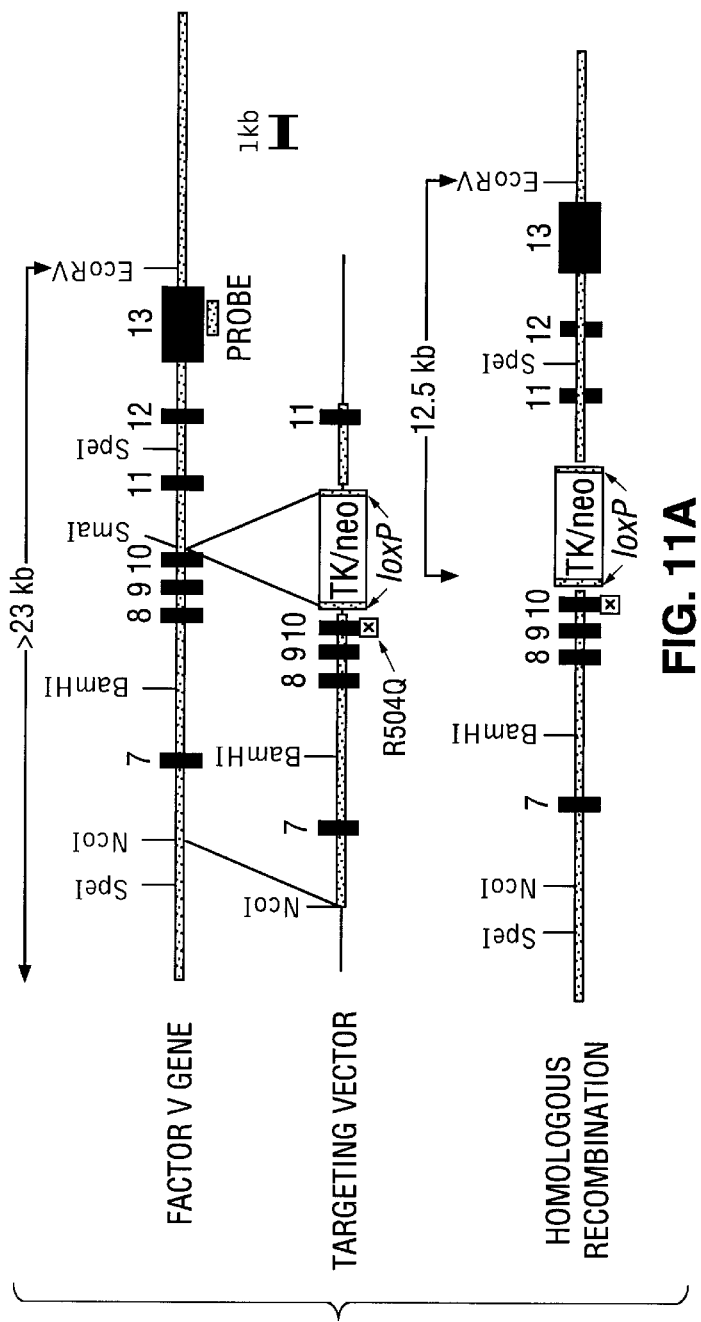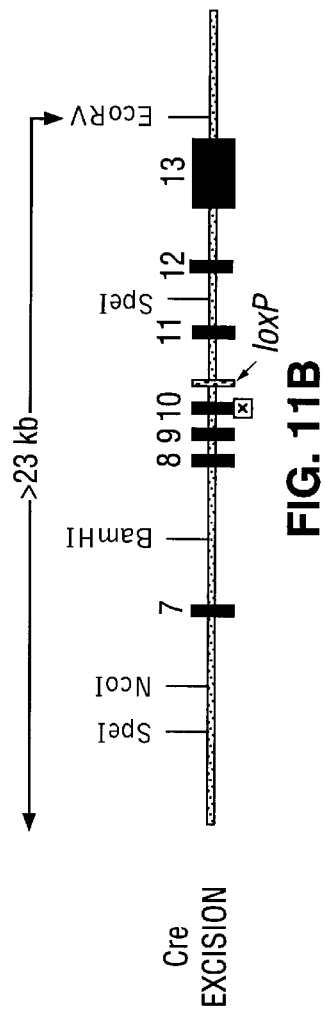
FIG. 11A
FIG. 11B

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:

```
        (A) LENGTH: 17 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:1:

CTGGAGAAAG GGACACC                                                      17

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:2:

TCATAGCCGC AGAGGAGGTC A                                                 21

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:3:

ATGGGGAACA GGGTCAAGGT G                                                 21

(2) INFORMATION FOR SEQ ID NO:4:

(i) SEQUENCE CHARACTERISTICS:
        (A) LENGTH: 6585 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "DNA"

(ix) FEATURE:
         (A) NAME/KEY: CDS
         (B) LOCATION: 6..6554

(xi) SEQUENCE DESCRIPTION: SEQ ID NO:4:

GGGCC ATG CTC CTA GTC TGC CCG TGC TTC TTC CTC CTG GTG GTT CTG           47
      Met Leu Leu Val Cys Pro Cys Phe Phe Leu Leu Val Val Leu
       1               5                  10

GGA ACC CGC TGG GCG GGC TGG GGC AGC CAC CAG GCA GAG GCC GCG CAA         95
Gly Thr Arg Trp Ala Gly Trp Gly Ser His Gln Ala Glu Ala Ala Gln
 15                  20                  25                  30

CTA AGG CAG TTC TAT GTG GCA GCT CAG GGG ATC CTC TGG AAC TAT CAT        143
Leu Arg Gln Phe Tyr Val Ala Ala Gln Gly Ile Leu Trp Asn Tyr His
                 35                  40                  45

CCT GAG CCC ACA GAT CCA AGT TTG AAT TCT ATA CCT TCC TTC AAG AAA        191
Pro Glu Pro Thr Asp Pro Ser Leu Asn Ser Ile Pro Ser Phe Lys Lys
         50                  55                  60
```

```
ATT GTC TAC AGA GAG TAT GAA CAG TAT TTT AAG AAA GAA AAG CCA CGA        239
Ile Val Tyr Arg Glu Tyr Glu Gln Tyr Phe Lys Lys Glu Lys Pro Arg
            65                  70                  75

TCT AGC AAC TCA GGA CTT CTT GGA CCT ACT TTA TAC GCT GAA GTT GGG        287
Ser Ser Asn Ser Gly Leu Leu Gly Pro Thr Leu Tyr Ala Glu Val Gly
 80                  85                  90

GAC GTC ATT AAA GTT CAC TTT AGA AAC AAA GCA GAC AAA CCA CTA AGC        335
Asp Val Ile Lys Val His Phe Arg Asn Lys Ala Asp Lys Pro Leu Ser
 95                 100                 105                 110

ATC CAT CCT CAA GGG ATT AAA TAC AGT AAA TTT TCA GAA GGG GCT TCT        383
Ile His Pro Gln Gly Ile Lys Tyr Ser Lys Phe Ser Glu Gly Ala Ser
            115                 120                 125

TAC GCA GAC CAC ACG TTC CCT GCC GAG AGG AAG GAT GAT GCC GTG GCT        431
Tyr Ala Asp His Thr Phe Pro Ala Glu Arg Lys Asp Asp Ala Val Ala
            130                 135                 140

CCT GGA GAA GAA TAC ACC TAT GAA TGG ATC GTC AGT GAG GAC AGC GGG        479
Pro Gly Glu Glu Tyr Thr Tyr Glu Trp Ile Val Ser Glu Asp Ser Gly
            145                 150                 155

CCC ACA CCT GAT GAC CCA CCA TGC CTC ACC CAC ATC TAC TAT TCC TAT        527
Pro Thr Pro Asp Asp Pro Pro Cys Leu Thr His Ile Tyr Tyr Ser Tyr
160                 165                 170

GAA AAC CTG ACC CAG GAT TTC AAC TCG GGT CTG ATT GGG CCT CTG CTT        575
Glu Asn Leu Thr Gln Asp Phe Asn Ser Gly Leu Ile Gly Pro Leu Leu
175                 180                 185                 190

ATC TGC AAG AAA GGC ACC CTG ACC GAG GAT GGG ACT CAG AAG ATG TTT        623
Ile Cys Lys Lys Gly Thr Leu Thr Glu Asp Gly Thr Gln Lys Met Phe
                195                 200                 205

GAC AAG CAG CAT GTG CTC CTA TTT GCT GTG TTT GAT GAA AGC AAG AGC        671
Asp Lys Gln His Val Leu Leu Phe Ala Val Phe Asp Glu Ser Lys Ser
            210                 215                 220

CGG AGC CAG TCA CCA TCC CTA ATG TAC ACA ATT AAT GGC TTT GTG AAT        719
Arg Ser Gln Ser Pro Ser Leu Met Tyr Thr Ile Asn Gly Phe Val Asn
            225                 230                 235

AAG ACG ATG CCA GAT ATA ACA GTC TGT GCC CAT GAC CAC GTC AGC TGG        767
Lys Thr Met Pro Asp Ile Thr Val Cys Ala His Asp His Val Ser Trp
240                 245                 250

CAT CTG ATC GGG ATG AGC TCG GGG CCA GAA TTG TTT TCT ATT CAC TTC        815
His Leu Ile Gly Met Ser Ser Gly Pro Glu Leu Phe Ser Ile His Phe
255                 260                 265                 270

AAC GGC CAA GTC CTA GAG CAG AAC CAG CAT AAA GTG TCC ACC GTC ACC        863
Asn Gly Gln Val Leu Glu Gln Asn Gln His Lys Val Ser Thr Val Thr
                275                 280                 285

CTG GTC AGC GCA ACA TCT ACG ACT GCA AAC ATG ACT ATG AGC CCA GAA        911
Leu Val Ser Ala Thr Ser Thr Thr Ala Asn Met Thr Met Ser Pro Glu
            290                 295                 300

GGA AGA TGG ATT GTT TCT TCT CTC ATC CCA AAG CAT TAT CAA GCT GGG        959
Gly Arg Trp Ile Val Ser Ser Leu Ile Pro Lys His Tyr Gln Ala Gly
            305                 310                 315

ATG CAG GCT TAC ATT GAC ATT AAA AAC TGC CCA AAG AAA ACG AGG AGC       1007
Met Gln Ala Tyr Ile Asp Ile Lys Asn Cys Pro Lys Lys Thr Arg Ser
            320                 325                 330

CCC AAG ACC CTC ACT CGG GAG CAG AGG CGG TAC ATG AAG AGA TGG GAG       1055
Pro Lys Thr Leu Thr Arg Glu Gln Arg Arg Tyr Met Lys Arg Trp Glu
335                 340                 345                 350

TAT TTC ATA GCC GCA GAG GAG GTC ATT TGG AAC TAT GCA CCC GTG ATA       1103
Tyr Phe Ile Ala Ala Glu Glu Val Ile Trp Asn Tyr Ala Pro Val Ile
            355                 360                 365
```

-continued

| | | |
|---|---|---|
| CCT GCG AAT ATG GAC AAA ATT TAC AGG TCT CAG CAC TTG GAT AAT TTC<br>Pro Ala Asn Met Asp Lys Ile Tyr Arg Ser Gln His Leu Asp Asn Phe<br>          370                          375                        380 | 1151 |
| TCA AAC CAA ATT GGA AAA CAT TAC AAG AAA GTT ATC TAC AGG CAA TAT<br>Ser Asn Gln Ile Gly Lys His Tyr Lys Lys Val Ile Tyr Arg Gln Tyr<br>          385                          390                        395 | 1199 |
| GAA GAA GAG ACC TTC ACC AAA CGC ACT GAC AAC CCC AGC ATC AAA CAA<br>Glu Glu Glu Thr Phe Thr Lys Arg Thr Asp Asn Pro Ser Ile Lys Gln<br>400                          405                        410 | 1247 |
| AGT GGG ATT CTG GGC CCT GTT ATC AGA GCC CAG GTC AGA GAC ACA CTC<br>Ser Gly Ile Leu Gly Pro Val Ile Arg Ala Gln Val Arg Asp Thr Leu<br>415                          420                        425                        430 | 1295 |
| AAG ATC GTG TTC AAA AAT ATG GCG AGC CGA CCC TAC AGC ATT TAC CCT<br>Lys Ile Val Phe Lys Asn Met Ala Ser Arg Pro Tyr Ser Ile Tyr Pro<br>                          435                        440                        445 | 1343 |
| CAC GGG GTG ACC TTC TCT CCT TAC GAA GAT GGA ATC AAT TCT TCC TCC<br>His Gly Val Thr Phe Ser Pro Tyr Glu Asp Gly Ile Asn Ser Ser Ser<br>          450                          455                        460 | 1391 |
| ACC TCA GGC AGT CAC ACC ACG ATC AGA CCA GTT CAA CCG GGG GAA ACC<br>Thr Ser Gly Ser His Thr Thr Ile Arg Pro Val Gln Pro Gly Glu Thr<br>                465                        470                        475 | 1439 |
| TTC ACT TAC AAA TGG AAC ATT CTA GAG TTT GAT GAA CCC ACG GAA AAC<br>Phe Thr Tyr Lys Trp Asn Ile Leu Glu Phe Asp Glu Pro Thr Glu Asn<br>480                          485                        490 | 1487 |
| GAT GCC CAG TGC CTA ACA AGG CCA TAC TAC AGT GAT GTG GAC GTT ACA<br>Asp Ala Gln Cys Leu Thr Arg Pro Tyr Tyr Ser Asp Val Asp Val Thr<br>495                          500                        505                        510 | 1535 |
| AGG GAT ATT GCC TCT GGG CTG ATA GGG CTG CTT CTA ATT TGT AAG AGC<br>Arg Asp Ile Ala Ser Gly Leu Ile Gly Leu Leu Leu Ile Cys Lys Ser<br>                515                        520                        525 | 1583 |
| AGG TCC CTG GAC CAG AGG GGT GTA CAG AGG GTG GCA GAC ATC GAG CAG<br>Arg Ser Leu Asp Gln Arg Gly Val Gln Arg Val Ala Asp Ile Glu Gln<br>                530                        535                        540 | 1631 |
| CAG GCC GTG TTT GCT GTG TTT GAC GAG AAC AAG AGC TGG TAC ATT GAG<br>Gln Ala Val Phe Ala Val Phe Asp Glu Asn Lys Ser Trp Tyr Ile Glu<br>          545                          550                        555 | 1679 |
| GAC AAC ATC AAC AAG TTC TGT GAG AAT CCT GAT GAG GTG AAG CGT GAT<br>Asp Asn Ile Asn Lys Phe Cys Glu Asn Pro Asp Glu Val Lys Arg Asp<br>560                          565                        570 | 1727 |
| GAT CCC AAG TTT TAC GAA TCA AAC ATC ATG AGC ACT ATC AAC GGC TAC<br>Asp Pro Lys Phe Tyr Glu Ser Asn Ile Met Ser Thr Ile Asn Gly Tyr<br>575                          580                        585                        590 | 1775 |
| GTG CCC GAG AGC ATT TCC ACT CTG GGA TTC TGT TTT GAT GAC ACT GTC<br>Val Pro Glu Ser Ile Ser Thr Leu Gly Phe Cys Phe Asp Asp Thr Val<br>                595                        600                        605 | 1823 |
| CAG TGG CAC TTC TGC AGT GTG GGA ACT CAT GAT GAT ATT TTG ACC ATC<br>Gln Trp His Phe Cys Ser Val Gly Thr His Asp Asp Ile Leu Thr Ile<br>          610                          615                        620 | 1871 |
| CAC TTC ACT GGG CAC TCG TTC ATC TAT GGG AGG AGG CAC GAG GAC ACC<br>His Phe Thr Gly His Ser Phe Ile Tyr Gly Arg Arg His Glu Asp Thr<br>625                          630                        635 | 1919 |
| TTG ACC CTG TTC CCC ATG CGT GGT GAA TCT GTG ACA GTT ACA ATG GAT<br>Leu Thr Leu Phe Pro Met Arg Gly Glu Ser Val Thr Val Thr Met Asp<br>640                          645                        650 | 1967 |
| AAT GTT GGA ACT TGG ATG TTG ACC ACC ATG AAT TCC AAT CCA AAA CGC<br>Asn Val Gly Thr Trp Met Leu Thr Thr Met Asn Ser Asn Pro Lys Arg<br>655                          660                        665                        670 | 2015 |

```
AGA AAC CTA AGA CTG AGA TTC AGA GAT GTT AAG TGT AAT CGG GAT TAT    2063
Arg Asn Leu Arg Leu Arg Phe Arg Asp Val Lys Cys Asn Arg Asp Tyr
            675                 680                 685

GAC AAT GAG GAC TCA TAT GAG ATT TAT GAA CCT CCT GCA CCT ACA TCC    2111
Asp Asn Glu Asp Ser Tyr Glu Ile Tyr Glu Pro Pro Ala Pro Thr Ser
            690                 695                 700

ATG ACA ACT CGG AGA ATT CAT GAT TCC TTA GAA AAT GAA TTT GGC ATA    2159
Met Thr Thr Arg Arg Ile His Asp Ser Leu Glu Asn Glu Phe Gly Ile
            705                 710                 715

GAC AAC GAA GAT GAT GAT TAC CAG TAC TTA CTG GCG TCA TCA TTA GGA    2207
Asp Asn Glu Asp Asp Asp Tyr Gln Tyr Leu Leu Ala Ser Ser Leu Gly
            720                 725                 730

ATT AGG TCA TTC AAA AAC TCA TCA TTG AAT CCA GAG GAA AAT GAG TTC    2255
Ile Arg Ser Phe Lys Asn Ser Ser Leu Asn Pro Glu Glu Asn Glu Phe
735                 740                 745                 750

AAT CTC ACT GCT CTC GCT CTG GAG AAC AGC TCT GAG TTC ATA TCT CCA    2303
Asn Leu Thr Ala Leu Ala Leu Glu Asn Ser Ser Glu Phe Ile Ser Pro
            755                 760                 765

AGC ACA GAC AGA GTT GTT GAC TCA AAC TCT TCA CGA ATC CTT AGT AAA    2351
Ser Thr Asp Arg Val Val Asp Ser Asn Ser Ser Arg Ile Leu Ser Lys
            770                 775                 780

ATC ATC AAT AAT AAC CTC AAA GAC TTT CAA AGA ACA CTT CCT GGC TCA    2399
Ile Ile Asn Asn Asn Leu Lys Asp Phe Gln Arg Thr Leu Pro Gly Ser
            785                 790                 795

GGA GCC ACC GTG GCT GGT ACC CTC CTT AGA AAC CTC ATT GGC TTA GAT    2447
Gly Ala Thr Val Ala Gly Thr Leu Leu Arg Asn Leu Ile Gly Leu Asp
            800                 805                 810

GAG AAC TTC GTC CTC AAC TCT TCT ACA GAA CAT CGT TCC AGC TCA TAT    2495
Glu Asn Phe Val Leu Asn Ser Ser Thr Glu His Arg Ser Ser Ser Tyr
815                 820                 825                 830

CAT GAA AAT GAT ATG GAA AAT CCA CAG TCA AAC ATC ACA ATG GTA TAC    2543
His Glu Asn Asp Met Glu Asn Pro Gln Ser Asn Ile Thr Met Val Tyr
            835                 840                 845

CTA CTT CCT CTT GGT CCA AAA GGA TCT GGG AAT CGA GAA CAA GAT AAA    2591
Leu Leu Pro Leu Gly Pro Lys Gly Ser Gly Asn Arg Glu Gln Asp Lys
            850                 855                 860

CCT AAA ACC ATC AAG ACA GGA AGA CCC CAC ATG ATG AAG CAC AGG TTC    2639
Pro Lys Thr Ile Lys Thr Gly Arg Pro His Met Met Lys His Arg Phe
            865                 870                 875

TCC TGG ATG AAA GCG CCA GCT GGT AAA ACT GGG AGG CAT TCA AAC CCA    2687
Ser Trp Met Lys Ala Pro Ala Gly Lys Thr Gly Arg His Ser Asn Pro
            880                 885                 890

AAG AAT TCG TAT TCT GGA ATG AAG TCT GAG GAG GAC ATT CCT AGC GAG    2735
Lys Asn Ser Tyr Ser Gly Met Lys Ser Glu Glu Asp Ile Pro Ser Glu
895                 900                 905                 910

TTG ATA CCC TTA AAG CAA AAG ATC ACT TCC AAA TTT CTG AAT AGA CGA    2783
Leu Ile Pro Leu Lys Gln Lys Ile Thr Ser Lys Phe Leu Asn Arg Arg
            915                 920                 925

TGG CGT GTG GCT TCT GAA AAG GGT AGT TAT GAA ATA ATA GCA GCA AAT    2831
Trp Arg Val Ala Ser Glu Lys Gly Ser Tyr Glu Ile Ile Ala Ala Asn
            930                 935                 940

GGT GAA GAC ACA GAT GTG GAT AAG CTG ACC AAC AGT CCT CAA AAT CAG    2879
Gly Glu Asp Thr Asp Val Asp Lys Leu Thr Asn Ser Pro Gln Asn Gln
            945                 950                 955

AAT ATC ACA GTA CCT CGG GGA GAG AGC ACC TCT CAC ACA AAC ACA ACA    2927
Asn Ile Thr Val Pro Arg Gly Glu Ser Thr Ser His Thr Asn Thr Thr
            960                 965                 970
```

```
AGA AAG CCA AGT GAC CTC CCA ACA TTT TCT GGA GTT GGA CAT AAA TCT    2975
Arg Lys Pro Ser Asp Leu Pro Thr Phe Ser Gly Val Gly His Lys Ser
975             980             985             990

CCA CAT GTA AGA CAG GAG GAA GAA AAC AGT GGT TTT CAG AAA AGA CAG    3023
Pro His Val Arg Gln Glu Glu Glu Asn Ser Gly Phe Gln Lys Arg Gln
        995             1000            1005

TTA TTC ATC AGG ACA CGG AAG AAG AAG AAA AAT AAG AAG CTT GCA CTA    3071
Leu Phe Ile Arg Thr Arg Lys Lys Lys Lys Asn Lys Lys Leu Ala Leu
            1010            1015            1020

CAC AGT CCT CTA TCT CCA AGG GGC TTT GAC CCT TTG AGA GGA CAT AAC    3119
His Ser Pro Leu Ser Pro Arg Gly Phe Asp Pro Leu Arg Gly His Asn
                1025            1030            1035

CAT TCC CCA TTT CCA GAC AGG AGA CTA CTT AAT CAC TCA CTG TTA CTC    3167
His Ser Pro Phe Pro Asp Arg Arg Leu Leu Asn His Ser Leu Leu Leu
1040            1045            1050

CAC AAG TCC AAT GAA ACA GCT CTT TCT CCA GAC CTG AAC CAG ACC TCT    3215
His Lys Ser Asn Glu Thr Ala Leu Ser Pro Asp Leu Asn Gln Thr Ser
1055            1060            1065            1070

CCT TCA ATG AGT ACG GAC AGG TCA CTT CCT GAC TAT AAT CAG TAC TCG    3263
Pro Ser Met Ser Thr Asp Arg Ser Leu Pro Asp Tyr Asn Gln Tyr Ser
            1075            1080            1085

AAA AAT GAC ACT GAG CAG ATG AGC TCT TCT TTA GAT CTT TAT CAG TCA    3311
Lys Asn Asp Thr Glu Gln Met Ser Ser Ser Leu Asp Leu Tyr Gln Ser
                1090            1095            1100

GTG CCC GCA GAG GAA CAC TCT CCA ACA TTT CCT GCC CAA GAT CCT GAT    3359
Val Pro Ala Glu Glu His Ser Pro Thr Phe Pro Ala Gln Asp Pro Asp
        1105            1110            1115

CAA ACA CAC TCT ACC ACA GAT CCT AGC TAC AGA TCC TCT CCG CCA GAG    3407
Gln Thr His Ser Thr Thr Asp Pro Ser Tyr Arg Ser Ser Pro Pro Glu
            1120            1125            1130

CTC AGC CAG GGG CTT GAT TAT GAC CTA AGT CAT GAC TTT TAC CCT GAT    3455
Leu Ser Gln Gly Leu Asp Tyr Asp Leu Ser His Asp Phe Tyr Pro Asp
1135            1140            1145            1150

GAC ATT GGT CTA ACA TCT TTC TTT CCA GAC CAA AGT CAA AAG TCA TCT    3503
Asp Ile Gly Leu Thr Ser Phe Phe Pro Asp Gln Ser Gln Lys Ser Ser
                1155            1160            1165

TTC TCT TCA GAT GAT GAC CAA GCA ATC CCT TCC TCA GAC TTA AGC CTC    3551
Phe Ser Ser Asp Asp Asp Gln Ala Ile Pro Ser Ser Asp Leu Ser Leu
            1170            1175            1180

TTT ACC ATC TCT CCA GAA TTG GAT CAG ACA ATT ATT TAC CCA GAC CTG    3599
Phe Thr Ile Ser Pro Glu Leu Asp Gln Thr Ile Ile Tyr Pro Asp Leu
        1185            1190            1195

GAT CAG TTG CTC CTT TCT CCA GAA GAC AAT CAG AAG ACC TCC TCC CCA    3647
Asp Gln Leu Leu Leu Ser Pro Glu Asp Asn Gln Lys Thr Ser Ser Pro
1200            1205            1210

GAC CTG GGC CAG GTG CCC CTT TCT CCA GAT GAC AAC CAG AAG ACC TCC    3695
Asp Leu Gly Gln Val Pro Leu Ser Pro Asp Asp Asn Gln Lys Thr Ser
1215            1220            1225            1230

TCC CCA GAC CTG GGT CAG GTG TCC CTT TCT CCA GAT GAT AAC CAG AAG    3743
Ser Pro Asp Leu Gly Gln Val Ser Leu Ser Pro Asp Asp Asn Gln Lys
            1235            1240            1245

ACC TCC TCC CCA GAC CTG GGT CAG GTG CCC CTT TCT CTA GAT GAC AAC    3791
Thr Ser Ser Pro Asp Leu Gly Gln Val Pro Leu Ser Leu Asp Asp Asn
                1250            1255            1260

CAG AAG ACG ACC TCC CCA GAC CTG GGT CAG GTG CCC CTT TCT CCA GAT    3839
Gln Lys Thr Thr Ser Pro Asp Leu Gly Gln Val Pro Leu Ser Pro Asp
            1265            1270            1275
```

-continued

```
GAC AAC CAG ATG ATC ACC TCC CCA GAC CTG GGT CAG GTG CCC CTT TCT      3887
Asp Asn Gln Met Ile Thr Ser Pro Asp Leu Gly Gln Val Pro Leu Ser
            1280                1285                1290

TCT GAT AAC CAG AAG ACC TCT TCC CCA GAT CTG GGT CAG GTG CCT CTT      3935
Ser Asp Asn Gln Lys Thr Ser Ser Pro Asp Leu Gly Gln Val Pro Leu
1295                1300                1305                1310

TTT CCT GAA GAC AAC CAG AAT TAC TTC CTA GAC CTG AGT CAG GTA CCT      3983
Phe Pro Glu Asp Asn Gln Asn Tyr Phe Leu Asp Leu Ser Gln Val Pro
                1315                1320                1325

CTC TCC TCA GAC CAA AAC CAG GAG ACC TCC TCC ACA GAC CTA CTG ACT      4031
Leu Ser Ser Asp Gln Asn Gln Glu Thr Ser Ser Thr Asp Leu Leu Thr
            1330                1335                1340

CTC TCT CCT GAT TTT GGT CAG ACA GTC CTT TCC CCA GAC TTG GAT CAG      4079
Leu Ser Pro Asp Phe Gly Gln Thr Val Leu Ser Pro Asp Leu Asp Gln
        1345                1350                1355

CTG CCA CTC CCT TCA GAC AAT AGT CAG GTG ACC GTT TCC CCA GAC CTC      4127
Leu Pro Leu Pro Ser Asp Asn Ser Gln Val Thr Val Ser Pro Asp Leu
    1360                1365                1370

AGC CTC TTG ACC CTC TCA CCA GAT TTT AAT GAG ATA ATC CTA GCC CCA      4175
Ser Leu Leu Thr Leu Ser Pro Asp Phe Asn Glu Ile Ile Leu Ala Pro
1375                1380                1385                1390

GAC CTT GGT CAA GTG ACC CTC TCT CCA GAC CTC ATC CAG ACA AAC CCT      4223
Asp Leu Gly Gln Val Thr Leu Ser Pro Asp Leu Ile Gln Thr Asn Pro
                1395                1400                1405

GCT CTT AAT CAT GGA CAC AAA GCA TCC TCT GCA GAC CCT GAT CAA GCA      4271
Ala Leu Asn His Gly His Lys Ala Ser Ser Ala Asp Pro Asp Gln Ala
            1410                1415                1420

TCC TAC CCT CCA GAT TCT GGT CAG GCT TCA TCG CTT CCA GAA CTG AAT      4319
Ser Tyr Pro Pro Asp Ser Gly Gln Ala Ser Ser Leu Pro Glu Leu Asn
        1425                1430                1435

CGG ACT CTT CCT CAT CCA GAT CTC ACT CAC ATA CCA CCT CCT TCA CCA      4367
Arg Thr Leu Pro His Pro Asp Leu Thr His Ile Pro Pro Pro Ser Pro
    1440                1445                1450

TCT CCC ACA CTC AAT AAC ACT TCT TTG TCA AGG AAA TTT AAC CCT CTT      4415
Ser Pro Thr Leu Asn Asn Thr Ser Leu Ser Arg Lys Phe Asn Pro Leu
1455                1460                1465                1470

GTT GTA GTA GGT CTC AGT AGA GTA GAT GGA GAC GAC GTT GAG ATT GTT      4463
Val Val Val Gly Leu Ser Arg Val Asp Gly Asp Asp Val Glu Ile Val
                1475                1480                1485

CCA AGT GAG GAG CCA GAG AGA ATA GAT GAA GAT TAT GCC GAG GAT GAC      4511
Pro Ser Glu Glu Pro Glu Arg Ile Asp Glu Asp Tyr Ala Glu Asp Asp
            1490                1495                1500

TTT GTA ACC TAT AAT GAC CCC TAC AGA ACA GAC ACT AGG ACA GAT GTC      4559
Phe Val Thr Tyr Asn Asp Pro Tyr Arg Thr Asp Thr Arg Thr Asp Val
        1505                1510                1515

AAT TCC TCC AGA AAT CCT GAC ACT ATC GCA GCA TGG TAC CTC CGA GGC      4607
Asn Ser Ser Arg Asn Pro Asp Thr Ile Ala Ala Trp Tyr Leu Arg Gly
    1520                1525                1530

CAC GGT GGA CAC AAA AAA TTC TAC TAT ATT GCA GCT GAA GAA ATA ACC      4655
His Gly Gly His Lys Lys Phe Tyr Tyr Ile Ala Ala Glu Glu Ile Thr
1535                1540                1545                1550

TGG AAT TAC GCA GAG TTT GCA CAA AGT GAA ATG GAC CAT GAA GAC ACA      4703
Trp Asn Tyr Ala Glu Phe Ala Gln Ser Glu Met Asp His Glu Asp Thr
                1555                1560                1565

GGC CAC ACT CCA AAG GAC ACC ACA TAC AAG AAA GTC GTT TTC AGA AAA      4751
Gly His Thr Pro Lys Asp Thr Thr Tyr Lys Lys Val Val Phe Arg Lys
            1570                1575                1580
```

-continued

```
TAC CTT GAT AGC ACG TTT ACA AGT CGT GAT CCT CGG GCA GAA TAT GAG          4799
Tyr Leu Asp Ser Thr Phe Thr Ser Arg Asp Pro Arg Ala Glu Tyr Glu
            1585                1590                1595

GAG CAC CTT GGC ATT CTC GGT CCT GTG ATC CGG GCT GAA GTG GAT GAT          4847
Glu His Leu Gly Ile Leu Gly Pro Val Ile Arg Ala Glu Val Asp Asp
1600                1605                1610

GTG ATC CAA GTT CGA TTT AAA AAT TTG GCA TCC AGA CCG TAT TCT CTT          4895
Val Ile Gln Val Arg Phe Lys Asn Leu Ala Ser Arg Pro Tyr Ser Leu
1615                1620                1625                1630

CAT GCT CAC GGA CTT TCC TAT GAA AAA TCC TCA GAG GGG AAG ACT TAT          4943
His Ala His Gly Leu Ser Tyr Glu Lys Ser Ser Glu Gly Lys Thr Tyr
            1635                1640                1645

GAA GAT GAA TCT CCT GAA TGG TTT CAG GAA GAT GAT GCT GTC CAG CCC          4991
Glu Asp Glu Ser Pro Glu Trp Phe Gln Glu Asp Asp Ala Val Gln Pro
            1650                1655                1660

AAT AGC AGT TAC ACC TAT GTA TGG CAT GCC ACC AAG CGC TCA GGG CCA          5039
Asn Ser Ser Tyr Thr Tyr Val Trp His Ala Thr Lys Arg Ser Gly Pro
            1665                1670                1675

GAG AAC CCT GGT TCT GCC TGC CGG GCT TGG GCC TAC TAT TCT GCA GTG          5087
Glu Asn Pro Gly Ser Ala Cys Arg Ala Trp Ala Tyr Tyr Ser Ala Val
            1680                1685                1690

AAT GTG GAG AGG GAC ATC CAC TCA GGC TTG ATC GGC CCC CTT CTG ATC          5135
Asn Val Glu Arg Asp Ile His Ser Gly Leu Ile Gly Pro Leu Leu Ile
1695                1700                1705                1710

TGC CGG AAA GGA ACA CTT CAC ATG GAG CGC AAC CTG CCT ATG GAC ATG          5183
Cys Arg Lys Gly Thr Leu His Met Glu Arg Asn Leu Pro Met Asp Met
            1715                1720                1725

AGA GAG TTT GTC TTA CTC TTC ATG GTC TTT GAT GAG AAG AAG AGC TGG          5231
Arg Glu Phe Val Leu Leu Phe Met Val Phe Asp Glu Lys Lys Ser Trp
            1730                1735                1740

TAC TAT GAA AAG TCC AAG GGG TCA CGG AGA ATT GAA TCC CCA GAA GAG          5279
Tyr Tyr Glu Lys Ser Lys Gly Ser Arg Arg Ile Glu Ser Pro Glu Glu
            1745                1750                1755

AAA AAT GCC CAC AAG TTT TAC GCA ATT AAT GGG ATG ATC TAC AAC CTG          5327
Lys Asn Ala His Lys Phe Tyr Ala Ile Asn Gly Met Ile Tyr Asn Leu
            1760                1765                1770

CCC GGC CTG AGA ATG TAC GAG CAA GAG TGG GTG AGG CTA CAC CTG CTG          5375
Pro Gly Leu Arg Met Tyr Glu Gln Glu Trp Val Arg Leu His Leu Leu
1775                1780                1785                1790

AAC ATG GGC GGC TCC CGA GAT ATT CAC GTG GTT CAC TTC CAT GGC CAG          5423
Asn Met Gly Gly Ser Arg Asp Ile His Val Val His Phe His Gly Gln
            1795                1800                1805

ACC CTG CTG GAT AAT AGG ACC AAA CAG CAC CAG TTA GGC GTC TGG CCC          5471
Thr Leu Leu Asp Asn Arg Thr Lys Gln His Gln Leu Gly Val Trp Pro
            1810                1815                1820

CTT CTG CCT GGT TCA TTT AAA ACT CTT GAA ATG AAG GCA TCC AAG CCT          5519
Leu Leu Pro Gly Ser Phe Lys Thr Leu Glu Met Lys Ala Ser Lys Pro
            1825                1830                1835

GGC TGG TGG CTC CTA GAC ACA GAG GTT GGA GAA AAC CAG GTA GCT GGC          5567
Gly Trp Trp Leu Leu Asp Thr Glu Val Gly Glu Asn Gln Val Ala Gly
            1840                1845                1850

ATG CAA ACG CCA TTT CTC ATC ATA GAC AAA GAG TGT AAG ATG CCA ATG          5615
Met Gln Thr Pro Phe Leu Ile Ile Asp Lys Glu Cys Lys Met Pro Met
1855                1860                1865                1870

GGA CTA AGC ACT GGT GTC ATA TCT GAT TCA CAG ATC AAG GCT TCG GAA          5663
Gly Leu Ser Thr Gly Val Ile Ser Asp Ser Gln Ile Lys Ala Ser Glu
            1875                1880                1885
```

-continued

| | |
|---|---|
| TAT CTG ACT TAT TGG GAG CCC AGA TTA GCA CGA TTA AAC AAT GCT GGT<br>Tyr Leu Thr Tyr Trp Glu Pro Arg Leu Ala Arg Leu Asn Asn Ala Gly<br>              1890                    1895                   1900 | 5711 |
| TCA TAC AAT GCT TGG AGT ATA GAA AAA ACT GCA TTA GAT TTT CCC ATT<br>Ser Tyr Asn Ala Trp Ser Ile Glu Lys Thr Ala Leu Asp Phe Pro Ile<br>      1905                 1910                   1915 | 5759 |
| AAA CCT TGG ATC CAG GTG GAC ATG CAG AAG GAA GTT GTA GTC ACC GGG<br>Lys Pro Trp Ile Gln Val Asp Met Gln Lys Glu Val Val Val Thr Gly<br>1920                  1925                   1930 | 5807 |
| ATA CAA ACC CAA GGT GCT AAA CAC TAC CTA AAG TCC TGC TTT ACC ACG<br>Ile Gln Thr Gln Gly Ala Lys His Tyr Leu Lys Ser Cys Phe Thr Thr<br>1935                  1940                   1945               1950 | 5855 |
| GAG TTC CAA GTG GCT TAC AGC TCT GAC CAA ACC AAC TGG CAG ATC TTC<br>Glu Phe Gln Val Ala Tyr Ser Ser Asp Gln Thr Asn Trp Gln Ile Phe<br>              1955                   1960                 1965 | 5903 |
| AGA GGG AAG AGC GGG AAG AGC GTG ATG TAT TTT ACT GGT AAT TCA GAT<br>Arg Gly Lys Ser Gly Lys Ser Val Met Tyr Phe Thr Gly Asn Ser Asp<br>              1970                   1975                 1980 | 5951 |
| GGC TCT ACA ATA AAA GAG AAT CGA CTT GAC CCA CCC ATT GTG GCT AGA<br>Gly Ser Thr Ile Lys Glu Asn Arg Leu Asp Pro Pro Ile Val Ala Arg<br>               1985                  1990                 1995 | 5999 |
| TAC ATT AGG ATA CAC CCA ACA AAA TCC TAT AAT AGA CCC ACC CTT CGG<br>Tyr Ile Arg Ile His Pro Thr Lys Ser Tyr Asn Arg Pro Thr Leu Arg<br>2000                  2005                   2010 | 6047 |
| CTG GAG CTG CAG GGC TGT GAG GTG AAC GGA TGT TCC ACA CCA CTG GGC<br>Leu Glu Leu Gln Gly Cys Glu Val Asn Gly Cys Ser Thr Pro Leu Gly<br>2015                  2020                   2025                 2030 | 6095 |
| CTG GAA GAT GGA CGG ATT CAA GAC AAG CAA ATT ACT GCA TCT TCA TTT<br>Leu Glu Asp Gly Arg Ile Gln Asp Lys Gln Ile Thr Ala Ser Ser Phe<br>               2035                  2040                 2045 | 6143 |
| AAA AAG TCG TGG TGG GGA GAC TAC TGG GAG CCC TCC CTT GCC CGC CTG<br>Lys Lys Ser Trp Trp Gly Asp Tyr Trp Glu Pro Ser Leu Ala Arg Leu<br>              2050                  2055                 2060 | 6191 |
| AAC GCC CAG GGC CGC GTG AAC GCC TGG CAA GCC AAG GCA AAC AAC AAC<br>Asn Ala Gln Gly Arg Val Asn Ala Trp Gln Ala Lys Ala Asn Asn Asn<br>            2065                   2070                 2075 | 6239 |
| AAG CAG TGG TTA CAA GTC GAT CTG CTC AAA ATC AAG AAG GTA ACG GCC<br>Lys Gln Trp Leu Gln Val Asp Leu Leu Lys Ile Lys Lys Val Thr Ala<br>2080                  2085                   2090 | 6287 |
| ATC GTA ACG CAG GGC TGT AAG TCT CTG TCC TCT GAG ATG TAC GTG AAG<br>Ile Val Thr Gln Gly Cys Lys Ser Leu Ser Ser Glu Met Tyr Val Lys<br>2095                  2100                   2105                 2110 | 6335 |
| AGC TAC AGC ATC CAG TAC AGT GAC CAG GGT GTG GCA TGG AAA CCT TAC<br>Ser Tyr Ser Ile Gln Tyr Ser Asp Gln Gly Val Ala Trp Lys Pro Tyr<br>               2115                  2120                 2125 | 6383 |
| CGA CAG AAA TCC TCC ATG GTG GAC AAG ATT TTT GAA GGA AAC AGC AAT<br>Arg Gln Lys Ser Ser Met Val Asp Lys Ile Phe Glu Gly Asn Ser Asn<br>            2130                   2135                 2140 | 6431 |
| ACC AAG GGG CAC ATG AAG AAC TTT TTC AAC CCG CCC ATT ATT TCC AGA<br>Thr Lys Gly His Met Lys Asn Phe Phe Asn Pro Pro Ile Ile Ser Arg<br>              2145                  2150                 2155 | 6479 |
| TTT ATC CGC ATC ATT CCT AAA ACA TGG AAC CAG AGC ATC GCC CTT CGC<br>Phe Ile Arg Ile Ile Pro Lys Thr Trp Asn Gln Ser Ile Ala Leu Arg<br>            2160                   2165                 2170 | 6527 |
| CTA GAG CTC TTC GGC TGT GAC ATT TAT TAGAATTAAA TTCCAAAAAA<br>Leu Glu Leu Phe Gly Cys Asp Ile Tyr<br>2175                  2180 | 6574 |
| AAAAAAAAAA A | 6585 |

-continued (2) INFORMATION FOR SEQ ID NO:5:

(i) SEQUENCE CHARACTERISTICS:
        (A) LENGTH: 2183 amino acids
        (B) TYPE: amino acid
        (D) TOPOLOGY: linear (ii) MOLECULE TYPE: protein (xi) SEQUENCE DESCRIPTION: SEQ ID NO:5:

```
Met Leu Leu Val Cys Pro Cys Phe Phe Leu Val Val Leu Gly Thr
 1               5                  10                  15

Arg Trp Ala Gly Trp Gly Ser His Gln Ala Glu Ala Ala Gln Leu Arg
                 20                  25                  30

Gln Phe Tyr Val Ala Ala Gln Gly Ile Leu Trp Asn Tyr His Pro Glu
             35                  40                  45

Pro Thr Asp Pro Ser Leu Asn Ser Ile Pro Ser Phe Lys Lys Ile Val
         50                  55                  60

Tyr Arg Glu Tyr Glu Gln Tyr Phe Lys Lys Glu Lys Pro Arg Ser Ser
 65                  70                  75                  80

Asn Ser Gly Leu Leu Gly Pro Thr Leu Tyr Ala Glu Val Gly Asp Val
                 85                  90                  95

Ile Lys Val His Phe Arg Asn Lys Ala Asp Lys Pro Leu Ser Ile His
            100                 105                 110

Pro Gln Gly Ile Lys Tyr Ser Lys Phe Ser Glu Gly Ala Ser Tyr Ala
        115                 120                 125

Asp His Thr Phe Pro Ala Glu Arg Lys Asp Asp Ala Val Ala Pro Gly
    130                 135                 140

Glu Glu Tyr Thr Tyr Glu Trp Ile Val Ser Glu Asp Ser Gly Pro Thr
145                 150                 155                 160

Pro Asp Asp Pro Pro Cys Leu Thr His Ile Tyr Tyr Ser Tyr Glu Asn
                165                 170                 175

Leu Thr Gln Asp Phe Asn Ser Gly Leu Ile Gly Pro Leu Leu Ile Cys
            180                 185                 190

Lys Lys Gly Thr Leu Thr Glu Asp Gly Thr Gln Lys Met Phe Asp Lys
        195                 200                 205

Gln His Val Leu Leu Phe Ala Val Phe Asp Glu Ser Lys Ser Arg Ser
    210                 215                 220

Gln Ser Pro Ser Leu Met Tyr Thr Ile Asn Gly Phe Val Asn Lys Thr
225                 230                 235                 240

Met Pro Asp Ile Thr Val Cys Ala His Asp His Val Ser Trp His Leu
                245                 250                 255

Ile Gly Met Ser Ser Gly Pro Glu Leu Phe Ser Ile His Phe Asn Gly
            260                 265                 270

Gln Val Leu Glu Gln Asn Gln His Lys Val Ser Thr Val Thr Leu Val
        275                 280                 285

Ser Ala Thr Ser Thr Thr Ala Asn Met Thr Met Ser Pro Glu Gly Arg
    290                 295                 300

Trp Ile Val Ser Ser Leu Ile Pro Lys His Tyr Gln Ala Gly Met Gln
305                 310                 315                 320

Ala Tyr Ile Asp Ile Lys Asn Cys Pro Lys Lys Thr Arg Ser Pro Lys
                325                 330                 335

Thr Leu Thr Arg Glu Gln Arg Arg Tyr Met Lys Arg Trp Glu Tyr Phe
            340                 345                 350
```

```
Ile Ala Ala Glu Glu Val Ile Trp Asn Tyr Ala Pro Val Ile Pro Ala
            355                 360                 365

Asn Met Asp Lys Ile Tyr Arg Ser Gln His Leu Asp Asn Phe Ser Asn
        370                 375                 380

Gln Ile Gly Lys His Tyr Lys Lys Val Ile Tyr Arg Gln Tyr Glu Glu
385                 390                 395                 400

Glu Thr Phe Thr Lys Arg Thr Asp Asn Pro Ser Ile Lys Gln Ser Gly
                405                 410                 415

Ile Leu Gly Pro Val Ile Arg Ala Gln Val Arg Asp Thr Leu Lys Ile
                420                 425                 430

Val Phe Lys Asn Met Ala Ser Arg Pro Tyr Ser Ile Tyr Pro His Gly
            435                 440                 445

Val Thr Phe Ser Pro Tyr Glu Asp Gly Ile Asn Ser Ser Thr Ser
        450                 455                 460

Gly Ser His Thr Thr Ile Arg Pro Val Gln Pro Gly Glu Thr Phe Thr
465                 470                 475                 480

Tyr Lys Trp Asn Ile Leu Glu Phe Asp Glu Pro Thr Glu Asn Asp Ala
                485                 490                 495

Gln Cys Leu Thr Arg Pro Tyr Tyr Ser Asp Val Asp Val Thr Arg Asp
                500                 505                 510

Ile Ala Ser Gly Leu Ile Gly Leu Leu Leu Ile Cys Lys Ser Arg Ser
            515                 520                 525

Leu Asp Gln Arg Gly Val Gln Arg Val Ala Asp Ile Glu Gln Gln Ala
        530                 535                 540

Val Phe Ala Val Phe Asp Glu Asn Lys Ser Trp Tyr Ile Glu Asp Asn
545                 550                 555                 560

Ile Asn Lys Phe Cys Glu Asn Pro Asp Glu Val Lys Arg Asp Asp Pro
                565                 570                 575

Lys Phe Tyr Glu Ser Asn Ile Met Ser Thr Ile Asn Gly Tyr Val Pro
                580                 585                 590

Glu Ser Ile Ser Thr Leu Gly Phe Cys Phe Asp Asp Thr Val Gln Trp
            595                 600                 605

His Phe Cys Ser Val Gly Thr His Asp Asp Ile Leu Thr Ile His Phe
        610                 615                 620

Thr Gly His Ser Phe Ile Tyr Gly Arg Arg His Glu Asp Thr Leu Thr
625                 630                 635                 640

Leu Phe Pro Met Arg Gly Glu Ser Val Thr Val Thr Met Asp Asn Val
                645                 650                 655

Gly Thr Trp Met Leu Thr Thr Met Asn Ser Asn Pro Lys Arg Arg Asn
                660                 665                 670

Leu Arg Leu Arg Phe Arg Asp Val Lys Cys Asn Arg Asp Tyr Asp Asn
            675                 680                 685

Glu Asp Ser Tyr Glu Ile Tyr Glu Pro Pro Ala Pro Thr Ser Met Thr
        690                 695                 700

Thr Arg Arg Ile His Asp Ser Leu Glu Asn Glu Phe Gly Ile Asp Asn
705                 710                 715                 720

Glu Asp Asp Asp Tyr Gln Tyr Leu Leu Ala Ser Ser Leu Gly Ile Arg
                725                 730                 735

Ser Phe Lys Asn Ser Ser Leu Asn Pro Glu Glu Asn Glu Phe Asn Leu
            740                 745                 750

Thr Ala Leu Ala Leu Glu Asn Ser Ser Glu Phe Ile Ser Pro Ser Thr
        755                 760                 765
```

```
Asp Arg Val Val Asp Ser Asn Ser Ser Arg Ile Leu Ser Lys Ile Ile
    770             775                 780

Asn Asn Asn Leu Lys Asp Phe Gln Arg Thr Leu Pro Gly Ser Gly Ala
785             790                 795                 800

Thr Val Ala Gly Thr Leu Leu Arg Asn Leu Ile Gly Leu Asp Glu Asn
                805                 810                 815

Phe Val Leu Asn Ser Ser Thr Glu His Arg Ser Ser Tyr His Glu
            820                 825                 830

Asn Asp Met Glu Asn Pro Gln Ser Asn Ile Thr Met Val Tyr Leu Leu
            835                 840                 845

Pro Leu Gly Pro Lys Gly Ser Gly Asn Arg Glu Gln Asp Lys Pro Lys
            850                 855                 860

Thr Ile Lys Thr Gly Arg Pro His Met Met Lys His Arg Phe Ser Trp
865             870                 875                 880

Met Lys Ala Pro Ala Gly Lys Thr Gly Arg His Ser Asn Pro Lys Asn
                885                 890                 895

Ser Tyr Ser Gly Met Lys Ser Glu Glu Asp Ile Pro Ser Glu Leu Ile
                900                 905                 910

Pro Leu Lys Gln Lys Ile Thr Ser Lys Phe Leu Asn Arg Arg Trp Arg
            915                 920                 925

Val Ala Ser Glu Lys Gly Ser Tyr Glu Ile Ile Ala Ala Asn Gly Glu
            930                 935                 940

Asp Thr Asp Val Asp Lys Leu Thr Asn Ser Pro Gln Asn Gln Asn Ile
945             950                 955                 960

Thr Val Pro Arg Gly Glu Ser Thr Ser His Thr Asn Thr Thr Arg Lys
                965                 970                 975

Pro Ser Asp Leu Pro Thr Phe Ser Gly Val Gly His Lys Ser Pro His
            980                 985                 990

Val Arg Gln Glu Glu Asn Ser Gly Phe Gln Lys Arg Gln Leu Phe
            995                 1000                1005

Ile Arg Thr Arg Lys Lys Lys Asn Lys Lys Leu Ala Leu His Ser
    1010                1015                1020

Pro Leu Ser Pro Arg Gly Phe Asp Pro Leu Arg Gly His Asn His Ser
1025                1030                1035                1040

Pro Phe Pro Asp Arg Arg Leu Leu Asn His Ser Leu Leu Leu His Lys
                1045                1050                1055

Ser Asn Glu Thr Ala Leu Ser Pro Asp Leu Asn Gln Thr Ser Pro Ser
                1060                1065                1070

Met Ser Thr Asp Arg Ser Leu Pro Asp Tyr Asn Gln Tyr Ser Lys Asn
            1075                1080                1085

Asp Thr Glu Gln Met Ser Ser Leu Asp Leu Tyr Gln Ser Val Pro
    1090                1095                1100

Ala Glu Glu His Ser Pro Thr Phe Pro Ala Gln Asp Pro Asp Gln Thr
1105                1110                1115                1120

His Ser Thr Thr Asp Pro Ser Tyr Arg Ser Ser Pro Pro Glu Leu Ser
                1125                1130                1135

Gln Gly Leu Asp Tyr Asp Leu Ser His Asp Phe Tyr Pro Asp Asp Ile
            1140                1145                1150

Gly Leu Thr Ser Phe Phe Pro Asp Gln Ser Gln Lys Ser Ser Phe Ser
            1155                1160                1165

Ser Asp Asp Asp Gln Ala Ile Pro Ser Ser Asp Leu Ser Leu Phe Thr
    1170                1175                1180
```

-continued

```
Ile Ser Pro Glu Leu Asp Gln Thr Ile Ile Tyr Pro Asp Leu Asp Gln
1185                1190                1195                1200

Leu Leu Leu Ser Pro Glu Asp Asn Gln Lys Thr Ser Ser Pro Asp Leu
                1205                1210                1215

Gly Gln Val Pro Leu Ser Pro Asp Asp Asn Gln Lys Thr Ser Ser Pro
                1220                1225                1230

Asp Leu Gly Gln Val Ser Leu Ser Pro Asp Asp Asn Gln Lys Thr Ser
                1235                1240                1245

Ser Pro Asp Leu Gly Gln Val Pro Leu Ser Leu Asp Asp Asn Gln Lys
                1250                1255                1260

Thr Thr Ser Pro Asp Leu Gly Gln Val Pro Leu Ser Pro Asp Asp Asn
1265                1270                1275                1280

Gln Met Ile Thr Ser Pro Asp Leu Gly Gln Val Pro Leu Ser Ser Asp
                1285                1290                1295

Asn Gln Lys Thr Ser Ser Pro Asp Leu Gly Gln Val Pro Leu Phe Pro
                1300                1305                1310

Glu Asp Asn Gln Asn Tyr Phe Leu Asp Leu Ser Gln Val Pro Leu Ser
                1315                1320                1325

Ser Asp Gln Asn Gln Glu Thr Ser Ser Thr Asp Leu Leu Thr Leu Ser
                1330                1335                1340

Pro Asp Phe Gly Gln Thr Val Leu Ser Pro Asp Leu Asp Gln Leu Pro
1345                1350                1355                1360

Leu Pro Ser Asp Asn Ser Gln Val Thr Val Ser Pro Asp Leu Ser Leu
                1365                1370                1375

Leu Thr Leu Ser Pro Asp Phe Asn Glu Ile Ile Leu Ala Pro Asp Leu
                1380                1385                1390

Gly Gln Val Thr Leu Ser Pro Asp Leu Ile Gln Thr Asn Pro Ala Leu
                1395                1400                1405

Asn His Gly His Lys Ala Ser Ser Ala Asp Pro Asp Gln Ala Ser Tyr
                1410                1415                1420

Pro Pro Asp Ser Gly Gln Ala Ser Ser Leu Pro Glu Leu Asn Arg Thr
1425                1430                1435                1440

Leu Pro His Pro Asp Leu Thr His Ile Pro Pro Ser Pro Ser Pro
                1445                1450                1455

Thr Leu Asn Asn Thr Ser Leu Ser Arg Lys Phe Asn Pro Leu Val Val
                1460                1465                1470

Val Gly Leu Ser Arg Val Asp Gly Asp Asp Val Glu Ile Val Pro Ser
                1475                1480                1485

Glu Glu Pro Glu Arg Ile Asp Glu Asp Tyr Ala Glu Asp Asp Phe Val
                1490                1495                1500

Thr Tyr Asn Asp Pro Tyr Arg Thr Asp Thr Arg Thr Asp Val Asn Ser
1505                1510                1515                1520

Ser Arg Asn Pro Asp Thr Ile Ala Ala Trp Tyr Leu Arg Gly His Gly
                1525                1530                1535

Gly His Lys Lys Phe Tyr Tyr Ile Ala Ala Glu Glu Ile Thr Trp Asn
                1540                1545                1550

Tyr Ala Glu Phe Ala Gln Ser Glu Met Asp His Glu Asp Thr Gly His
                1555                1560                1565

Thr Pro Lys Asp Thr Thr Tyr Lys Lys Val Val Phe Arg Lys Tyr Leu
                1570                1575                1580

Asp Ser Thr Phe Thr Ser Arg Asp Pro Arg Ala Glu Tyr Glu Glu His
1585                1590                1595                1600
```

```
Leu Gly Ile Leu Gly Pro Val Ile Arg Ala Glu Val Asp Asp Val Ile
            1605                1610                1615

Gln Val Arg Phe Lys Asn Leu Ala Ser Arg Pro Tyr Ser Leu His Ala
        1620                1625                1630

His Gly Leu Ser Tyr Glu Lys Ser Ser Glu Gly Lys Thr Tyr Glu Asp
            1635                1640                1645

Glu Ser Pro Glu Trp Phe Gln Glu Asp Asp Ala Val Gln Pro Asn Ser
        1650                1655                1660

Ser Tyr Thr Tyr Val Trp His Ala Thr Lys Arg Ser Gly Pro Glu Asn
1665                1670                1675                1680

Pro Gly Ser Ala Cys Arg Ala Trp Ala Tyr Tyr Ser Ala Val Asn Val
            1685                1690                1695

Glu Arg Asp Ile His Ser Gly Leu Ile Gly Pro Leu Leu Ile Cys Arg
        1700                1705                1710

Lys Gly Thr Leu His Met Glu Arg Asn Leu Pro Met Asp Met Arg Glu
            1715                1720                1725

Phe Val Leu Leu Phe Met Val Phe Asp Glu Lys Lys Ser Trp Tyr Tyr
        1730                1735                1740

Glu Lys Ser Lys Gly Ser Arg Arg Ile Glu Ser Pro Glu Glu Lys Asn
1745                1750                1755                1760

Ala His Lys Phe Tyr Ala Ile Asn Gly Met Ile Tyr Asn Leu Pro Gly
            1765                1770                1775

Leu Arg Met Tyr Glu Gln Glu Trp Val Arg Leu His Leu Leu Asn Met
        1780                1785                1790

Gly Gly Ser Arg Asp Ile His Val Val His Phe His Gly Gln Thr Leu
            1795                1800                1805

Leu Asp Asn Arg Thr Lys Gln His Gln Leu Gly Val Trp Pro Leu Leu
        1810                1815                1820

Pro Gly Ser Phe Lys Thr Leu Glu Met Lys Ala Ser Lys Pro Gly Trp
1825                1830                1835                1840

Trp Leu Leu Asp Thr Glu Val Gly Glu Asn Gln Val Ala Gly Met Gln
            1845                1850                1855

Thr Pro Phe Leu Ile Ile Asp Lys Glu Cys Lys Met Pro Met Gly Leu
        1860                1865                1870

Ser Thr Gly Val Ile Ser Asp Ser Gln Ile Lys Ala Ser Glu Tyr Leu
            1875                1880                1885

Thr Tyr Trp Glu Pro Arg Leu Ala Arg Leu Asn Asn Ala Gly Ser Tyr
        1890                1895                1900

Asn Ala Trp Ser Ile Glu Lys Thr Ala Leu Asp Phe Pro Ile Lys Pro
1905                1910                1915                1920

Trp Ile Gln Val Asp Met Gln Lys Glu Val Val Val Thr Gly Ile Gln
            1925                1930                1935

Thr Gln Gly Ala Lys His Tyr Leu Lys Ser Cys Phe Thr Thr Glu Phe
        1940                1945                1950

Gln Val Ala Tyr Ser Ser Asp Gln Thr Asn Trp Gln Ile Phe Arg Gly
            1955                1960                1965

Lys Ser Gly Lys Ser Val Met Tyr Phe Thr Gly Asn Ser Asp Gly Ser
        1970                1975                1980

Thr Ile Lys Glu Asn Arg Leu Asp Pro Pro Ile Val Ala Arg Tyr Ile
1985                1990                1995                2000

Arg Ile His Pro Thr Lys Ser Tyr Asn Arg Pro Thr Leu Arg Leu Glu
            2005                2010                2015
```

```
Leu Gln Gly Cys Glu Val Asn Gly Cys Ser Thr Pro Leu Gly Leu Glu
            2020                2025                2030

Asp Gly Arg Ile Gln Asp Lys Gln Ile Thr Ala Ser Ser Phe Lys Lys
        2035                2040                2045

Ser Trp Trp Gly Asp Tyr Trp Glu Pro Ser Leu Ala Arg Leu Asn Ala
2050                2055                2060

Gln Gly Arg Val Asn Ala Trp Gln Ala Lys Ala Asn Asn Asn Lys Gln
2065                2070                2075                2080

Trp Leu Gln Val Asp Leu Leu Lys Ile Lys Lys Val Thr Ala Ile Val
                2085                2090                2095

Thr Gln Gly Cys Lys Ser Leu Ser Ser Glu Met Tyr Val Lys Ser Tyr
            2100                2105                2110

Ser Ile Gln Tyr Ser Asp Gln Gly Val Ala Trp Lys Pro Tyr Arg Gln
        2115                2120                2125

Lys Ser Ser Met Val Asp Lys Ile Phe Glu Gly Asn Ser Asn Thr Lys
        2130                2135                2140

Gly His Met Lys Asn Phe Phe Asn Pro Pro Ile Ile Ser Arg Phe Ile
2145                2150                2155                2160

Arg Ile Ile Pro Lys Thr Trp Asn Gln Ser Ile Ala Leu Arg Leu Glu
                2165                2170                2175

Leu Phe Gly Cys Asp Ile Tyr
            2180

(2) INFORMATION FOR SEQ ID NO:6:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:6:

Ile Asp Ile Lys Asn Cys Pro Lys Lys Thr Arg Asn Leu Lys Lys Ile
1               5                   10                  15

Thr Arg Glu Gln Arg
            20

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:7:

Ile Asp Ile Lys Asn Cys Ala Lys Lys Thr Arg Asn Pro Lys Lys Leu
1               5                   10                  15

Thr Arg Asp Gln Arg
            20

(2) INFORMATION FOR SEQ ID NO:8:

(i) SEQUENCE CHARACTERISTICS:
        (A) LENGTH: 21 amino acids
        (B) TYPE: amino acid
```

-continued (C) STRANDEDNESS: Not Relevant
        (D) TOPOLOGY: Not Relevant (ii) MOLECULE TYPE: protein (xi) SEQUENCE DESCRIPTION: SEQ ID NO:8:

Ile Asp Ile Lys Asn Cys Pro Lys Lys Thr Arg Ser Pro Lys Thr Leu
1               5                   10                  15

Thr Arg Glu Gln Arg
            20

(2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:9:

Leu Ile Cys Lys Ser Arg Ser Leu Asp Arg Arg Gly Ile Gln Arg Ala
1               5                   10                  15

Ala Asp Ile Glu Gln
            20

(2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:10:

Leu Ile Cys Lys Ser Arg Ser Leu Asp Arg Arg Gly Ile Gln Arg Ala
1               5                   10                  15

Ala Asp Ile Glu Gln
            20

(2) INFORMATION FOR SEQ ID NO:11:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:11:

Leu Ile Cys Lys Ser Glu Ser Leu Asp Gln Arg Gly Val Gln Arg Val
1               5                   10                  15

Ala Asp Ile Glu Gln
            20

(2) INFORMATION FOR SEQ ID NO:12:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:12:

Leu Ile Cys Tyr Lys Glu Ser Val Asp Gln Arg Gly Asn Gln Ile Met
1               5                   10                  15

Ser Asp Lys Arg Asn
            20

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:13:

Leu Ile Cys Tyr Lys Glu Ser Val Asp Gln Arg Gly Asn Gln Met Met
1               5                   10                  15

Ser Asp Lys Arg Asn
            20

(2) INFORMATION FOR SEQ ID NO:14:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:14:

Glu Pro Pro Glu Ser Arg Val Met Ala Thr Arg Lys Met His Asp Glu
1               5                   10                  15

Leu Glu Pro Glu Asp
            20

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:15:

Glu Pro Ser Gly Ser Thr Ala Met Thr Thr Lys Lys Ile His Asp Ser
1               5                   10                  15

Ser Glu Ile Glu Asp
            20

(2) INFORMATION FOR SEQ ID NO:16:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:16:

Glu Pro Pro Ala Pro Thr Ser Met Thr Thr Arg Arg Ile His Asp Ser
1               5                  10                  15

Leu Glu Asn Glu Phe
            20

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:17:

Gln Asn Arg Leu Ala Ala Ala Leu Gly Ile Arg Ser Phe Arg Asn Ser
1               5                  10                  15

Ser Leu Asn Gln Glu
            20

(2) INFORMATION FOR SEQ ID NO:18:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:18:

Gln Asp Glu Leu Ala Leu Ile Leu Gly Leu Arg Ser Phe Arg Asn Ser
1               5                  10                  15

Ser Leu Asn Gln Glu
            20

(2) INFORMATION FOR SEQ ID NO:19:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:19:

Gln Tyr Leu Leu Ala Ser Ser Leu Gly Ile Arg Ser Phe Lys Asn Ser
1               5                  10                  15

Ser Leu Asn Pro Glu
            20

(2) INFORMATION FOR SEQ ID NO:20:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:20:

Lys His Thr His His Ala Pro Leu Ser Pro Arg Thr Phe His Pro Leu
1               5                   10                  15

Arg Ser Glu Ala Tyr
            20

(2) INFORMATION FOR SEQ ID NO:21:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:21:

Lys Pro Ala Tyr His Val Pro Leu Ser Pro Arg Ser Phe His Pro Leu
1               5                   10                  15

Arg Gly Glu Val Asn
            20

(2) INFORMATION FOR SEQ ID NO:22:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:22:

Lys Leu Ala Leu His Ser Pro Leu Ser Pro Arg Gly Phe Asp Pro Leu
1               5                   10                  15

Arg Gly His Asn His
            20

(2) INFORMATION FOR SEQ ID NO:23:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:23:

Asp Pro Asp Asn Ile Ala Ala Trp Tyr Leu Arg Ser Asn Asn Gly Asn
1               5                   10                  15

Arg Arg Asn Tyr Tyr
            20

(2) INFORMATION FOR SEQ ID NO:24:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:24:

Asn Pro Asp Asn Ile Ala Ala Trp Tyr Leu Arg Ser Asn Thr Gly Asn
1               5                   10                  15

Arg Lys Tyr Tyr Tyr
            20

(2) INFORMATION FOR SEQ ID NO:25:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:25:

Asn Pro Asp Thr Ile Ala Ala Trp Tyr Leu Arg Gly His Gly Gly His
1               5                   10                  15

Lys Lys Phe Tyr Tyr
            20

(2) INFORMATION FOR SEQ ID NO:26:

(i) SEQUENCE CHARACTERISTICS:
        (A) LENGTH: 6909 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:26:

| | | | | | |
|---|---|---|---|---|---|
| GAATTCCGCA | GCCCGGAGTG | TGGTTAGCAG | CTCGGCAAGC | GCTGCCCAGG | TCCTGGGGTG | 60 |
| GTGGCAGCCA | GCGGGAGCAG | GAAAGGAAGC | ATGTTCCCAG | CTGCCCACG | CCTCTGGGTC | 120 |
| CTGGTGGTCT | TGGGCACCAG | CTGGGTAGGC | TGGGGGAGCC | AAGGGACAGA | AGCGGCACAG | 180 |
| CTAAGGCAGT | TCTACGTGGC | TGCTCAGGGC | ATCAGTTGGA | GCTACCGACC | TGAGCCCACA | 240 |
| AACTCAAGTT | TGAATCTTTC | TGTAACTTCC | TTTAAGAAAA | TTGTCTACAG | AGAGTATGAA | 300 |
| CCATATTTTA | AGAAAGAAAA | ACCACAATCT | ACCATTTCAG | GACTTCTTGG | GCCTACTTTA | 360 |
| TATGCTGAAG | TCGGAGACAT | CATAAAAGTT | CACTTTAAAA | ATAAGGCAGA | TAAGCCCTTG | 420 |
| AGCATCCATC | CTCAAGGAAT | TAGGTACAGT | AAATTATCAG | AAGGTGCTTC | TTACCTTGAC | 480 |
| CACACATTCC | CTGCGGAGAA | GATGGACGAC | GCTGTGGCTC | CAGGCCGAGA | ATACACCTAT | 540 |
| GAATGGAGTA | TCAGTGAGGA | CAGTGGACCC | ACCCATGATG | ACCCTCCATG | CCTCACACAC | 600 |
| ATCTATTACT | CCCATGAAAA | TCTGATCGAG | GATTTCAACT | CGGGGCTGAT | TGGGCCCCTG | 660 |
| CTTATCTGTA | AAAAAGGGAC | CCTAACTGAG | GGTGGGACAC | AGAAGACGTT | TGACAAGCAA | 720 |
| ATCGTGCTAC | TATTTGCTGT | GTTTGATGAA | AGCAAGAGCT | GGAGCCAGTC | ATCATCCCTA | 780 |
| ATGTACACAG | TCAATGGATA | TGTGAATGGG | ACAATGCCAG | ATATAACAGT | TTGTGCCCAT | 840 |
| GACCACATCA | GCTGGCATCT | GCTGGGAATG | AGCTCGGGGC | CAGAATTATT | CTCCATTCAT | 900 |
| TTCAACGGCC | AGGTCCTGGA | GCAGAACCAT | CATAAGGTCT | CAGCCATCAC | CCTTGTCAGT | 960 |
| GCTACATCCA | CTACCGCAAA | TATGACTGTG | GGCCCAGAGG | GAAAGTGGAT | CATATCTTCT | 1020 |
| CTCACCCCAA | AACATTTGCA | AGCTGGGATG | CAGGCTTACA | TTGACATTAA | AAACTGCCCA | 1080 |
| AAGAAAACCA | GGAATCTTAA | GAAAATAACT | CGTGAGCAGA | GGCGGCACAT | GAAGAGGTGG | 1140 |

```
GAATACTTCA TTGCTGCAGA GGAAGTCATT TGGGACTATG CACCTGTAAT ACCAGCGAAT    1200

ATGGACAAAA AATACAGGTC TCAGCATTTG GATAATTTCT CAAACCAAAT TGGAAAACAT    1260

TATAAGAAAG TTATGTACAC ACAGTACGAA GATGAGTCCT TCACCAAACA TACAGTGAAT    1320

CCCAATATGA AGAAGATGG GATTTTGGGT CCTATTATCA GAGCCCAGGT CAGAGACACA     1380

CTCAAAATCG TGTTCAAAAA TATGGCCAGC CGCCCCTATA GCATTTACCC TCATGGAGTG    1440

ACCTTCTCGC CTTATGAAGA TGAAGTCAAC TCTTCTTTCA CCTCAGGCAG GAACAACACC    1500

ATGATCAGAG CAGTTCAACC AGGGGAAACC TATACTTATA AGTGGAACAT CTTAGAGTTT    1560

GATGAACCCA CAGAAAATGA TGCCCAGTGC TTAACAAGAC CATACTACAG TGACGTGGAC    1620

ATCATGAGAG ACATCGCCTC TGGGCTAATA GGACTACTTC TAATCTGTAA GAGCAGATCC    1680

CTGGACAGGC GAGGAATACA GAGGGCAGCA GACATCGAAC AGCAGGCTGT GTTTGCTGTG    1740

TTTGATGAGA ACAAAAGCTG GTACCTTGAG GACAACATCA ACAAGTTTTG TGAAAATCCT    1800

GATGAGGTGA AACGTGATGA CCCCAAGTTT TATGAATCAA ACATCATGAG CACTATCAAT    1860

GGCTATGTGC CTGAGAGCAT AACTACTCTT GGATTCTGCT TTGATGACAC TGTCCAGTGG    1920

CACTTCTGTA GTGTGGGGAC CCAGAATGAA ATTTTGACCA TCCACTTCAC TGGGCACTCA    1980

TTCATCTATG GAAAGAGGCA TGAGGACACC TTGACCCTCT TCCCCATGCG TGGAGAATCT    2040

GTGACGGTCA CAATGGATAA TGTTGGAACT TGGATGTTAA CTTCCATGAA TTCTAGTCCA    2100

AGAAGCAAAA AGCTGAGGCT GAAATTCAGG GATGTTAAAT GTATCCCAGA TGATGATGAA    2160

GACTCATATG AGATTTTTGA ACCTCCAGAA TCTACAGTCA TGGCTACACG GAAAATGCAT    2220

GATCGTTTAG AACCTGAAGA TGAAGAGAGT GATGCTGACT ATGATTACCA GAACAGACTG    2280

GCTGCAGCAT TAGGAATTAG GTCATTCCGA AACTCATCAT TGAACCAGGA AGAAGAAGAG    2340

TTCAATCTTA CTGCCCTAGC TCTGGAGAAT GGCACTGAAT TCGTTTCTTC GAACACAGAT    2400

ATAATTGTTG GTTCAAATTA TTCTTCCCCA AGTAATATTA GTAAGTTCAC TGTCAATAAC    2460

CTTGCAGAAC CTCAGAAAGC CCCTTCTCAC CAACAAGCCA CCACAGCTGG TTCCCCACTG    2520

AGACACCTCA TTGGCAAGAA CTCAGTTCTC AATTCTTCCA CAGCAGAGCA TTCCAGCCCA    2580

TATTCTGAAG ACCCTATAGA GGATCCTCTA CAGCCAGATG TCACAGGGAT ACGTCTACTT    2640

TCACTTGGTG CTGGAGAATT CAGAAGTCAA GAACATGCTA AGCGTAAGGG ACCCAAGGTA    2700

GAAAGAGATC AAGCAGCAAA GCACAGGTTC TCCTGGATGA AATTACTAGC ACATAAAGTT    2760

GGGAGACACC TAAGCCAAGA CACTGGTTCT CCTTCCGGAA TGAGGCCCTG GGAGGACCTT    2820

CCTAGCCAAG ACACTGGTTC TCCTTCCAGA ATGAGGCCCT GGGAGGACCC TCCTAGTGAT    2880

CTGTTACTCT TAAAACAAAG TAACTCATCT AAGATTTTGG TTGGGAGATG GCATTTGGCT    2940

TCTGAGAAAG GTAGCTATGA ATAATCCAA GATACTGATG AAGACACAGC TGTTAACAAT     3000

TGGCTGATCA GCCCCAGAA TGCCTCACGT GCTTGGGGAG AAAGCACCCC TCTTGCCAAC     3060

AAGCCTGGAA AGCAGAGTGG CCACCCAAAG TTTCCTAGAG TTAGACATAA ATCTCTACAA    3120

GTAAGACAGG ATGGAGGAAA GAGTAGACTG AAGAAAAGCC AGTTTCTCAT TAAGACACGA    3180

AAAAAGAAAA AAGAGAAGCA CACACACCAT GCTCCTTTAT CTCCGAGGAC CTTTCACCCT    3240

CTAAGAAGTG AAGCCTACAA CACATTTTCA GAAAGAAGAC TTAAGCATTC GTTGGTGCTT    3300

CATAAATCCA ATGAAACATC TCTTCCCACA GACCTCAATC AGACATTGCC CTCTATGGAT    3360

TTTGGCTGGA TAGCCTCACT TCCTGACCAT AATCAGAATT CCTCAAATGA CACTGGTCAG    3420

GCAAGCTGTC CTCCAGGTCT TTATCAGACA GTGCCCCCAG AGGAACACTA TCAAACATTC    3480
```

```
CCCATTCAAG ACCCTGATCA AATGCACTCT ACTTCAGACC CCAGTCACAG ATCCTCTTCT    3540

CCAGAGCTCA GTGAAATGCT TGAGTATGAC CGAAGTCACA AGTCCTTCCC CACAGATATA    3600

AGTCAAATGT CCCCTTCCTC AGAACATGAA GTCTGGCAGA CAGTCATCTC TCCAGACCTC    3660

AGCCAGGTGA CCCTCTCTCC AGAACTCAGC CAGACAAACC TCTCTCCAGA CCTCAGCCAC    3720

ACGACTCTCT CTCCAGAACT CATTCAGAGA AACCTTTCCC CAGCCCTCGG TCAGATGCCC    3780

ATTTCTCCAG ACCTCAGCCA TACAACCCTT TCTCCAGACC TCAGCCATAC AACCCTTTCT    3840

TTAGACCTCA GCCAGACAAA CCTCTCTCCA GAACTCAGTC AGACAAACCT TTCCCCAGCC    3900

CTCGGTCAGA TGCCCCTTTC TCCAGACCTC AGCCATACAA CCCTTTCTCT AGACTTCAGC    3960

CAGACAAACC TCTCTCCAGA ACTCAGCCAT ATGACTCTCT CTCCAGAACT CAGTCAGACA    4020

AACCTTTCCC CAGCCCTTGG TCAGATGCCC ATTTCTCCAG ACCTCAGCCA TACAACCCTT    4080

TCTCTAGACT TCAGCCAGAC AAACCTCTCT CCAGAACTCA GTCAAACAAA CCTTTCCCCA    4140

GCCCTCGGTC AGATGCCCCT TTCTCCAGAC CCCAGCCATA CAACCCTTTC TCTAGACCTC    4200

AGCCAGACAA ACCTCTCTCC AGAACTCAGT CAGACAAACC TTTCCCCAGA CCTCAGTGAG    4260

ATGCCCCTCT TTGCAGATCT CAGTCAAATT CCCCTTACCC CAGACCTCGA CCAGATGACA    4320

CTTTCTCCAG ACCTTGGTGA GACAGATCTT TCCCCAAACT TTGGTCAGAT GTCCCTTTCC    4380

CCAGACCTCA GCCAGGTGAC TCTCTCTCCA GACATCAGTG ACACCACCCT TCTCCCGGAT    4440

CTCAGCCAGA TATCACCTCC TCCAGACCTT GATCAGATAT TCTACCCTTC TGAATCTAGT    4500

CAGTCATTGC TTCTTCAAGA ATTTAATGAG TCTTTTCCTT ATCCAGACCT TGGTCAGATG    4560

CCATCTCCTT CATCTCCTAC TCTCAATGAT ACTTTTCTAT CAAAGGAATT TAATCCACTG    4620

GTTATAGTGG GCCTCAGTAA AGATGGTACA GATTACATTG AGATCATTCC AAAGGAAGAG    4680

GTCCAGAGCA GTGAAGATGA CTATGCTGAA ATTGATTATG TGCCCTATGA TGACCCCTAC    4740

AAAACTGATG TTAGGACAAA CATCAACTCC TCCAGAGATC CTGACAACAT TGCAGCATGG    4800

TACCTCCGCA GCAACAATGG AAACAGAAGA AATTATTACA TTGCTGCTGA AGAAATATCC    4860

TGGGATTATT CAGAATTTGT ACAAAGGGAA ACAGATATTG AAGACTCTGA TGATATTCCA    4920

GAAGATACCA CATATAAGAA AGTAGTTTTT CGAAAGTACC TCGACAGCAC TTTTACCAAA    4980

CGTGATCCTC GAGGGGAGTA TGAAGAGCAT CTCGGAATTC TTGGTCCTAT TATCAGAGCT    5040

GAAGTGGATG ATGTTATCCA AGTTCGTTTT AAAAATTTAG CATCCAGACC GTATTCTCTA    5100

CATGCCCATG GACTTTCCTA TGAAAAATCA TCAGAGGGAA AGACTTATGA AGATGACTCT    5160

CCTGAATGGT TTAAGGAAGA TAATGCTGTT CAGCCAAATA GCAGTTATAC CTACGTATGG    5220

CATGCCACTG AGCGATCAGG GCCAGAAAGT CCTGGCTCTG CCTGTCGGGC TTGGGCCTAC    5280

TACTCAGCTG TGAACCCAGA AAAAGATATT CACTCAGGCT TGATAGGTCC CCTCCTAATC    5340

TGCCAAAAAG GAATACTACA TAAGGACAGC AACATGCCTG TGGACATGAG AGAATTTGTC    5400

TTACTATTTA TGACCTTTGA TGAAAAGAAG AGCTGGTACT ATGAAAAGAA GTCCCGAAGT    5460

TCTTGGAGAC TCACATCCTC AGAAATGAAA AAATCCCATG AGTTTCACGC CATTAATGGG    5520

ATGATCTACA GCTTGCCTGG CCTGAAAATG TATGAGCAAG AGTGGGTGAG GTTACACCTG    5580

CTGAACATAG GCGGCTCCCA AGACATTCAC GTGGTTCACT TCACGGCCA  GACCTTGCTG    5640

GAAAATGGCA ATAAACAGCA CCAGTTAGGG GTCTGGCCCC TTCTGCCTGG TTCATTTAAA    5700

ACTCTTGAAA TGAAGGCATC AAAACCTGGC TGGTGGCTCC TAAACACAGA GGTTGGAGAA    5760

AACCAGAGAG CAGGGATGCA AACGCCATTT CTTATCATGG ACAGAGACTG TAGGATGCCA    5820
```

-continued

```
ATGGGACTAA GCACTGGTAT CATATCTGAT TCACAGATCA AGGCTTCAGA GTTTCTGGGT    5880

TACTGGGAGC CCAGATTAGC AAGATTAAAC AATGGTGGAT CTTATAATGC TTGGAGTGTA    5940

GAAAAACTTG CAGCAGAATT TGCCTCTAAA CCTTGGATCC AGGTGGACAT GCAAAAGGAA    6000

GTCATAATCA CAGGGATCCA GACCCAAGGT GCCAAACACT ACCTGAAGTC CTGCTATACC    6060

ACAGAGTTCT ATGTAGCTTA CAGTTCCAAC CAGATCAACT GGCAGATCTT CAAAGGGAAC    6120

AGCACAAGGA ATGTGATGTA TTTTAATGGC AATTCAGATG CCTCTACAAT AAAAGAGAAT    6180

CAGTTTGACC CACCTATTGT GGCTAGATAT ATTAGGATCC CTCCAACTCG AGCCTATAAC    6240

AGACCTACCC TTCGATTGGA ACTGCAAGGT TGTGAGGTAA ATGGATGTTC CACACCCCTG    6300

GGTATGGAAA ATGGAAAGAT AGAAAACAAG CAAATCACAG CTTCTTCGTT TAAGAAATCT    6360

TGGTGGGAG ATTACTGGGA ACCCTTCCGT GCCCGTCTGA ATGCCCAGGG ACGTGTGAAT     6420

GCCTGGCAAG CCAAGGCAAA CAACAATAAG CAGTGGCTAG AAATTGATCT ACTCAAGATC    6480

AAGAAGATAA CGGCAATTAT AACACAGGGC TGCAAGTCTC TGTCCTCTGA AATGTATGTA    6540

AAGAGCTATA CCATCCACTA CAGTGAGCAG GGAGTGGAAT GGAAACCATA CAGGCTGAAA    6600

TCCTCCATGG TGGACAAGAT TTTTGAAGGA AATACTAATA CCAAAGGACA TGTGAAGAAC    6660

TTTTTCAACC CCCCAATCAT TTCCAGGTTT ATCCGTGTCA TTCCTAAAAC ATGGAATCAA    6720

AGTATTACAC TTCGCCTGGA ACTCTTTGGC TGTGATATTT ACTAGAATTG AACATTCAAA    6780

AACCCCTGGA AGAGACTCTT TAAGACCTCA AACCATTTAG AATGGGCAAT GTATTTTACG    6840

CTGTGTTAAA TGTTAACAGT TTTCCACTAT TTCTCTTTCT TTTCTATTAG TGAATAAAAT    6900

TTTATACAA                                                            6909
```

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:27:

```
CTGTTATCAG AGCCCAGGTC                                                  20
```

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:28:

```
GGAGAGAAGG TCACCCCGTG                                                  20
```

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "DNA"

(xi) SEQUENCE DESCRIPTION: SEQ ID NO:29:

CTTCTCTCCT TACGAAGATG                                                        20

(2) INFORMATION FOR SEQ ID NO:30:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:30:

CCTAATCTGT GCCAGCG                                                           17

(2) INFORMATION FOR SEQ ID NO:31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:31:

CTCTTGTTCT CGTCAAACAC                                                        20

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:32:

TTGAGGACAA CATCAACAAG                                                        20

(2) INFORMATION FOR SEQ ID NO:33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:33:

TGCCACTGGA CAGTGTCATC                                                        20

(2) INFORMATION FOR SEQ ID NO:34:

(i) SEQUENCE CHARACTERISTICS:
            (A) LENGTH: 368 base pairs
            (B) TYPE: nucleic acid (C) STRANDEDNESS: double
        (D) TOPOLOGY: linear (ii) MOLECULE TYPE: DNA (genomic)

(xi) SEQUENCE DESCRIPTION: SEQ ID NO:34:

GTAAGCAACA GAAATACGGA AGCAAGGAAA AATTAAACAG GGCAAAGACA GATCAAGGGA      60

CTGGCAGTTT TAATATATTT AAATGTATTC ATCTAATTAT AAAATCAAAC ATAGCTCTCA     120

GTTTTATTTA GCATTTCATT CTTGTATATC CTACTTAATT TAAAAGATCT GGGATCGAAA     180

AGTAGAAAAG AATAGAGAGA ATAAAGCAGA GTCAGTATCA TTGGAGGAGT AAGGAATACT     240

ATATGGGAAC TAATTCCATC TGGTCACAAA TAAGCATAAT GAGACACACC CATACATCCC     300

CAAGGTTGTC TGCAAAGTGT GTCCCAACTC TTATAGCAAA GTAAATATGA CCGAGCAAGG     360

TGCACACA                                                             368

(2) INFORMATION FOR SEQ ID NO:35:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:35:

CCCACTGCTG CACTGCACAT CTGTGTGTGC ACACCTGTCC ATACATGCAC ACAAGCAGCT      60

GCCTTCATCT CGTCTGAAAT AGTTCTCATG AGTGACCTTA AACACGGAAA TAATAACTAT     120

GACTTAACTT TCTAG                                                     135

(2) INFORMATION FOR SEQ ID NO:36:

(i) SEQUENCE CHARACTERISTICS:
        (A) LENGTH: 302 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:36:

GTGGGAACCT TTCACTTCTT GGAGACTACT GATCTCCGAG AGGCATCCAC AGTGTTCTCT      60

TGTATTTGTC CAGTGGTTAT GACAAACGCA GTCATTAATA CGGAGGGTTA TCTCTCCTTT     120

CTGAGTGTCA TGGCGCCATC TAGTGGACAG ATATTGAACA GCTACATGCT ATCCATAGTC     180

AGGAGTTTTA ATACAAAAAG AATATTTTTC TTCATATTAA TTACTCTAAA TAAAAGCTAA     240

GGTAGATATT TATTATGATG AAATAATTTT TCTAAAAATT AAGAGCGTAT ATTTTCTTCC     300

AG                                                                   302

(2) INFORMATION FOR SEQ ID NO:37:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:37:

GTATTTTATA CATAACATAA CCTTTAAAAA AAAAAAAAAA AAAAAAAAAA AAGAGGAATT     60

TCCCCTCGCT GGCACAGATT AGGTCTCACT ACGGAATAGG AGGAT     105

(2) INFORMATION FOR SEQ ID NO:38:

(i) SEQUENCE CHARACTERISTICS:
        (A) LENGTH: 267 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:38:

TCGTCCATTG GAACACGGTC AGTCAGCCAT TCTGAAAGTT TTCCAGTACT CTGACCTACA     60

GGTGTTATCT AAGGGAATTT CCCCCCTGGG TATTTTTGAC TGAATTCTCT GACTCCTTCT     120

CTTTGTGTTC ACATATTAGC TTTATCTCTG ACAAGGGTTT GGTAATCATG ACCTCCTAGG     180

TGCCAGACAC GTGGCTCCTC TGGACCCCAC GACAATGGGG ACATCGACAG CCCACCAGAG     240

CAGTGATCAC TGCCCTTTCC CCTGCAG     267

(2) INFORMATION FOR SEQ ID NO:39:

(i) SEQUENCE CHARACTERISTICS:
        (A) LENGTH: 85 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:39:

GTAAGTCAGA CTCCCGTGTC CACACTGGTG TCGCAGTGTG TCTGTACCCA AAGGAAAAAA     60

TGTGATGCTG GGCATAACTC TCTAA     85

(2) INFORMATION FOR SEQ ID NO:40:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:40:

TTTCCTGAGC TTTCAGCCTT CTCTTCTCTG TCTCTTATGA AG     42

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:41:

CCAAAGAAAA CGCAGAGCCC CAAGACC     27

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

CCTGGACCAG CAGGGTGTAC AG                                      22

(2) INFORMATION FOR SEQ ID NO:43:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:43:

TGTTCTGTAG GGGTCAT                                            17

(2) INFORMATION FOR SEQ ID NO:44:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

TCACTGCTCT CGCTCTG                                            17

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:45:

ACGATCAGAC CAGTTCAACC                                        20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:46:

CCTTGTAACG TCCACATCAC                                          20

(2) INFORMATION FOR SEQ ID NO:47:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:47:

GGACTGGCTG CTATTGGGCG AAGTG                                    25

(2) INFORMATION FOR SEQ ID NO:48:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:48:

GAAGAACTCG TCAAGAAGGC GATAGAAGG                                29

(2) INFORMATION FOR SEQ ID NO:49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:49:

AGGAGCTCAG TGAGAAC                                             17

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:50:

GGCAGGCTCA AACTTCACTA                                          20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        (ii) MOLECULE TYPE: other nucleic acid
            (A) DESCRIPTION: /desc = "DNA"

(xi) SEQUENCE DESCRIPTION: SEQ ID NO:51:

TTGCCTCTGG GCTGATAGGG                                                    20

(2) INFORMATION FOR SEQ ID NO:52:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:52:

AGGAGCTCAG TGAGAAC                                                       17

(2) INFORMATION FOR SEQ ID NO:53:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:53:

GGCAGGCTCA AACTTCACTA                                                    20

(2) INFORMATION FOR SEQ ID NO:54:

(i) SEQUENCE CHARACTERISTICS:
            (A) LENGTH: 277 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:54:

AATTAAATTC CAAAAAGAGA AAAAAAAAGG AAAAGAGAGA ATAAAAGCTG AAGAAACTCC         60

TTCAAGCCTA AACCATTTAG AGCAGGCCCT ATAGCATGGG TATTTTAAAT GTTAACAGAA        120

GTTCTGCTAT TTTTTTCTAG TTGAGAATAA GCTTTATGTG AGAAGCTTTT AATACTCCTT        180

CATCGCTGCC ACTAAGTGAG ATGGCAGCTA TTATTTCTTC ACTGATTTGA ATATAAATGG        240

GGAAATATTA AGACCTGGCA AGAATATGAC TGTTTTT                                 277
```

TRANSGENIC MICE EXPRESSING APC RESISTANT FACTOR V

FIELD OF THE INVENTION

The present invention relates to compositions and methods for the screening of compounds for anticoagulant activity. In particular, the present invention relates to the non-human transgenic animals expressing APC resistant factor V proteins which display a predisposition toward spontaneous thrombosis and the use of these transgenic animals for the screening of compounds for anticoagulant activity.

BACKGROUND

I. Overview Of Hemostasis And Thrombosis

Hemostasis refers to the arrest of blood loss from a damaged vessel. Following injury to a blood vessel, platelets adhere to macromolecules in the vessel's subendothelial regions, and, thereafter, aggregate to form a hemostatic plug. Platelets also stimulate local activation of plasma coagulation factors, resulting in the formation of a fibrin clot that serves to reinforce the platelet aggregate. The fibrin clot is subsequently lysed and the platelet aggregate retracts, leading to recanalization of the vessel.

The pathological process of thrombosis occurs when a fibrin clot and/or a platelet aggregate occludes a blood vessel. The location of the thrombotic occurrence plays a role in the resulting pathological effects. For example, venous thrombosis may result in the tissues drained by the vein to become edematous. By comparison, arterial thrombosis may cause ischemic necrosis of the tissue supplied by that artery. [See, e.g., Goodman and Gilman's *The Pharmacological Basis of Therapeutics* (8th edition, L. S. Goodman, A. Gilman, and A. G. Goodman, eds.) Macmillan Publishing Co. Inc., New York, p. 1311].

Thrombosis results in extensive morbidity and mortality and is a major medical problem both in the United States and abroad. To illustrate, arterial thrombosis contributes to the pathogenesis of myocardial infarction and stroke, two of the leading causes of death in the Western world. Moreover, venous thrombosis is responsible for approximately 300,000 hospital admissions each year in the United States.

II. Anticoagulant Therapy

The most commonly used anticoagulant agents are heparin, which is administered parenterally, and coumarin and indandione anticoagulants, which are administered orally. As will be discussed in detail hereafter, these agents are associated with severe shortcomings.

Heparin, an anionic, sulfated glycosaminoglycan present in the mast cells, is available commercially in the United States as the sodium salt. Heparin sodium, produced using either porcine intestinal mucosa or bovine lung tissue, is generally administered when an immediate anticoagulant effect is desired. Full-dose heparin therapy causes, among other things, the neutralization of thrombin, which results in the prevention of the conversion of fibrinogen to fibrin.

As with coumarin therapy (described below) the major adverse effect of heparin treatment is hemorrhage. Hemorrhagic complications have been reported in about 1–20% of patients receiving the agent, and severe cases of hemorrhage require the administration of protamine sulfate to counteract heparin's effect. In order to prevent bleeding and to determine the appropriate dose to maintain therapeutic efficacy, indicators of coagulation function (e.g., activated partial thromboplastin time) must be routinely monitored. Heparin is associated with other adverse effects, including acute thrombocytopenia and hypersensitivity reactions, that limit its usefulness in certain patient populations. [See generally, *AHFS Drug Information*, Gerald K. McKevoy, ed., pp. 931–37 (1995)].

The coumarin anticoagulants, which include dicumarol and warfarin sodium (e.g., warfarin sodium [Coumading®, Du Pont]), are synthetic 3-substituted derivatives of 4-hydroxycoumarin, while the indandione anticoagulants (e.g., anisindione) are synthetic derivatives of indan-1,3-dione. The agents affect the synthesis of factors II, VII, IX, and X in the liver through interference with vitamin K. These orally administered agents are generally used when an immediate anticoagulant effect is not necessary or subsequent to heparin therapy.

The most frequently observed untoward effect of the coumarin and indandione agents is hemorrhage; as with heparin, this is actually an extension of the agents' pharmacological effect. Indeed, minor incidents of bleeding occur in approximately 1% of patients receiving these agents per year of therapy. Though not as common, massive hemorrhage can also occur with oral anticoagulant treatment, most frequently in the gastrointestinal tract or genitourinary region. In addition to having a relatively narrow therapeutic index, coumarin is a teratogen and cannot be administered to pregnant patients.

Because of the relatively narrow therapeutic index of these agents, frequent monitoring of laboratory indices of anticoagulant response (e.g., prothrombin time) is required; such monitoring may be complicated by the fact that hemorrhage may occur when the prothrombin time is in the normal range (often due, e.g., when occult lesions are present). Moreover, many commonly used pharmaceutical agents (e.g., metronidazole, barbiturates, and oral contraceptives) may increase or decrease the patient's response to oral anticoagulant agents, especially warfarin, necessitating close monitoring of which medications are being taken and adjusting the dose of the anticoagulant agent when appropriate. [See generally, *AHFS Drug Information*, Gerald K. McKevoy, ed., pp. 924–29 (1995)].

III. Models For Testing Anticoagulant Agents

As set forth above, currently used anticoagulant agents are associated with severe shortcomings. These shortcomings, coupled with the obvious need for anticoagulant therapy, has spurred considerable effort in the pharmaceutical industry to develop new safe and effective agents. However, the animal models used for testing potentially safe and efficacious anticoagulant agents have extensive limitations of their own.

Presently used animal models generally require the introduction of an injury to induce artificial thrombosis. For example, one commonly used procedure to induce thrombosis requires ligature of the inferior vena cava in rats. [See M. Barbanti et al., Thrombosis and Haemostasis 69(2) 147–51 (1993); Reyers et al., "Stasis Induced Venous Thrombosis," In: Standardization of Animal Models of Thrombosis. K. Breddin and R. Zimmerman (eds.) Schattauer, Stuttgart; pp. 99–108 (1983)]. Unfortunately, this and other procedures are time consuming and invasive. Moreover, the specific experimental conditions used may influence whether thrombus formation occurs.

In addition to the inherent limitations of existing models requiring introduction of an injury to induce thrombosis, currently used animal models may not be entirely representative of thrombotic states in humans. This may be due, for example, to different sensitivities to a particular agent in the currently-used animal models than in humans because the artificially-induced injuries may activate other physiological factors that influence hemostasis. Thus, an agent that may appear to be effective in current models may be ineffective when administered to humans.

Clearly, what is needed are new methods and models for evaluating potentially useful experimental anticoagulant agents wherein the methods and models do not require the introduction of an artificial injury to induce thrombosis. The new methods and models should accurately predict the effect of the anticoagulant agents in humans and should also provide insight into the basic regulatory mechanisms of blood coagulation and the pathogenesis of human thrombosis.

SUMMARY

In one embodiment the present invention provides a non-human animal expressing an APC resistant factor V. The present invention is not limited by the nature of the non-human animal employed. In a preferred embodiment, the non-human animal is selected from the order Rodentia, with mice being particularly preferred. The present invention is not limited by the nature of modification which renders the FV protein resistant to cleavage by APC (activated protein C). In one embodiment, the genome of the mouse expressing an APC resistant factor V contains at least one (i.e., one or more) non-naturally occurring point mutation within an exon of the factor V gene. In another embodiment, the genome comprising one or more point mutations within an exon of the factor V gene further comprises a loxP site within the factor V gene.

In a preferred embodiment, the non-human animal expressing an APC resistant factor V is a mouse expressing an APC resistant factor V comprising at least one amino acid substitution relative to the wild-type factor V protein. The present invention is not limited by the specific amino acid substitution employed to render the factor V protein resistant to cleavage by APC. In one embodiment, the APC resistant factor V is factor V-R504Q (i.e., contains a glutamine residue at position 504 in place of the naturally-occurring arginine). In another embodiment, the APC resistant factor V is factor V-R305Q (i.e., contains a glutamine residue at position 305 in place of the naturally-occurring arginine). In yet another embodiment, the APC resistant factor V is factor V-R305Q:R504Q (i.e., contains a glutamine residue at positions 305 and 504 in place of the naturally-occurring arginine residues).

In a preferred embodiment, the non-human animal expressing an APC resistant factor V does not express wild-type factor V. In another preferred embodiment, the non-human animal expressing an APC resistant factor V displays spontaneous thrombosis.

The present invention further provides a non-human animal incapable of expressing functional wild-type factor V. The present invention is not limited by the nature of the non-human animal employed. In a preferred embodiment, the non-human animal is selected from the order Rodentia, with mice being particularly preferred. The present invention is not limited by the nature of modification which renders the non-human animal incapable of expressing functional wild-type factor V. In a preferred embodiment, the genome of the non-human animal incapable of expressing functional factor V contains a deletion of one or more exons of the factor V gene. In a particularly preferred embodiment, the genome of the non-human animal containing a deletion of at least one exon of the factor V gene further comprises a frameshift mutation within the deleted factor V gene. In another preferred embodiment, the genome of the non-human animal containing a deletion of at least one exon of the factor V gene further comprises a heterologous selectable marker gene. The present invention is not limited by the nature of the selectable marker(s) employed. A variety of selectable markers are known to the art and include positive (including dominant) selectable markers such as the neo gene, the hyg gene, and the gpt gene. Negative selectable markers (e.g., HSV-tk) may also be employed.

The present invention further provides a method for screening compounds for anticoagulant activity, comprising: a) providing: i) a non-human animal expressing an APC resistant factor V; ii) a composition comprising a test compound in a form suitable for administration such that the compound is bioavailable in the blood of the animal; and b) administering the test compound to the non-human animal. In one embodiment, the method further comprises c) measuring a reduction in the incidence of microvascular thrombi and thereby identifying a compound as therapeutic. The present invention is not limited by the nature of the compound to be screened for anticoagulant activity. In a preferred embodiment, the test compound is selected from the group consisting of heparin, oral anticoagulants (e.g., 4-hydroxycoumarin, dicumarol, phenprocoumon, warfarin sodium and indanedione derivatives), antithrombotics or anti-platelet drugs (i.e., drugs which suppress platelet function such as aspirin, sulfinpyrazone, dipyridamole, dextran 70, dextran 75, dazoxiben, ticlopidine and clofibrate), fibrinolytics or thrombolytics (i.e., drugs which promote the dissolution of thrombi by stimulating the activation of plasminogen to plasmin such as streptokinase, urokinase, tissue-type plasminogen activator, urokinase-type plasminogen activator, and aminocaproic acid). In addition, compounds which have been reported or proposed to protect or speed the healing of infarcted tissue such as growth factors and anti-oxidants many be tested for anticoagulation activity in the methods of the present invention.

In a preferred embodiment, the method of the present invention employs as the animals expressing an APC resistant factor V a pregnant female containing at least one fetus and the test compound is administered under conditions such that the test compound is administered to the fetus of said pregnant female in utero. In another preferred embodiment, the method further comprises c) permitting the fetus to progress to term and to be delivered. In yet another embodiment, the method further comprises d) measuring an increased rate of postnatal survival of the delivered animal.

The present invention also provides a method for producing a non-human transgenic animal predisposed to spontaneous thrombosis, the method comprising: a) providing an oligonucleotide sequence (i.e., a polynucleotide sequence) comprising: i) at least a portion of a non-human factor V gene, the portion comprising one or more point mutations within the coding region of the factor V gene, the point mutations resulting in the production of an APC resistant factor V protein; and ii) a positive selectable marker gene, the marker gene flanked by loxP sites; b) introducing said oligonucleotide sequence into an embryonic stem cell of a non-human animal under conditions such that the oligonucleotide sequence is homologously recombined into at least one of the naturally occurring factor V genes in the genome of the embryonic stem cell to produce an embryonic stem cell containing at least one factor V allele containing said one or more point mutations and the selectable marker gene; c) injecting the embryonic stem cell containing at least one factor V allele containing said one or more point mutations into the blastocyst of a non-human animal; d) introducing the injected blastocyst into a pseudo-pregnant non-human animal; and e) permitting the pseudo-pregnant animal to deliver progeny containing the homologously recombined oligonucleotide. In a preferred embodiment, the method further comprises prior to step c), introducing a source of Cre recombinase into the embryonic stem cell containing at least one factor V allele containing said one or more point mutations and the selectable marker gene under conditions such that the selectable marker gene is excised to produce an embryonic stem cell containing at least one factor V allele containing said one or more point mutations but lacking the selectable marker gene.

The present invention is not limited by the nature of the oligonucleotide sequence comprising a portion of a non-human factor V gene that comprises one or more point mutations within the coding region of the factor V gene which result in the production of an APC resistant factor V protein. In a preferred embodiment, the oligonucleotide sequence comprises the R504Q mutation. In another embodiment, the oligonucleotide sequence comprises the R305Q mutation. In yet another preferred embodiment, the oligonucleotide sequence comprises the R305Q and R504Q mutations.

In a preferred embodiment, the non-human transgenic animal comprising the homologously recombined oligonucleotide is further characterized by displaying spontaneous thrombosis. The present invention is not limited by the nature of the non-human animal employed. In a preferred embodiment, the non-human animal is selected from the order Rodentia, with mice being particularly preferred.

BRIEF DESCRIPTION OF THE DRAWINGS

FIGS. 2A and B show the murine Fv cDNA nucleotide sequence (SEQ ID NO:4) and translated protein sequence (SEQ ID NO:5).

FIGS. 4A and B show a cross species alignment of the factor V sequences (SEQ ID NOS:6–25) in the vicinity of the (4A) APC cleavage sites and (4B) thrombin cleavage sites.

FIG. 5 shows nucleotide sequences at the splice junctions for intron 8 (SEQ ID NOS:34–35), intron 9 (SEQ ID NO:36), intron 10 (SEQ ID NOS:37–38), intron 11 (SEQ ID NO:39), and intron 12 (SEQ ID NO:40) of the mouse Fv gene.

FIGS. 11A and B show schematic representations of the targeting of mutant Fv by (11A) homologous recombination and (11B) Cre recombinase excision.

DEFINITIONS

Figure 1A:
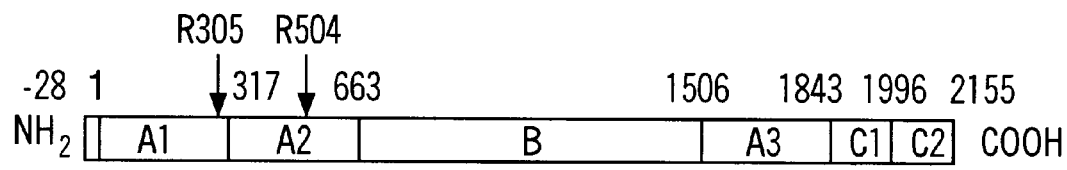
FIGS. 1A and B show a schematic representation of factor V protein (1A) and cDNA (1B) structure.

To facilitate understanding of the invention, a number of terms are defined below.

The "non-human animals" of the invention comprise any non-human animal whose genome contains an oligonucleotide sequence (e.g., a gene) encoding a modified form of factor V (FV). The modification may render the resulting factor V protein resistant to the natural anticoagulant action of activated protein C (APC) (referred to as an "APC resistant factor V" protein) or may render the resulting factor V protein completely nonfunctional. Such non-human animals include vertebrates such as rodents, non-human primates, ovines, bovines, ruminants, lagomorphs, porcines, caprines, equines, canines, felines, aves, etc. Preferred non-human animals are selected from the order Rodentia which includes murines (e.g., rats and mice), most preferably mice.

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals". A transgenic animal is an animal whose genome has been altered by the introduction of a transgene.

The term "transgene" as used herein refers to a foreign gene that is placed into an organism by introducing the foreign gene into embryonic stem (ES) cells, newly fertilized eggs or early embryos. The term "foreign gene" refers to any nucleic acid (e.g., gene sequence) which is introduced into the genome of an animal by experimental manipulations and may include gene sequences found in that animal so long as the introduced gene contains some modification (e.g., a point mutation, the presence of a selectable marker gene, the presence of a loxP site, etc.) relative to the naturally-occurring gene.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The "wild-type factor V" gene and gene product refers to the nucleotide and amino acid sequences provided in SEQ ID NOS:4 and 5, respectively. The art is well aware that certain modifications of SEQ ID NOS:4 and 5 can be made which will not interfere with the production of a polypeptide having an activity indistinguishable from that of the wild-type factor V (SEQ ID NO:5); the present invention specifically contemplates these variant forms of mouse Factor V. A "variant" of the mouse factor V is defined as an amino acid sequence differs by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

The terms "targeting vector" or "targeting construct" refer to oligonucleotide sequences comprising a selectable marker gene flanked on either side by factor V gene (Fv gene) sequences. The targeting vector contains factor V gene sequences sufficient to permit the homologous recombination of the targeting vector into at least one allele of the factor V gene resident in the chromosomes of the target or recipient cell (e.g., ES) cells. Typically, the targeting vector will contain 10 to 15 kb of DNA homologous to the factor V gene; this 10 to 15 kb of DNA will be divided more or less equally on each side of the selectable marker gene. The targeting vector may contain more than one selectable maker gene. When more than one selectable marker gene is employed, the targeting vector preferably contains a positive selectable marker (e.g., the neo gene) and a negative selectable marker [e.g., the Herpes simplex virus tk (HSV-tk) gene]. The presence of the positive selectable marker permits the selection of recipient cells containing an integrated copy of the targeting vector whether this integration occurred at the target site or at a random site. The presence of the negative selectable marker permits the identification of recipient cells containing the targeting vector at the targeted site (i.e., which has integrated by virtue of homologous recombination into the target site); cells which survive when grown in medium which selects against the expression of the negative selectable marker do not contain a copy of the negative selectable marker.

The targeting vectors of the present invention are of the "replacement-type;" integration of a replacement-type vector results in the insertion of a selectable marker into the target gene. As demonstrated herein replacement-type targeting vectors may be employed to disrupt a gene resulting in the generation of a null allele (i.e., an allele incapable of expressing a functional protein; null alleles may be generated by deleting a portion of the coding region, deleting the entire gene, introducing an insertion and/or a frameshift mutation, etc.) or may be used to introduce a modification (e.g., one or more point mutations) into a gene.

The terms "selectable marker" or "selectable gene product" as used herein refer to the use of a gene which encodes an enzymatic activity that confers resistance to an antibiotic or drug upon the cell in which the selectable marker is expressed. Selectable markers may be "positive"; positive selectable markers typically are dominant selectable markers, i.e., genes which encode an enzymatic activity which can be detected in any mammalian cell or cell line (including ES cells). Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Selectable markers may be "negative"; negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "promoter element" or "promoter" as used herein refer to a DNA sequence that is located at the 5' end of (i.e., precedes) a gene in a DNA polymer and provides a site for initiation of the transcription of the gene into mRNA.

The term "an oligonucleotide sequence comprising at least a portion of a non-human factor V gene" refers to a polynucleotide sequence (i.e., a nucleic acid sequence) containing a nucleotide sequence derived from a non-human factor V gene. This sequence may encode a portion (including the entire) of the factor V protein; alternatively, this sequence may contain non-coding regions derived from the factor V gene or a combination of coding and non-coding regions. The oligonucleotide may be RNA or DNA and may be of genomic or synthethic origin.

As used herein the term "portion" when in reference to a gene refers to fragments of that gene. The fragments may range in size from 10 nucleotides to the entire gene sequence minus one nucleotide. Thus, "an oligonucetide comprising at least a portion of a gene" may comprise fragments of the gene or the entire gene.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The transgenic animals of the present invention are preferentially generated by introduction of the targeting vectors into embryonal stem (ES) cells. ES cells are obtained by culturing pre-implantation embryos in vitro under appropriate conditions [Evans, et al. (1981) *Nature* 292:154–156; Bradley, et al. (1984) *Nature* 309:255–258; Gossler, et al. (1986) *Proc. Acad. Sci. USA* 83:9065–9069; and Robertson, et al. (1986) *Nature* 322:445–448]. Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal. For review see Jaenisch, (1988) *Science* 240:1468–1474. Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

Alternative methods for the generation of transgenic animals containing an altered factor V gene are known to the art. For example, embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage [Brinster, et al. (1985) *Proc. Natl. Acad. Sci. USA* 82:4438–4442]. As a consequence, all cells of the transgenic non-human animal will carry the incorporated transgene. This will in general also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873,191 describes a method for the micro-injection of zygotes; the disclosure of this patent is incorporated herein in its entirety.

Retroviral infection can also be used to introduce transgenes into a non-human animal. The developing non-human embryo can be cultured in vitro to the blastocyst stage. During this time, the blastomeres can be targets for retroviral infection [Janenich (1976) *Proc. Natl. Acad. Sci. USA* 73:1260–1264]. Efficient infection of the blastomeres is obtained by enzymatic treatment to remove the zona pellucida [Hogan et al. (1986) in *Manipulating the Mouse Embryo*, Cold Spring Harbor Laboratory Press, Plainview, N.Y.]. The viral vector system used to introduce the transgene is typically a replication-defective retrovirus carrying the transgene [Jahner, D. et al. (1985) *Proc. Natl. Acad Sci. USA* 82:6927–6931; Van der Putten, et al. (1985) *Proc. Natl. Acad Sci. USA* 82:6148–6152]. Transfection is easily and efficiently obtained by culturing the blastomeres on a monolayer of virus-producing cells [Van der Putten, supra; Stewart, et al. (1987) *EMBO J.* 6:383–388]. Alternatively, infection can be performed at a later stage. Virus or virus-producing cells can be injected into the blastocoele [Jahner, D. et al. (1982) *Nature* 298:623–628]. Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo [Jahner, D. et al. (1982) supra]. Additional means of using retroviruses or retroviral vectors to create transgenic animals known to the art involves the micro-injection of retroviral particles or mitomycin C-treated cells producing retrovirus into the perivitelline space of fertilized eggs or early embryos [PCT International Application WO 90/08832 (1990) and Haskell and Bowen (1995) Mol. Reprod. Dev. 40:386].

As used herein, the term "polymerase chain reaction" ("PCR") refers to the method of K. B. Mullis disclosed in U.S. Pat. Nos. 4,683,195, 4,683,202 and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

The term "thrombosis" refers to the formation or development of a blood clot within a blood vessel (e.g., a vein or artery). The term "thrombus" and grammatical equivalents refers to a clot in the cardiovascular system of an animal formed from blood constituents (e.g., clotting factors, platelets); thrombi may occlude a blood vessel or may attach to the vessel or heart wall without obstructing the lumen.

As used herein, the term "spontaneous thrombosis" is broadly used to mean the development of thrombi in an animal without apparent cause [i.e., in the absence of intervention (e.g., ligature of, insertion of a stent into, or crush injury of vessels) or the application of compounds known to induce thrombi (e.g., endotoxin)]. An animal which "displays spontaneous thrombosis" is an animal in which thrombi develop spontaneously as opposed to in response to experimental manipulation. For example, when transgenic mice heterozygous for the factor V R504Q point mutation [i.e., FV(R504Q/+) mice] are cross bred, one-third to one-half of the progeny homozygous for the factor V R504Q point mutation [i.e., FV(R504Q/R504Q) mice] die immediately following birth due to the spontaneous formation of numerous microvascular thrombi.

Thrombi which form during or immediately following birth are considered to be spontaneous; that is the process of birth is not an experimental manipulation which induces thrombosis in normal animals. Animals which display spontaneous thrombosis also include animals which display a predisposition to spontaneous thrombosis relative to an animal which expresses the wild-type factor V (i.e., SEQ ID NO:5).

The term "order Rodentia" refers to rodents i.e., placental mammals (class Euthria) which include the family Muridae (rats and mice).

The term "loxP site" refers to a short (34 bp) DNA sequence which is recognized by Cre recombinase of the *E. coli* bacteriophage P1. Placement of two loxP sites in the same orientation on either side of a DNA segment will result, in the presence of Cre recombinase, in efficient excision of the intervening DNA segment, leaving behind only a single copy of the loxP site [Sauer and Henderson (1988) Proc. Natl. Acad. Sci. USA 85:5166].

A animal whose genome "contains a non-naturally occurring point mutation within an exon of the factor V gene" refers to an animal whose genome contains a point mutation within an exon of the factor V gene which was introduced by means of molecular biological manipulation.

An "APC resistant factor V protein which comprises at least one amino acid substitution relative to the wild-type factor V protein" is a factor V protein that has an amino acid sequence which differs from the wild-type factor V sequence (SEQ ID NO:5) by at least one amino acid residue and this/these difference(s) imparts resistance to proteolytic cleavage by APC. APC resistance is measured using the assay provided in Example 1D. Any reproducible and statistically significant decrease in a test FV protein's clotting activity relative to the clotting activity of the wild-type FV protein indicates that the test FV protein is APC resistant; preferably the APC resistant FV displays a decrease (relative to the wild-type control) of 10% or more. In addition to the assay provided in Example 1D, APC resistance may be determined using commercial kits for human APC resistance as described in Example 4B. The assay is conducted such that plasma or conditioned medium containing the wild-type FV protein yields a ratio of the clotting time with addition of APC: the clotting time without APC addition of approximately 2.0. Any reproducible and statistically significant decrease in this ratio relative to the wild-type control indicates that a test FV protein is APC resistant. Preferably, the ratio is decreased 10% or more (i.e., a ratio of 1.8 or less). Most preferably, the APC resistant FV yields a ratio of approximately 1.5 or less (under assay conditions in which the wild-type FV yields a ratio of approximately 2.0).

An animal whose genome "comprises a heterologous selectable marker gene" is an animal whose genome contains a selectable marker gene not naturally found in the animal's genome which is introduced by means of molecular biological methods. A heterologous selectable marker is distinguished from an endogenous gene naturally found in the animal's genome in that expression or activity of the heterologous selectable marker can be selected for or against.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment or prevention of spontaneous thrombosis in animals (e.g., human thrombophilia).

The term "anticoagulant" refers to a chemical compound or entity that is capable of blocking, either partially or completely, blood clotting. Examples of anticoagulants include, but are not limited to, heparin, racemic warfarin sodium, 4-hydroxycoumarin, dicumarol, phenprocoumon and indanedione derivatives (e.g., anisindione). The use of derivatives of known anticoagulants is encompassed by the methods of the present invention. Indeed any compound, which functionally behaves as an anticoagulant is encompassed by the methods of the present invention. Anticoagulant activity can be measured using methods well known in the art, and as provided herein in Example 1. Briefly, a solution containing the test compound (i.e., the compound whose anticoagulant activity is sought to be tested) is incubated with factor V deficient human plasma in the presence of thromboplastin and $CaCl_2$, and the time to clot formation is measured using a coagulation timer. Where desirable, e.g. to compare the relative anticoagulant efficacy of different compounds, a standard curve may be generated using dilutions of normal human plasma.

A compound is said to be "in a form suitable for administration such that the compound is bioavailable in the blood of the animal" when the compound may be administered to an animal by any desired route (e.g., oral, intravenous, subcutaneous, intramuscular, etc.) and the compound or its active metabolites appears in the blood of the animal in an active form. Administration of a compound to a pregnant female may result in delivery of bioavailable compound to the fetuses of the pregnant animal.

DESCRIPTION OF THE INVENTION

The present invention provides compositions and methods for the screening of compounds having anticoagulant activity. The present invention provides for the first time the nucleotide sequence of the mouse factor V gene, including the sequence of the full-length cDNA. The present invention further provides the amino acid sequence of the mouse factor V protein and the sequence of several APC resistant forms of mouse factor V.

The present invention provides transgenic animals which contain modifications in the factor V gene. Animals lacking the ability to express a functional factor V protein are provided. Animals expressing an APC resistant factor V protein are provided; these animals display a predisposition toward spontaneous thrombosis and provide an animal model for human thrombophilia The Description Of The Invention is divided into the following sections: I. Factor V; II. Factor V Deficiency; III. Thrombophilia; IV. Transgenic Mouse Models for Coagulation Factor Deficiencies; V. Animal Models For Factor V Disorders; and VI. Screening Compounds For Anticoagulant Activity.

I. Factor V

Factor V (FV) is a central regulatory protein in the coagulation cascade. It serves as a critical cofactor for factor Xa (FXa), together forming the "prothrombinase" complex which in the presence of calcium and a phospholipid surface, efficiently converts prothrombin to active thrombin. Factor Va (FVa) is also a proteolytic target for activated protein C (APC). APC exerts its anticoagulant function through its inactivation of FVa and factor VIIIa (FVIIIa).

Human [Jenny el al. (1987) Proc. Natl. Acad. Sci. USA 84:4845 and Cripe et al. (1992) Biochem. 31:3777] and bovine [Guinto et al. (1992) J. Biol. Chem. 267:2971] FV cDNA sequences have been determined and demonstrate a high degree of conservation. Sequence data has not yet been reported for any other mammalian species. The FV protein is highly homologous to FVIII, both in structure and function. The position of thrombin and APC cleavage sites are also highly conserved between FV and FVIII. The FV heavy and light chains are held together by noncovalent, divalent cation-dependent interactions. The posttranslational processing, assembly, and secretion of FV have been studied in detail [Pittman and Kaufman (1993) Methods Enzymol. 222:236] and are similar to FVIII, although FV is more efficiently expressed. Tyrosine sulfation is required for both for FV and FVIII function [Pittman et al. (1994) Biochem. 33:6952]. In addition, the poorly conserved B domain is not required for either FVIII [Toole et al. (1986) Proc. Natl. Acad. Sci. USA 83:5939], or FV procoagulant function [Marquete et al. (1995) Blood 86:3026 and Pittman et al. (1994) Blood 84:4214]. The B domain is contained in a single large exon for both proteins [Cripe et al., supra].

FV is expressed predominantly in the liver and the megakaryocyte [Mazzorana et al. (1991) Br. J. Haematol. 78:229; Giddings et al. (1975) Br. J. Haematol. 29:57; and Chiu et al. (1985) J. Clin. Invest. 75:339]. Liver expression is thought to be the primary source for the large plasma pool of FV [Mazzorana et al., supra and Giddings el al., supra]. FV plasma concentration ranges from 4–14 μg/ml, approximately 100 fold greater than that of plasma FVIII. Megakaryocytes also synthesize FV [Chiu et al., supra], and package it as a major component of the (α-granule [Chesney et al. (1981) Proc. Natl. Acad. Sci. USA 78:5180 and Ortel et al. (1992) J. Biol. Chem. 267:4189]. The platelet pool in humans comprises ~20% of circulating FV [Tracy et al. (1982) Blood 60:59]. FV synthesis has also been reported in cultured aortic endothelium [Cerveny et al. (1984) Blood 63:1467], several types of lymphocytes [Shen et al. (1993) J. Immunol. 150:2992], and vascular smooth muscle cells [Rodgers (1988) Biochim. Biophys. Acta 968:17].

FV association with membrane surfaces is a central step in the assembly of the prothrombinase complex, most likely involving the platelet surface. However, FV has been demonstrated immunologically on the endothelial cell surface of normal blood vessels (Giddings et al., supra) where it may play an important role. The relative contributions of the platelet and plasma pools of FV to coagulation are not well established. The significant bleeding observed in FV Quebec patients, whose FV deficiency is restricted to the platelet, suggests that the platelet pool is particularly critical for FV function [Tracy et al. (1984) J. Clin. Invest. 74:1221]. This hypothesis is further supported by the observation that platelet transfusions are often quite effective in the treatment of FV deficiency [Roberts and Eberst (1994) *Thrombosis and Hemorrhage*, Loscalzo and Schafer (eds), Blackwell Scientific Publications, p. 701].

II. Factor V Deficiency

Genetic abnormalities of FV have been associated with inherited bleeding disorders as well as a familial predisposition to thrombosis. Inherited FV deficiency, or parahemophilia, is a rare congenital bleeding disorder with an estimated frequency of 1:1,000,000 [Roberts and Eberst, supra and Murray et al. (1995) Blood 86:1820]. Markedly decreased levels of FV can be associated with severe bleeding similar to that observed in classic hemophilia A. Though the severity of bleeding is generally related to the level of residual FV activity, this correlation is less consistent than in FVIII deficiency, possibly due to variation in the relative reduction of the plasma and platelet pools. Of note, nearly all patients have residual, detectable FV activity. Though there are rare reports of patients with <1% activity associated with severe hemorrhage, the molecular defects in these patients have not yet been characterized [Tracy and Mann (1987) Hum. Pathol. 18:162]. Mutation identification in this disorder is technically difficult given the large size of the gene and the autosomal recessive inheritance, generally requiring characterization of two different mutations in a compound heterozygous patient. The only mutation in the factor V gene (Fv) reported to date is FV New Brunswick [Murray et al., supra], a missense mutation leading to a qualitative functional defect. Thus, complete genetic deficiency of FV in humans has not yet been definitively documented. However, it has generally been assumed that this condition would lead to a phenotype similar to that of severe hemophilia A. FXa exhibits very low levels of prothrombinase activity in vitro in the absence of FV, decreased by ~$10^5$ compared to FXa in the presence of FVa [Krishnaswamy et al. (1987) J. Biol. Chem. 262:3291 and Krishnaswamy et al. (1993) Methods Enzymol. 222:260]. Thus, FV deficient patients might activate thrombin through the trace residual activity of FXa or through alternative mechanisms.

Rare patients with acquired inhibitors to FV have been reported, generally associated with severe hemorrhage (Roberts and Eberst, supra). As noted above, an unusual, autosomal dominant inherited deficiency of FV function restricted to the platelet pool has been referred to as FV Quebec [Tracy et al. (1984), supra]. Finally, a rare autosomal recessive disorder characterized by combined deficiency of both FV and FVIII has been described in Jews of Middle Eastern origin [Seligsohn et al. (1982) N. Engl. J. Med. 307:1191] as well as several other populations, frequently associated with consanguinity. In these patients, antigen and activity levels of both proteins are reduced to the range of 5–15%. Though this disorder was initially thought to be due to deficiency of protein C inhibitor [Marlar and Griffin (1980) J. Clin. Invest. 66:1186] this hypothesis has been disproved [Gardiner and Griffin (1984) Thromb. Res. 36:197] and the relevant genetic defect is currently unknown.

III. Thrombophilia

Venous thrombosis, most commonly in the lower extremities, affects approximately 1:1000 individuals in the U.S. per year and is responsible for approximately 300,000 hospital admissions annually. Abnormalities in coagulation balance may also contribute to atherosclerosis resulting in stroke and myocardial infarction. The occurrence of venous thrombosis in patients under the age of 45, recurrent unexplained thromboses, or positive family history are all suggestive of an inherited predisposition to thrombosis or "thrombophilia". Indeed, a positive family history can be elicited in approximately 40% of young patients [Malm el al. (1992) Thromb. Haemost. 68:7 and Bauer (1994) *Thrombosis and Hemorrhage*, Loscalzo and Schafer (eds), Blackwell Scientific Publications, p. 809]. Three well defined genetic syndromes due to coagulation protein deficiencies have been associated with inherited thrombophilia: antithrombin III deficiency, protein C deficiency, and protein S deficiency. In 1993, Dahlbäck et al. first reported a poor anticoagulant response to activated protein C in three families with familial thrombophilia [Dahlbäck et al. (1993) Proc. Natl. Acad. Sci. USA 90:1004]. This APC resistance syndrome is autosomal dominant in inheritance and can be demonstrated in 20–50% of patients with venous thrombosis [Svensson and Dahlbäck (1994) N. Engl. J. Med. 330:517; Griffin et al. (1993) Blood 82:1989; and Koster el al. (1993) Lancet 342:1503].

Dahlbäck and coworkers identified the APC resistance factor as FV by direct protein sequence analysis [Dahlbäck and Hildebrand (1994) Proc. Natl. Acad. Sci. USA 91:1396]. The role of FV in APC resistance was subsequently confirmed by others [Sun et al. (1994) Blood 83:3120]. Bertina and coworkers [Bertina et al. (1994) Nature 369:64] identified a G>A substitution at nucleotide position 1691 of FV resulting in the substitution of glutamine for arginine 506 (R506Q), a known protein C cleavage site within FV. The R506Q mutation accounts for >90% of individuals with APC resistance, and has an allele frequency ranging from 2–7% in a number of populations. It is thus at least 10-fold more common than any other known genetic risk factor for thrombosis [Zöller and Dahlbäck (1994) Lancet 343:1536; Greengard et al. (1994) Lancet 343:1361; and Voorberg et al. (1994) Lancet 343:1535]. Although homozygosity is associated with a greater risk of thrombosis [Zöller and Dahlbäck, supra; Greengard et al. (1994) N. Engl. J. Med. 331:1559; and Rosendaal (1995) Blood 85:1504], penetrance is still incomplete. Co-segregation of the R506Q mutation increases the penetrance of thrombosis in protein C [Koeleman et al. (1994) Blood 84:1031] and protein S [Koeleman et al. (1995) Throb. Haemost. 74:580] deficient patients. In addition, a possible moderating effect of the R506Q mutation on the severity of hemophilia A when combined with specific, recurrent FVIII gene missense mutations has also been reported [Nichols et al. (1996) Blood 88:1183]. However, this hypothesis is not supported by comparison of R506Q prevalence among severe and moderate hemophiliacs [Arbini et al. (1995) Thromb. Haemost (1995) 74:1255]. Although interaction of the R506Q mutation with other clotting factor abnormalities has not yet been reported, it is likely that such interactions will be identified.

IV. Transgenic Mouse Models For Coagulation Factor Deficiencies

Recent advances in molecular genetics have provided powerful tools for the generation of novel experimental mouse animal models for the study of human disease. A gene of interest can be introduced into the mouse by standard transgenic methods, whereas, newer homologous recombination techniques in embryonic stem (ES) cells can be used to specifically inactivate a target gene [Bronson and Smithies (1994) J. Biol. Chem. 269:27155; Rossant and Nagy (1995) Nature Med. 1:592; Barinaga (1994) Science 265:26; and Lin et al. (1995) Nature Med. 1:749]. These methods have recently been applied to a number of coagulation proteins. "Knockout" mice completely deficient in FVIII have been reported [Bi et al. (1995) Nature Genet. 10:119]. The bleeding phenotype of the severe hemophilic mouse is relatively mild compared to the human. Though no spontaneous bleeding was observed, fatal hemorrhage frequently occurred following minor tail injury for biopsy. Afibrinogenemia is a rare genetic disorder associated with complete absence of detectable plasma fibrinogen, but surprisingly, only moderate to severe hemorrhage. Mice engineered to be completely deficient in fibrinogen [Suh et al. (1995) Genes Dev. 9:2020] demonstrate a hemorrhagic phenotype, though all survive to birth and after the neonatal period demonstrate fairly normal survival, with only moderate hemorrhage. Murine models for a number of defects in the fibrinolytic system have been constructed by transgenic techniques, including plasminogen deficiency [Bugge et al. (1995) Genes Dev. 9:794 and Ploplis et al. (1995) Circulation 92:2585], urokinase-type plasminogen activator (uPA) and tissue plasminogen activator (tPA) deficiency [Carmeliet et al. (1994) Nature 368:419], plasminogen activator inhibitor-1 (PAI-1) deficiency [Carmeliet et al. (1993) J. Clin. Invest. 92:2746 and Carmeliet et al. (1993) J. Clin. Invest. 92:2756], and urokinase-type plasminogen activator receptor (uPAR) deficiency [Bugge et al. (1995) J. Biol. Chem. 270:16886]. A murine knockout of thrombomodulin has been reported and shows a surprising, embryonic lethal phenotype [Healy et al. (1995) Proc. Natl. Acad. Sci. USA 92:850].

V. Animal Models For Factor V Disorders

The present invention provides animal models for FV deficiency and animal models for thrombophilia (e.g., human APC resistance). These models are exemplified using transgenic mice which contain either a disrupted FV allele or a FV allele encoding an APC resistant FV. These transgenic mice are preferably generated using homologous recombination in embryonic stem (ES) cells; however, equivalent transgenic mice can also be produced by microinjection of mammalian oocytes. Techniques for the isolation, culture, microinjection and implantation of a variety of mammalian oocytes (e.g., mouse, pig, sheep, cow, etc.) are known to the art.

In order to produce the transgenic mice of the present invention, the mouse FV gene was first cloned and the mouse FV gene sequences were used to either disrupt the FV gene or to introduce mutations into the coding region of the FV gene to generate modified or mutant FV alleles encoding APC resistant FV.

a. cDNA Cloning Of Murine FV

A mouse bone marrow cDNA library was screened using a portion of the human Fv cDNA as a probe to identify cDNA clones containing mouse Fv gene sequences. The full length mouse Fv cDNA was assembled by joining portions of the FV gene located on multiple cDNA clones. The coding region for the mouse Fv cDNA is 6552 bp and is provided within SEQ ID NO:4.

cDNA libraries suitable for the identification of mouse or other mammalian FV cDNAs may be generated using techniques known to the art (e.g., isolation of mRNA, generation of cDNA, insertion of cDNA into a plasmid vector) [Sambrook et al. (1989) Molecular Cloning: A Laboratory Manual, Cold Spring Harbor, Plainview, N.Y., pp. 8.3–8.86]. In addition, cDNA libraries may be purchased from a number of sources (e.g., Stratagene). The cDNA library employed for the isolation of mammalian FV cDNAs is preferentially derived from bone marrow or liver; however, any tissue or cell line expressing FV may be utilized (e.g., isolated megakaryocytes, cultured aortic endothelium, lymphocytes and vascular smooth muscle cells).

The isolation of mouse FV cDNA sequences permitted the generation of modified mouse FV cDNAs encoding APC resistant FV proteins and the expression of APC resistant and wild-type mouse FV proteins in cultured cells. The recombinant mouse wild-type and APC resistant FV proteins were found to be active in coagulation assays.

Site-directed mutagenesis was employed to introduce mutations at putative APC cleavage sites in the mouse FV cDNA. Mutations which changed the naturally occurring arginine (R) at amino acid residues 305 and 504 of the mouse FV protein (SEQ ID NO:5) to glutamine (Q) were introduced to generate cDNAs encoding either FV-R305Q, FV-R504Q or FV-R305Q:R504Q proteins. In the mouse, R305 and R504 correspond to R306 and R506 in the human FV protein.

Expression of cDNAs encoding the FV-R305Q, FV-R504Q and FV-R305Q:R504Q proteins in COS-1 cells resulted in the production of APC resistant mouse FV. The single mutants (R305Q and R504Q) displayed partial resistance to APC cleavage while the double mutant (R305Q:R504Q) was markedly resistant to APC cleavage. These results are similar to those observed for recombinant human FV proteins.

The mouse FV cDNA permits the development of anti-mouse FV antibodies. Fragments of the mouse FV cDNA are inserted into a suitable expression vector; preferably the expression vector encodes an affinity tag such that a FV fusion protein containing an affinity tag is produced. The presence of the affinity tag facilitates purification of the fusion protein. As described herein, mouse FV proteins were expressed as fusion proteins with glutathione-S-transferase using the pGEX expression system (Pharmacia). A variety of other affinity tags are known to the art including maltose binding protein (MBP; pMAL expression system, New England Biolabs, Beverley, Mass.), thioredoxin (pTRXFUS and hpTRXFUS vectors; Invitrogen, San Diego, Calif. and Genetics Institute, Cambridge, Mass.) and poly-histidine tracts (pET expression system, Novagen, Madison, Wis. and the pQE expression system, Qiagen, Chatsworth, Calif.). In addition, a variety of expression vectors are available that encode a protease cleavage site between the affinity tag and the protein of interest which permits the removal of the affinity tag from the purified fusion protein (i.e., prior to immunization of animals for the production of antibodies).

Purified mouse FV proteins (expressed as native or fusion proteins) are used to immunize suitable host animals (e.g., mammals other than mice such as rabbits, goats, sheep, cows, horses) for the production of polyclonal antisera. Techniques for the immunization, boosting and screening of collected sera for the presence of the desired antibody are known in the art. The spleen of an immunized animal which has produced anti-mouse FV may be removed and the splenocytes fused with a myeloma cell line to create hybridomas secreting monoclonal anti-mouse FV antibodies.

b. Isolation Of Mouse FV Genomic Clones

Clones containing genomic FV sequences were isolated from a Sy129 mouse genomic library (Stratagene) using a fragment of the human FV cDNA as a probe. Two λ phage clones which span at least exons 7–13 of the mouse FV gene were isolated; these two genomic clones span approximately 30 kb of the mouse FV gene. The mouse FV genomic clones were mapped by restriction enzyme digestion and PCR and the intron-exon boundaries were determined by DNA sequencing. Genomic clones spanning other regions of the mouse FV gene are obtained by screening the Sv129 genomic library (or an equivalent mouse genomic library) using portions of the mouse FV cDNA corresponding to exons 1–6 or exons 14–25.

Genomic clones containing mouse FV sequences were used to create transgenic mice containing modified alleles of the FV gene as described below.

c. Factor V Null Transgenic Mice

Mice lacking the ability to express functional FV were generated using the technique of homologous recombination in ES cells. A targeting vector containing large fragments of FV genomic sequences flanking a selectable marker gene was inserted into the genome in ES cells via homologous recombination. This recombination event resulted in the deletion of exons 8–11, the introduction of a frameshift mutation in the FV coding region and the insertion of the neo gene. ES cells containing the homologously recombined targeting vector were injected into blastocysts and chimeric mice derived from the injected blastocysts were mated to produce mice heterozygous for the disrupted Fv gene. Heterozygous mice were then intercrossed to generate homozygous FV null progeny. The inability to produce functional FV was found to be partially embryonic lethal with about ½ of the Fv−/− mice dying during embryogenesis (at about E9-10). The remaining Fv−/− mice progress to term but generally die from massive hemorrhage within 2 hours of birth.

Fv−/− mice may be produced by a variety of means. It is not required that the specific targeting vector employed herein be used. Any targeting vector containing a large fragment (i.e., about≧5 kb) of mouse FV genomic sequence which is capable of homologously recombining into the mouse Fv gene in a manner that disrupts the Fv gene (e.g., introduction of a frameshift, premature stop codon, missense mutation, etc.) may be employed. The targeting vector may be of the replacement- or insertion-type [Huang (1993) Lab. Animal Sci. 43:156]. Replacement-type vectors contain two regions of homology with the targeted gene flanking a selectable marker and result in the insertion of the selectable marker which thereby disrupts the targeted gene. Insertion-type vectors contain a single region of homology with the targeted gene and result in the insertion of the entire targeting vector into the targeted gene.

The generation of Fv−/− mice need not employ ES cells; targeting vectors or transgenes may be microinjected into mouse oocytes to generate mice containing a disrupted Fv gene. The targeting vector employed need not employ a selectable marker, although the use of a selectable marker is preferred. PCR can be employed to screen the targeted cells to identify cells containing a disrupted Fv gene without the need to use a selectable marker and subject the targeted cells to growth in selective medium. In addition, chimeric RNA-DNA oligonucleotides containing modified RNA residues (2'-O-methyl modification of the ribose) can be used to target mutations (e.g., the introduction of a frameshift, premature stop codon, etc.) into the Fv gene using ES cells or oocytes to create Fv−/− mice [Strauss et al. (1996) Science 273:1386].

Mice containing a disrupted Fv gene find a number of uses. As discussed in more detail in the examples below, Fv(+/−) mice are mated with mice containing a transgene comprising the R305Q:R504Q mutations to create mice which express a highly APC resistant FV in a background lacking functional wild-type FV. These transgenic mice provide an animal model for human thrombophilia.

Fv(+/−) mice are mated to mice containing transgenes which direct the expression of wild-type or APC resistant FV proteins in either a liver-specific or megakaryocyte-specific manner to generate animal models which provide a means to optimize therapies and treatment for thrombophilia and FV deficient patients. Megakaryocyte-specific expression of Fv gene sequences is achieved by placing the FV cDNA under the transcriptional control of the rat platelet factor 4 (PF4) promoter [Ravid et al. (1991) Proc. Natl. Acad. Sci. USA 88:1521]. The 1.1 kb PF4 promoter will be amplified from total rat genomic DNA by PCR using primers based on the published sequence. This fragment is substituted for the CMV promoter in pcDNAIAmp (Invitrogen) by cloning into the NdeI/HindIII sites of the vector.

Liver-specific FV expression is achieved by placing the FV cDNA under the transcriptional control of the murine albumin promoter. Nearly identical albumin enhancer and promoter fragments have been previously demonstrated to direct very high levels of liver-specific gene expression in transgenic mice [Heckel et al. (1990) Cell 62:447 and Pinkert et al. (1992) Genes Dev. 1:268]. Murine albumin genomic plasmids are available (S. Camper, University of Michigan). The proximal albumin promoter from the SphI site at −309 to +21 is amplified by PCR and joined to the NheI/BamHI albumin upstream enhancer (Pinkert et al., supra) and together substituted for the CMV promoter in the pcDNAIAmp expression vector.

The FV coding sequence is cloned into the polylinkers of the above modified expression vectors, exactly as described for the pCMV5 vector used for the expression of recombinant FV (Ex. 1). The pcDNAIAmp vector contributes downstream SV40 intron and polyA sequence for efficient RNA processing. To permit the transgene mRNA product to be distinguished from the endogenous FV mRNA by RNA PCR, the FV cDNA sequence are subtly altered in the 3' untranslated region. For this purpose, a 20 bp segment is inserted by PCR mutagenesis into the 3' untranslated region, immediately downstream of the termination codon. PCR primers located on either side of this insertion are used to amplify mRNA from target tissues of transgenic mice to roughly quantify the level of transgene expression relative to that of the wild-type FV gene. Two bands are generated, differing in size by 20 bp, with their intensities defining the relative levels of expression of the transgene and wild-type mRNA species. PCR primers will be end labeled with [$\gamma$-$^{32}$P]ATP and the relative quantities of each band determined by phosphorimager analysis.

Transgenic mice are prepared using standard techniques [Hogan et al. (1994) *Manipulating the Mouse Embryo: A Laboratory Manual*, Cold Spring Harbor Laboratory Press, Plainview, N.Y.]. Transgenic founder mice are identified by screening PCR assay for the SV40 sequences contributed by the vector and confirmed by Southern blot analysis. Individual founder mice are crossed to C57BL/6J mice to establish a stable line. Two progeny from each founder are sacrificed and mRNA prepared from bone marrow, liver, spleen, kidney, brain, and testes for RT PCR to quantitate the relative level of FV transgene expression versus endogenous FV mRNA. Lines demonstrating a level of FV expression similar to that of the wild-type gene and restricted to the desired target tissues are selected.

In addition to the above uses for mice carrying a disrupted Fv gene, pregnant females carrying embryos which result from intercrosses of Fv(+/−) mice are used as a model system to test in utero gene replacement therapy protocols. Successful protocols result in the rescue of Fv(−/−) progeny (i.e., the insertion of a functional Fv gene into the Fv(−/−) animals in utero results in the birth of more animals per mother and in the survival of more animals immediately following birth.

d. Transgenic Mice Expressing APC Resistant FV

Mice containing one or more alleles encoding APC resistant FV proteins were generated using the techniques of homologous recombination in ES cells or microinjection of oocytes. A targeting vector was constructed which comprised an 11.8 kb NcoI-NotI restriction fragment derived from the mouse FV gene containing exons 7–10 (exon 10 was modified to contain the R504Q mutation using site-directed mutagenesis as described in Example 1C) into which a TK/neo cassette flanked on either side by loxP sites was inserted (into the SmaI site in exon 10 of the Fv gene). The targeting vector was introduced into ES cells and G418-resistant ES colonies were isolated. ES cells containing a homologously recombined targeting vector were identified. These ES cells were then transfected with a plasmid encoding the Cre recombinase to permit the excision of the TK-neo cassette. ES cells containing an excised allele comprising the modified exon 10 (containing the R504Q mutation) and a single loxP site in intron 10 were isolated, injected into blastocysts to generate chimeric mice. The chimeric mice were mated to produce mice heterozygous for the R504Q allele. Heterozygous mice were then intercrossed to generate homozygous FV(R504Q/R504Q) mice. The plasma of FV(R504Q/+) heterozygotes shows intermediate resistance to APC, while the plasma of FV(R504Q/R504Q) homozygous mice shows marked APC resistance. The homozygotes are predisposed to spontaneous thrombosis and about ⅓ to ½ of the homozygotes die in the immediate postnatal period. These animals provide a model for human thrombophilia and are used to screen compounds for the ability to act as long term anticoagulants.

As discussed above for the generation of FV null mice, it is not necessary that the specific targeting vector employed herein be used for the generation of mice containing the R504Q. Any targeting vector containing the modified exon 10 and a sufficient amount of the Fv gene to permit homologous recombination into the mouse Fv gene may be employed. It is not necessary that the targeting vector contain a selectable marker gene as discussed above. Further it is not necessary that, if a selectable marker is employed, the targeting vector employ a both positive (e.g., neo) and a negative (e.g., TK) selectable marker gene. Further it is not necessary that the selectable marker(s) be excised from the FV allele modified to contain the R504Q mutation (or any other desired APC resistant mutation). However if the selectable marker(s) are not to be excised it is preferred that the TK gene not be employed as a negative selectable marker as expression of the HSV-tk gene has been shown to be deleterious to spermatogenesis and therefore prevents the germline transmission of transgenes containing a functional TK gene.

Transgenic mice containing genes encoding APC resistant FV proteins may also be produced by microinjection of oocytes. As described herein (Ex. 5), transgenic mice containing a transgene encoding the FV(R305Q:R504Q) protein were generated using standard techniques. Mice containing the FV(R305Q:R504Q) transgene were crossed with Fv(+/−) mice to generate mice carrying the transgene in a background free of endogenous FV expression. Transgenic animals expressing FV-R305Q:R504Q provide an animal model for human thrombophilia and are used to screen compounds for anticoagulant activity.

In addition, chimeric RNA-DNA oligonucleotides containing modified RNA residues (2'-O-methyl modification of the ribose) which contain one or more mutations which render the FV protein APC resistant can be used to target these mutations into the Fv gene using ES cells or oocytes to create transgenic mice containin g genes encod ing APC resistant FV proteins [Strauss et al., supra].

VI. Screening Compounds For Anticoagulant Activity

The transgenic mice of the present invention which express APC resistant FV proteins provide animal models for human thrombophilia and provide a means to screen compounds for anticoagulant activity. As described in detail herein, transgenic animals expressing APC resistant FV proteins display spontaneous thrombosis. With regarding to transgenic animals homozygous for the R504Q mutation, approximately one-third to one-half of these homozygous mice die within the immediate postnatal period. Using that information, a screening method is performed utilizing a non-transgenic control group and a transgenic treatment group. Compounds to be tested for anticoagulant activity are administered to the same number of pregnant mice (generated using R504Q homozygote crosses) from the control group and the treatment group, and the survival of the pups used as a measure of efficacy. The compounds being tested can be administered using any suitable route (e.g., oral, parenteral, rectal, controlled-release transdermal patches and implants, etc.). Generally speaking, the route of administration will depend on the stability of the compound, the susceptibility of the compound to "first pass" metabolism, the concentration needed to achieve a therapeutic effect, and the like. Following initial screening, a compound that appears promising (i.e., which increases the number of pups which survive the imme diate postnatal period relative to the untreated control group) is further evaluated by administering various concentrations of the compound to transgenic animals in order to determine an approximate therapeutic dosing range.

The present invention also contemplates the use of other screening procedures to test compounds, including those presently used to evaluate anticoagulant compounds in other models. For example, survival differences or other pathologic changes in mature mice might provide an indication of efficacy. Pathologic changes like thrombus reduction can be compared between groups of test and control animals at various intervals following drug administration. [See, e.g., M. Barbanti et al., Thrombosis and Haemostasis 69(2): 147–51 (1993)].

Another screening method involves the crossing of the transgenic mice of the present invention with other pro-thrombotic mice. For example the R504Q mice are crossed with transgenic mice which overexpress the fibrinolytic inhibitor PAI-1 [Eitzman (1996) J. Clin. Invest. 97:232]; the resulting mice may result in easily observable survival differences in older animals. The offspring resulting from the crossing of R504Q and prothrombotic mice may also be used in a screening assay wherein thrombosis is experimentally induced. The induction of thrombosis may provide more dramatic differences between R504Q mice and wild-type mice, and thus the potential positive effect of a candidate anticoagulation therapy might be amplified. To illustrate, the induction of thrombosis might be performed by injection of endotoxin. It is expected that the transgenic mice will develop much more severe thrombosis in response to the endotoxin than normal mice, perhaps even at much lower doses. The animals are observed after treatment, in the presence and absence of the test compound, with thrombosis gauged either by crude survival or pathologic analysis for thrombus formation.

The animal testing may be supplemented and confirmed by testing on human subjects. However, the present animal models allow the testing of a large number of compounds, both by the methods described above and other methods known in the art, in a system similar in many important respects to that in humans.

EXPERIMENTAL

The following examples serve to illustrate certain preferred embodiments and aspects of the present invention and are not to be construed as limiting the scope thereof.

In the experimental disclosure which follows, the following abbreviations apply: ° C. (degrees Centigrade); ml (milliliter); μl (microliter); M (Molar); mM (millimolar); g (gram); μg (microgram); U (units), mU (milliunits); mim. (minutes); sec. (seconds); % (percent); kb (kilobase); PCR (polymerase chain reaction); Tris (tris(hydroxymethyl)-aminomethane); BSA (bovine serum albumin).

EXAMPLE 1

Conservation Of Factor V APC Cleavage Sites, Procoagulant Activity, And Resistance Of Factor V Mutants At APC Cleavage Sites To Cleavage By APC In order to determine whether the mouse is a suitable in vivo animal model for human factor V deficiencies, the evolutionary conservation in mouse and human factor V procoagulant activity and functional inactivation by APC were examined in murine wild-type and mutant factor V. This Example involved (a) cloning of murine Fv cDNA, (b) cloning of murine Fv genomic DNA, (c) expression of wild type and mutant murine Fv cDNAs and procoagulant activity of wild-type and mutant murine factor V proteins, and (d) APC resistance of wild-type and mutant murine factor V.

A. Cloning Of Murine Fv cDNA

A total of $5 \times 10^6$ [Suzuki et al., J. Biol. Chem. 257:6556, (1982)] clones from a C57BL/6J bone marrow cDNA library [J. Lowe, University of Michigan, Ann Arbor, Mich.; equivalent libraries may be obtained from a variety of commercial suppliers such as Stratagene, La Jolla, Calif. and Clonetech, Palo Alto, Calif.), in plasmid pCDM8 (Invitrogen), were screened by standard methods [Ginsburg et al., J. Clin. Invest. 78:1673, (1986)] using the full-length coding region of human Fv cDNA [Jenny et al., Proc. Natl. Acad. Sci. USA 84:4846, (1987)] as probe (the nucleotide sequence of the human Fv gene is provided in SEQ ID NO:26). Seven unique mouse cDNA clones were identified (mFV1–7, FIG. 1).

FIGS. 1A and B provide schematics of the murine factor V protein and cDNA structure, respectively. FIG. 1A depicts the murine factor V protein with the domain boundaries numbered above. The two putative APC cleavage sites at R305 and R504 in murine factor V are indicated by arrows. Factor V domains are labeled as A1–A3, B, and C1–C2. The Fv coding sequence (lower bar), was cloned from a C57BL/6J bone marrow cDNA library using the human Fv cDNA as probe. The major restriction enzyme sites used in the assembly are labeled on top of the bar [SacI (781), ApaI (1258), PstI (1834), NdeI (2073), KpnI (3976)]. ClaI and SalI cut the vector sequences adjacent to the Fv cDNA. The 7 unique cDNAs identified are shown as single lines and are labeled mFV1-7.

Figure 1B:
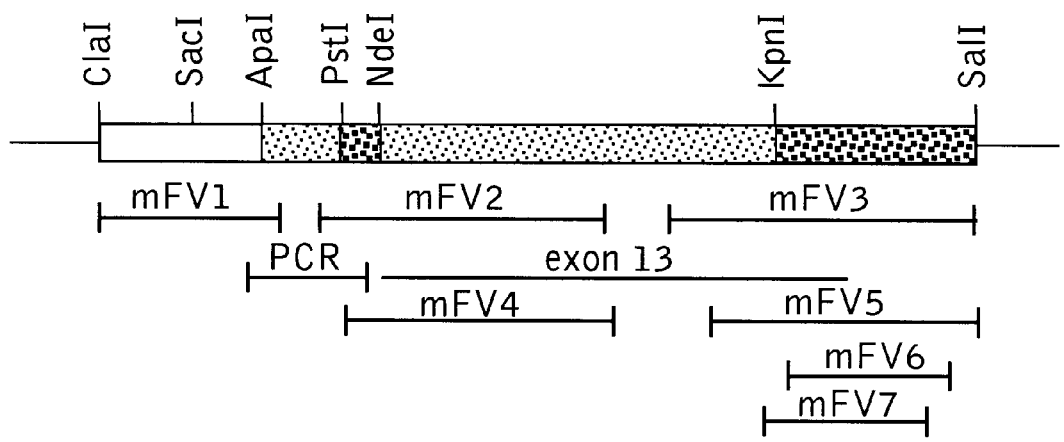

Additional sequence corresponding to the B domain was obtained from a 4.7 kb genomic NcoI fragment (designated as "exon13" in FIG. 1). An additional 275 bp from the A2 domain was obtained by reverse transcriptase PCR (RT-PCR) amplification of bone marrow and liver RNA templates obtained from a C57BL/6J X DBA mouse (available from Charles River Laboratories, Wilmington, Mass. or Jackson Laboratories, Bar Harbor, Me.). For RT-PCR, total RNA was isolated from mouse liver and bone marrow using the Trizol kit (BRL, Gaithersburg, Md.), according to the manufacturer's instructions. First strand cDNA synthesis was performed with AMV reverse-transcriptase (Boehringer Mannheim Biochemicals, BMB, Indianapolis, Ind.) and a primer [(5'-CTGGAGAAAGGGACACC-3') (SEQ ID NO:1)] which is complementary to exon 13 sequence at 42° C. for 1 hour, followed by PCR amplification using primers corresponding to sequences within exons 7 (5'-TCATAGC CGCAGAGGAGGTCA-3') (SEQ ID NO:2) and 12 (5'-ATGGGGAACAGGGTCAAG GTG-3') (SEQ ID NO:3). Bone marrow and liver experiments were performed independently; two bone marrow and three liver-derived clones were sequenced and found to be identical (clone labeled "PCR", FIG. 1). The overlapping clones are shown in FIG. 1.

The complete coding portion of the murine Fv cDNA (6552 bp) was cloned, and its sequence was determined on both strands (this sequence has been submitted to GenBank and assigned Accession No. US52925. The nucleotide sequence (SEQ ID NO:4) the murine Fv cDNA and deduced amino acid sequence (SEQ ID NO:5) of murine factor V are shown in FIG. 2. The nucleotide sequence is shown with the predicted amino acid sequence below in single letter code. The nucleotides are numbered at right and the amino acids are numbered at left. The initiation codon, stop codon, and polyadenylation signals are shown in bold and are underlined. The locations of the exon junctions are indicated by arrow heads. The sequence in the vicinity of the initiation codon fits the consensus described by Kozak [Kozak, J. Biol. Chem. 266:19867, (1991)]. A standard polyadenylation signal follows immediately after the termination codon (ATTAAA). Sequences located immediately 3' of the stop codon (TAG) in the Fv gene are provided in SEQ ID NO:54. The murine Fv cDNA encodes a 2183 amino acid protein which includes a 28 amino acid signal peptide, followed by the mature protein of 2155 amino acids.

Figure 3:
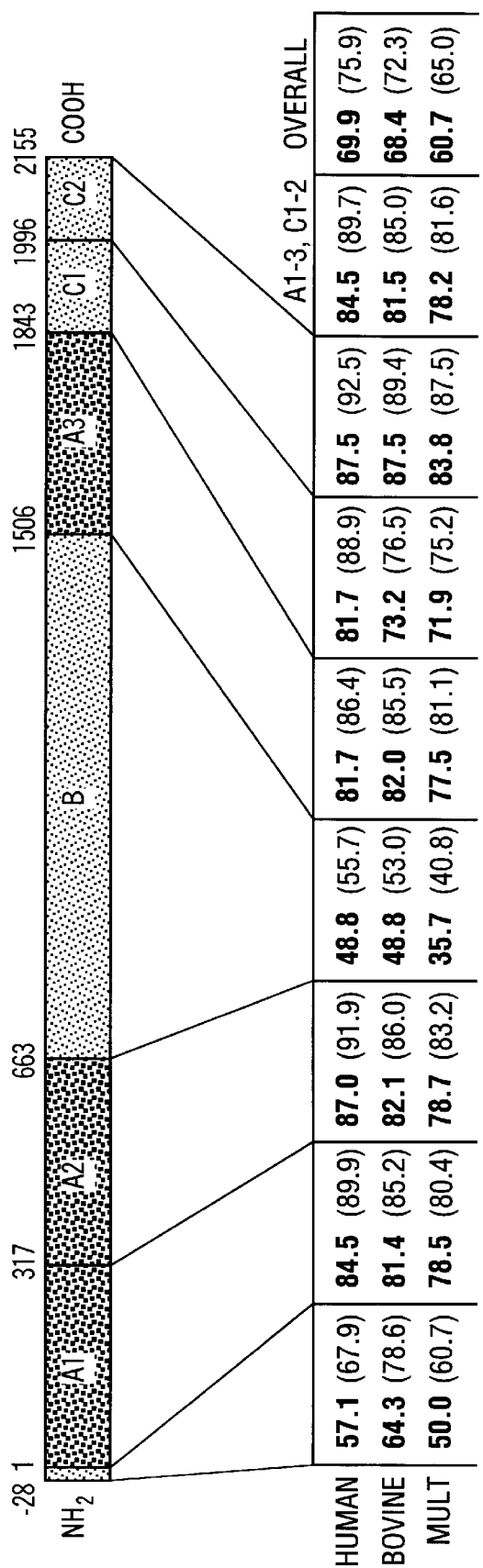
FIG. 3 shows a comparison between mouse, human and bovine factor V amino acid sequences within domains of the factor V protein.

An alignment of the predicted amino acid sequence for murine factor V with the human [Jenny et al., supra (1987); Cripe et al., Biochemistry 31:3777, (1992)] and bovine [Guinto et al., J. Biol. Chem. 267:2971, (1992) factor V sequences is shown in FIG. 3. The human factor V amino acid sequence ("Human"), and the bovine factor V amino acid sequences (Bovine) were compared pairwise against the murine factor V sequence, or simultaneously with the murine sequence ("Mult") with the MegAlign computer program (LaserGene, DNAStar, Madison, Wis.) using the Clustal method. The numbers on top of the bar indicate the domain boundaries in murine factor V, deduced from sequence comparison with the human and bovine proteins. Values for each domain are the percentage amino acid identity, with the percentage amino acid similarity shown in parentheses. This alignment demonstrates that the functionally important A1–A3 and C1–C2 domains are highly conserved (>84% sequence identity between murine and human, and 60% overall amino acid identity among the human, bovine and murine factor V sequences) (FIG. 3). In contrast, only 35% identity among all three species is observed for the poorly conserved B domain. A similar high degree of inter-species divergence has been noted for the factor VIII B domain which is also poorly conserved in homology comparison between factor V and factor VIII.

These results suggest that the B domain may serve primarily a spacer function, with little selective pressure to conserve a specific amino acid sequence. In agreement with this, it has been shown that factor V and factor VIII lacking B domain sequences [Keller et al., Biochemistry 34:4118, (1995); Pittman et al., Blood 84:4214, (1994)] retain procoagulation activity.

The murine factor V protein is 41 amino acids shorter than human factor V. This difference is due primarily to missing nucleotides in the murine B domain. A number of distinct structural features noted in the human factor V B domain [Jenny et al, supra (1987)] are also conserved in the mouse. Human factor V contains 37 potential N-glycosylation sites, with 25 located in the B domain. By comparison, murine factor V contains 27 potential N-glycosylation sites, with 17 located in the B domain. This number of N-glycosylation sites is closer to that of bovine factor V, where there are 28 total sites with 18 in the B domain. Thus, the B domain appears to be a consistent site for extensive glycosylation.

The human factor V B domain contains two tandem repeats of a 17 amino acid sequence and 31 tandem repeats of a nine amino acid motif. Bovine factor V contains only one 17 amino acid repeat and 29 copies of the 9 amino acid motif [Guinto et al., J. Biol. Chem. 267:2971, (1992)]. The 17 amino acid repeats are deleted from the mouse sequence and the nine amino acid motif is only present in 25 copies. Differences in these repeat sequences account for nearly all of the variation in length (39 of 41 amino acids) between human and murine factor V.

FIG. 4 shows a cross species alignment of factor V sequences (SEQ ID NOS:6–25) in the vicinity of APC cleavage sites (FIG. 4A) and thrombin cleavage sites (FIG. 4B). The arrow indicates the cleavage site in both FIG. 4A and FIG. 4B. Cleavage sites are aligned relative to the human factor V protein and are indicated in parentheses.

This alignment shows that the arginine residues at all thrombin and APC cleavage sites are conserved between human, murine, and bovine factor V, except at the R679 APC cleavage site where a lysine substitution was observed in the bovine sequence (FIG. 4A).

B. Cloning Of Murine Fv Genomic DNA

Using a 1128 bp PstI fragment (nucleotides 1159–2287 of SEQ ID NO:26) of human cDNA [Jenny et al., supra] as probe, two λ phage clones, spanning at least exons 7–13 of the Fv gene, were isolated from an 129Sv genomic library (Stratagene, La Jolla, Calif.). The portion of the Fv gene contained within these genomic clones (~30 kb; the entire Fv gene is estimated to be 80–90 kb) was mapped by restriction enzyme digestion and polymerase chain reaction (PCR) [Sambrook et al., Cold Spring Harbor, N.Y., Cold Spring Harbor Laboratory Press, (1989)], and the intron-exon junctions were determined by DNA sequencing (SEQUENASE 2.0, United States Biochemical, Cleveland, Ohio) using primers based on the murine Fv cDNA sequence. Exon 8 primer 5'-CTGTTATCAGAGCCCAGGTC-3' (SEQ ID NO:27); exons 9 and 10 primers 5'-GGAGAGAAGGTCACCCCGTG-3 (SEQ ID NO:28), 5'-CTTCTCTCCTT ACGAAGATG-3' (SEQ ID NO:29) and 5'-CCTAATCTGTGCCAGCG-3' (SEQ ID NO:30); exon 11 primers 5'-CTCTTGTTCTCGTCAAACAC-3' (SEQ ID NO:31) and 5'-TTGAGGACAACATCAACAAG-3' (SEQ ID NO:32); and exon 12 primer 5'-TGC CACTGGACAGTGTCATC-3' (SEQ ID NO:33). Introns were amplified by PCR, and intron size determined by comparison to a 1 kb ladder DNA marker standard.

Intron length and exon-intron junction sequences were determined for introns 7, 8, 9, 10, 11, and 12. The cloned intron sequences for the 3' end of intron 8 (SEQ ID NO:34), the 5' end of intron 8 (SEQ ID NO:35), intron 9 (SEQ ID NO:36), the 5' end of intron 10 (SEQ ID NO:37), the 3' end of intron 10 (SEQ ID NO:38), the 5' end of intron 11 (SEQ ID NO:39), and the 3' end of intron 12 (SEQ ID NO:40) are shown in FIG. 5. The splice junctions for all six introns are shown in Table 1.

TABLE 1

Murine Fv Gene Intron-Exon Splice Junctions

| Intron | Exon | Intron | Exon | Intron size(bp) | Splice phase |
|---|---|---|---|---|---|
| 7 | GACAA | GTGAGTTG ... TCCCTTAAAG | AATTT | 1018 | II |
| 8 | TCAAG | GTAAGCAA ... AACTTTCTAG | ATCGT | 1462 | 0 |
| 9 | CTCAG | GTGGGAAC ... TTTCTTCCAG | GCAGT | 304 | I |
| 10 | TACAG | GTATTTTA ... TCCCCTGCAG | AGGGT | 1614 | 0 |
| 11 | GAGCA | GTAAGTCA ... CCTCCTTCAG | CTATC | 1659 | I |
| 12 | TGTTG | GTGAGTAA ... TCTTATGAAG | GAACT | 1592 | I |
|  | AR | Consensus[1]<br>GTRAGTYYYYYYNYAG |  |  |  |

[1]R represents A/G; Y represents C/T.

These splice junctions show perfect agreement with the GT ... AG consensus (Table 1) [Mount, Nucleic Acids Res 10:459, 1982]. The intron size (Table 1) was determined by PCR. Comparison of the murine gene to the published human genomic sequence [Cripe el al., Biochemistry 31:3777, (1992)] demonstrated perfect conservation of splice junctions relative to the Fv coding sequence, including intron phase (Table 1). The size of these introns is also roughly conserved, with the smallest murine intron in this region (intron 9, 304 base pairs), also being one of the smallest introns in human Fv (600 base pairs). As for the human Fv and Fviii gene, the entire B domain of murine Fv is encoded in one exon (exon 13).

These results demonstrate the perfect conservation of splice junctions relative to the Fv coding sequence, and the high degree of conservation of Fv intron size between mouse and human.

C. Expression Of Wild-Type And Mutant Murine Fv cDNAs And Procoagulant Activity Of Wild-Type And Mutant Murine Factor V Proteins In order to compare the activity of wild-type mouse factor V, and mouse factor V containing a mutation at the APC binding sites, mutations to glutamine at positions Arg 305 and Arg 504 (corresponding to R306 and R506 in human factor V) were introduced by site directed mutagenesis into wild-type mouse Fv cDNA. The full length Fv cDNA was then assembled and cloned into the expression vector pCMV5 [Andersson et al., J. Biol. Chem. 264:8222, (1989); pcDNA I/Amp (Invitrogen) may also be used] and the assembled wild-type and mutant cDNAs were transfected into COS-1 cells (ATCC CRL2650). The procoagulant activity of the expressed proteins was then measured. These steps were performed as follows.

1. Site-Directed Mutagenesis

A SacI-PstI fragment (nucleotides 781–1834, FIG. 1) of the murine Fv cDNA, containing both putative APC cleavage sites (R305 and R504) was cloned into pSELECT-1 (Promega, Wis.), and the mutations R305Q, R504Q, or both mutations in cis were introduced by site-directed mutagenesis (Muta-Gene in vivo mutagenesis kit, Bio-Rad, Hercules, Calif.), following the manufacturer's instructions. The mutagenesis oligonucleotides were 5'-CCAAAGAAAACGCAGAGCCCCAAGACC-3' (SEQ ID NO:41) (R305Q) and 5'-CCTGGACCAGCAGGGTGTACAG-3' (SEQ ID NO:42) (R504Q), in which the underlined nucleotides represent the mutations. In each case the mutagenized sequences (CA.) replaced AG in the wild type sequence. The presence of the desired mutations was confirmed by DNA sequencing using SEQUENASE 2.0 (United States Biochemical, Cleveland, Ohio).

2. Assembly And Cloning Of The Wild-Type And Mutant Fv cDNAs

The full length Fv cDNA was assembled in an eight step procedure from five different clones into the expression vector pCMV5 as a ClaI-SalI fragment (FIG. 1). The plasmid vector pCMV5 [Andersson et al., supra (1989)] contains the cytomegalovirus (CMV) promoter, and the human growth hormone (hGH) intron and polyadenylation signals. The 5' end of the Fv cDNA to the ApaI site (1–1263) was derived from clone mFV1; the second fragment, ApaI-PstI (1263–1839), was from clone "PCR" (described in Example 1); the third fragment, PstI-NdeI (1839–2078), was from clone mFV2; the fourth fragment, NdeI-KpnI (2078–3981), was from the exon 13 genomic clone; and the last fragment, from Kpn1 to the 3' end (3981–6585), was taken from clone mFV3 (FIG. 1). The mutations were first introduced into the SacI-PstI fragment (786–1839, FIG. 1), and both wild-type and mutant cDNAs were then assembled in parallel. The integrity of junction regions in each construct was confirmed by DNA sequencing using SEQUENASE 2.0 (United States Biochemical, Cleveland, Ohio).

3. Transient Transfection Of COS-1 Cells

COS-1 cells grown in DMEM medium containing 10% serum in a 100-mm plate were transfected with 10 μg of plasmid expression vectors carrying wild-type murine Fv cDNA (pFV-WT), and mutants at the R305 (pFV-R305Q) and R504 (pFV-R504Q) APC cleavage sites as well as the double mutant (pFV-R305Q:R504Q) by calcium phosphate precipitation [Chen et al., Mol. Cell. Biol. 7:2745, (1987)]. Following the addition of DNA, the transfected cells were grown for 24 hours in DMEM medium containing 10% serum, and the medium was then replaced with 3-ml serum-free OPTI-MEM I media (BRL, Gaithersburg, Md.). Following the addition of the OPTI-MEM I mcdia, the cells were grown for another 48 hours before harvesting the conditioned medium.

4. Procoagulant Activity Of The Wild-Type And Mutant Factor V Proteins

The factor V procoagulant activity in the conditioned media of transfected COS-1 cells was measured by reconstitution of human factor V deficient plasma. The conditioned media were harvested and diluted 1:5 in dilution buffer (Pharmacie Heper, Franklin, Ohio), and assayed for factor V activity. Samples (50 μl) were mixed 1:1 with human factor V-deficient plasma (George King Bio-medical, Inc. Overland Park, Kans.), and warmed at 37° C. for 3 minutes. Pre-warmed thromboplastin (Sigma, St. Louis, Mo.) with 25 mM $CaCl_2$ (100 μl) was then added, and the time to clot formation was measured in an MLA Electra 750 coagulation timer. A standard curve was generated using dilutions of pooled normal human plasma (George King Bio-medical, Inc., Overland Park, Kans.).

Using normal human plasma as standard, the conditioned media from COS-1 cells expressing wild-type and all mutants were found to contain similar factor V clotting activities (ranging from 450 mU/ml to 650 mU/ml). These results demonstrate that the introduction of these mutations does not appear to affect factor V procoagulant function, consistent with observations for the corresponding human native and recombinant factor V proteins [Nicolas et al., J. Biol. Chem. 270:21158, (1995); Heeb et al., Blood 85:3405, (1995); Camire et al., J. Biol. Chem. 270:20794, (1995)]. These results also demonstrate that murine factor V efficiently complements human factor V function in plasma.

D. APC Resistance Of Wild-Type And Mutant Murine Factor V

The recombinant murine factor V proteins (which were generated as described above) were assayed for susceptibility to APC inactivation using standard methods. Briefly, wild-type and mutant factor V conditioned media were obtained as described above, and concentrated 3–5 fold using Centricon-30 concentrators (Amicon) to yield preparations with 500–1000 mU/ml factor V activity and activated using thrombin with 25 mM calcium (11 U/ml) (Sigma, St. Louis, Mo.). Complete activation was usually obtained within 5 minutes (FIG. 6) at which time (designated t=0), 0.1 μg/ml human APC (Enzyme Research Labs Inc., South Bend, Ind.), 100 μg/ml phospholipid vesicles (P. J. Fay University of Rochester, Md.; phospholipid vesicles can be obtained from standard clinical kits sold for measuring clotting activity) and 5 mM $CaCl_2$ were added to initiate factor Va inactivation by APC. Samples were taken at various time points, diluted 50 fold in 50 mM Tris (pH 7.3), 0.2% BSA, and immediately assayed for factor V activity. Factor V activity was determined as described above except 100 μl of the sample was incubated with 100 μl of human factor V deficient plasma and 100 μl thromboplastin with 25 mM calcium (Sigma, St. Louis, Mo.) for 3 minutes, then 100 μl of 25 mM $CaCl_2$ was added and the time to form a clot was determined.

Figure 6:
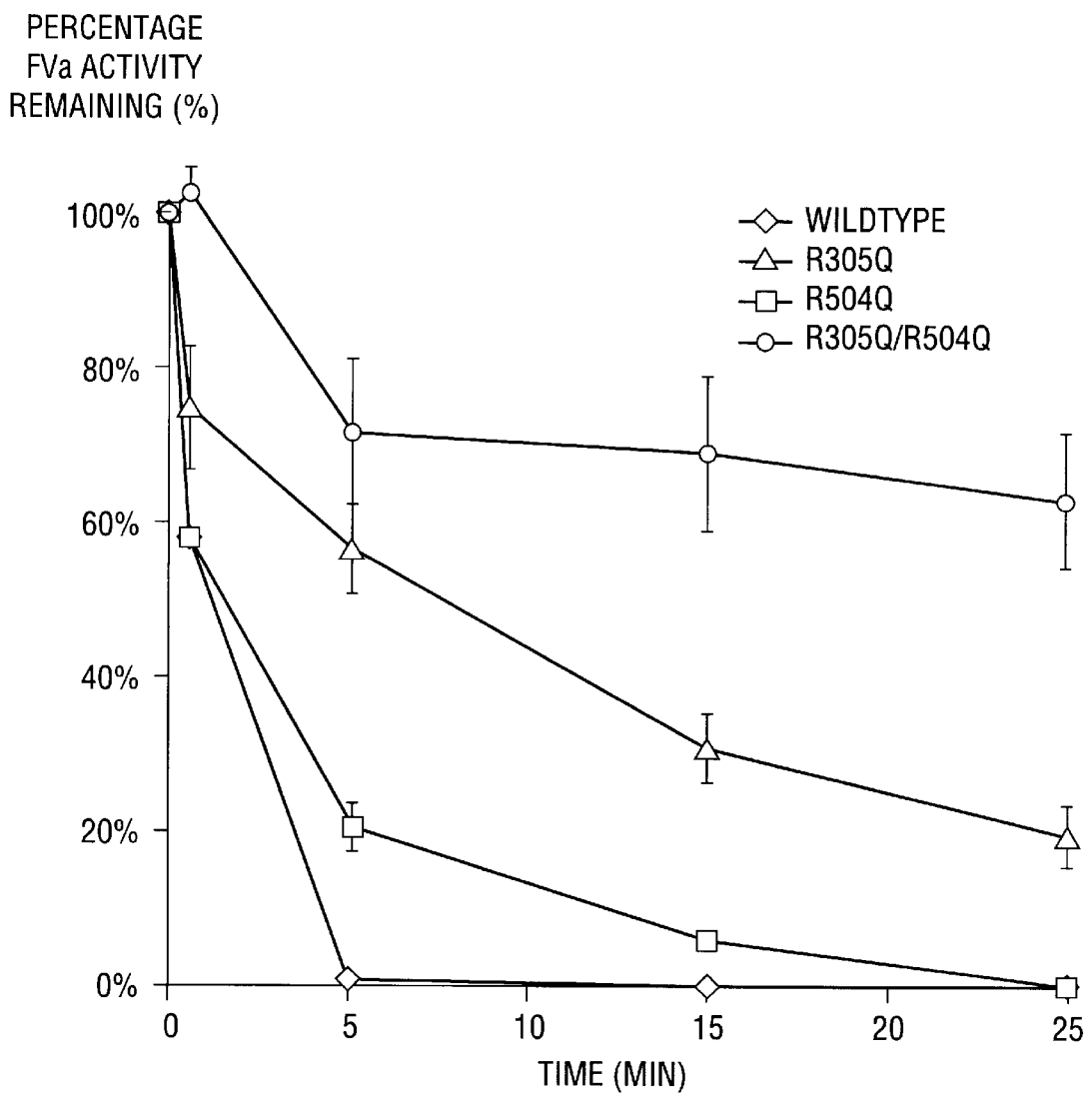
FIG. 6 shows the APC resistance of recombinant wild-type and mutant (R305Q, R504Q and R305Q/R504Q) murine factor V.

The results of the APC resistance of recombinant wild-type and mutant murine factor V are shown in FIG. 6. Each point represents the average of the activity measured in conditioned media from three independent transfections. APC was added to the reactions at t=0 (t, time). The (◊) represents wild-type factor V, (Δ) represents factor V R305Q, (□) represents factor V R504Q, and (○) represents factor V R305Q/R504Q. Wild-type recombinant murine factor V was completely inactivated by t=5 minutes (FIG. 6). In contrast, introduction of a single mutation at R305Q or R504Q resulted in partial resistance to APC. The double mutant (R305Q/R504Q) was markedly resistant to APC inactivation, retaining ~70% of its initial peak activity at t=25 minutes (FIG. 6). Without limiting the invention to any particular mechanism, the initial rapid decrease in activity in the R305Q/R504Q double mutant may be due to residual interaction with APC. These results are very similar to those observed with native and recombinant human factor Va proteins [Nicholas et al., supra; Heeb et al., supra; Camire et al., supra].

Taken together, the data obtained in this Example demonstrate the maintenance of very similar factor V structure and function across species, as well as a strong conservation of the factor V/APC interaction among mammalian species. The location of APC cleavage sites is conserved, and similar resistance to APC was obtained with mutations at these sites. In addition to the conservation of resistance to APC cleavage, factor V procoagulant functions is also highly conserved. This high degree of structural and functional conservation between human and murine factor V in both procoagulant and APC anticoagulant function demonstrates that the mouse is an appropriate in vivo model for human factor V deficiencies.

EXAMPLE 2

Generation Of Fv Null Transgenic Mice By Gene Targeting Through Homologous Recombination Fv null transgenic mice were generated using the technique of homologous recombination in embryonic stem cells. A targeting vector containing large fragments of Fv genomic sequence flanking a selectable marker (the neo gene) was employed. The homologous recombinants contain a deletion in exons 8–11 of the Fv gene and an insertion of the neo gene. This recombination event resulted in a frame shift near the N-terminus of factor V which led to a complete loss of factor V. Embryonic stem cells containing this targeted deletion were used to generate transgenic mice which were then bred to homozygosity. This Example involved (a) construction of the targeting vector, (b) transfection of embryonic stem cells, (c) generation of transgenic Fv null mice, and (d) characterization of transgenic mice containing a disrupted Fv gene.

A. Construction Of The Targeting Vector

Figure 7:
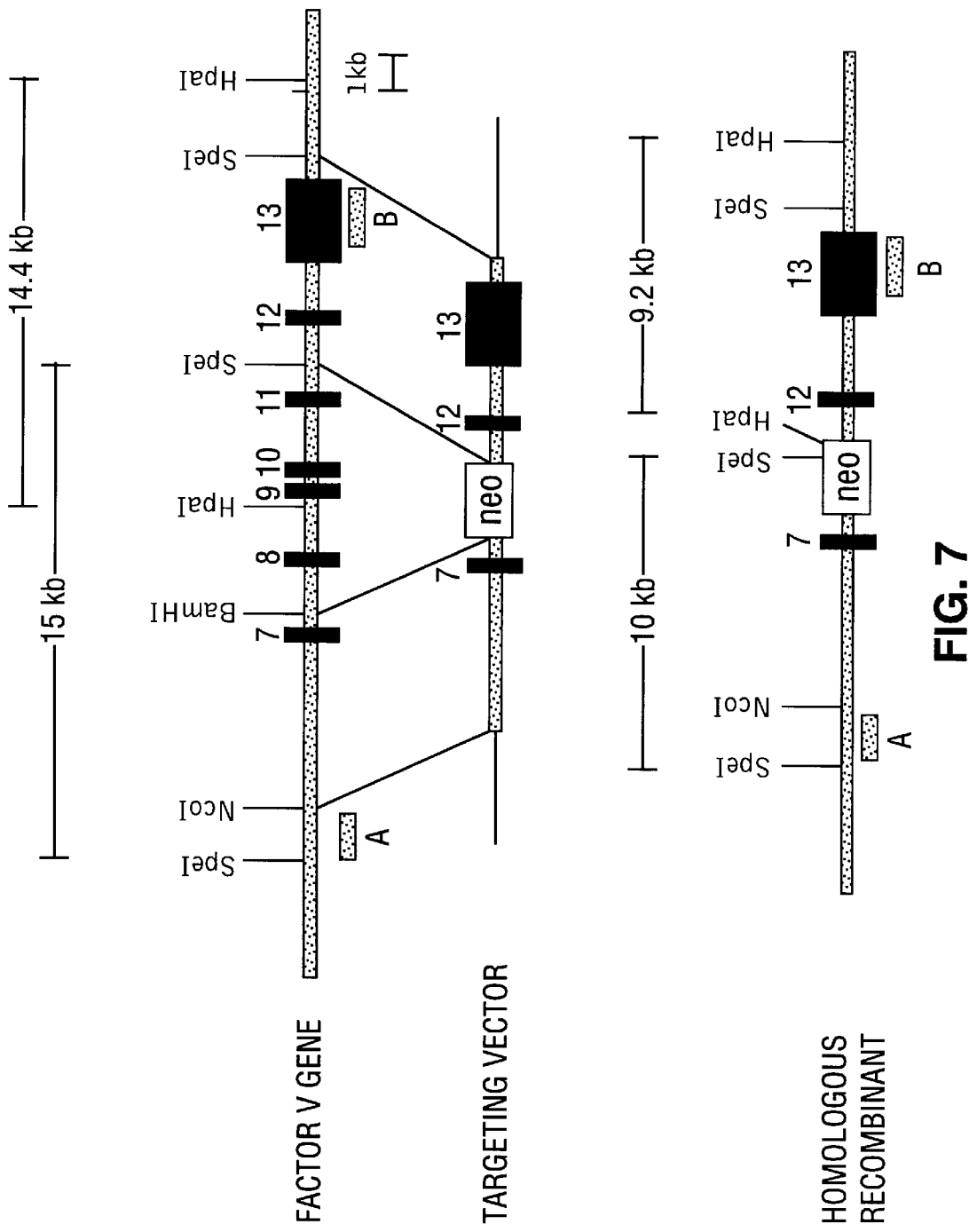
FIG. 7 shows a schematic representation of the targeting of the Fv gene by homologous recombination to generate a disrupted Fv allele.

For the construction of the Fv targeting vector, λ phage clones spanning ~30 kb of mouse Fv genomic sequences isolated as described in Example 1 from a 129SV genomic library (Stratagene, La Jolla, Calif.) and using exons 7–12 (FIG. 2) were used. The strategy for the generation of the targeting vector is schematically shown in FIG. 7. FIG. 7 shows the structure of exons 7–13 of the murine Fv gene and targeting vector. The targeting vector contains a neo cassette, which replaces murine exons 8–11 flanked by ~6.6 kb homologous 5' and 3' arms. The neo cassette is driven by the pgk promoter [Zheng et al, Proc. Natl. Acad. Sci. USA 92:12426–12430 (1995)]. The predicted product of successful homologous recombination is shown at the bottom of FIG. 7. The location of hybridization probe A [a 1.3 kb SpeI-NcoI fragment of murine Fv genomic sequence] and probe B [a 2.3 kb PCR fragment specific to exon 13 generated using the primers 5'-TGTTCTGTAGGGGTCAT-3' (SEQ ID NO:43), and 5'-TCACTGCTCTCGCTCTG-3' (SEQ ID NO:44)] used to detect successful targeting, are indicated in FIG. 7. The mutant allele carries additional SpeI and HpaI sites within the neo cassette.

The targeting vector was constructed by assembling a 6.7 kb NcoI-BamHI 5' Fv genomic fragment, a 1.4 kb BamHI-XbaI fragment containing a neomycin (neo) expression cassette driven by the pgk-promoter and a 6.6 kb SpeI-SpeI 3' fragment of the Fv gene, all cloned into the plasmid vector pSL301 (Invitrogen, San Diego, Calif.).

B. Transfection Of Embryonic Stem Cells

The targeting vector was linearized with SfiI, introduced into the 129SV-derived D3 [T. Doetschman, University of Cincinnati; Zheng et al., Proc. Natl. Acad. Sci. USA 92:12426–12430 (1995)] and CJ7 [Swiatek et al., Genes Dev. 7:2071–2084 (1993)] ES cell lines by electroporation, and stable transfectants selected as described [Zheng et al., supra]. Briefly, ES cells were grown on mitomycin C-treated primary murine embryonic fibroblast (MEF) feeder layers in DMEM supplemented with 15% fetal calf serum (HyClone), 0.1 mM 2-mercaptoethanol, 50 units of penicillin per ml/50 µg of streptomycin per ml and 1000 units of leukemia inhibitory factor per ml (GIBCO). G418-resistant MEF cells were prepared from mice transgenic for a Neo expression cassette.

Twenty-five micrograms of plasmid DNA linearized with SfiI was mixed with $1 \times 10^7$ ES cells in 0.6 ml of culture medium, electroporation was performed in a Bio-Rad Gene Pulser (320 V, 250 µF), and cells were plated on a feeder layer of G418-resistant MEF cells at a density of $5 \times 10^6$ cells per 100-mm plate. After 24 hours, G418 was added to the culture medium. At day 8–9, G418-resistant colonies were picked into 96 well plates and expanded.

Individual ES clones were screened for homologous targeting by Southern blot analysis using probes A and B (FIG. 7). Recombination in both arms of the construct resulted in replacement of Fv exons 8–11 by the neo-cassette introducing a frameshift mutation near the N-terminus of factor V, which was predicted to lead to a complete loss of function.

Figure 8:
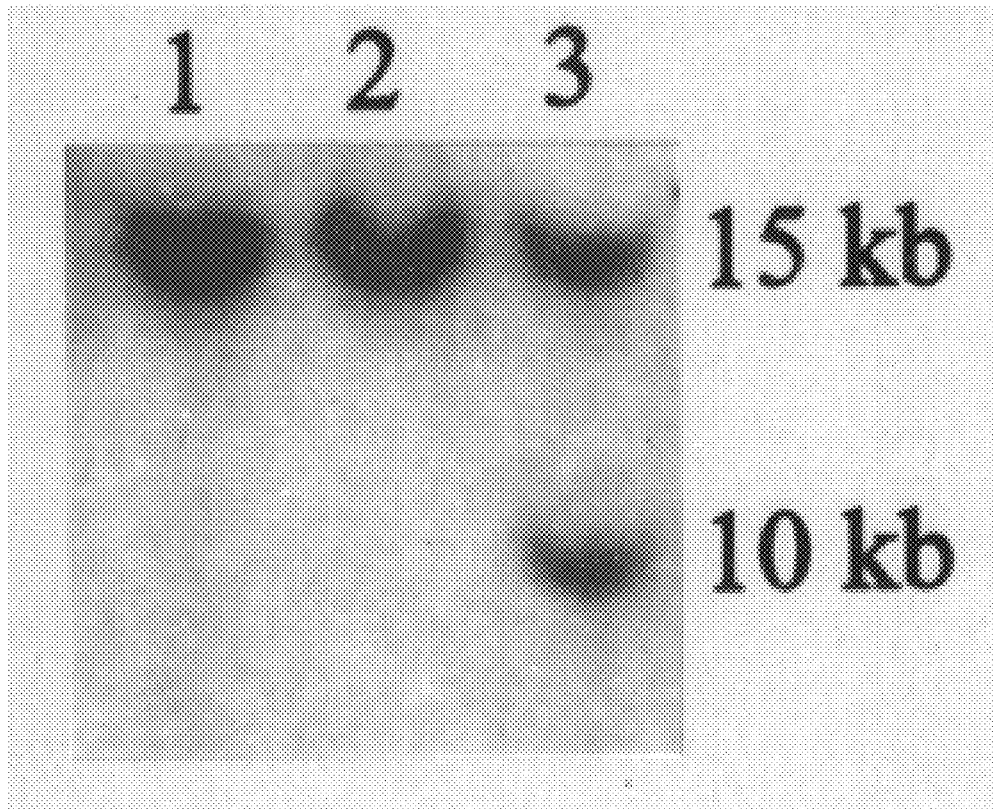
FIG. 8 shows the results of Southern blot analysis of DNA extracted from stem cells and digested with SpeI.

Southern blot analysis of SpeI-digested ES cell DNA is shown in FIG. 8. The Southern probe A (described above) detected a 15 kb SpeI fragment from the intact endogenous Fv gene and a 10 kb fragment from the successfully targeted Fv gene, due to the introduction of an SpeI site within the neo-cassette. Lanes 1 and 2 contain DNA from ES cell clones carrying only the 15 kb endogenous Fv gene (i.e., controls). Lane 3 contains DNA from a successfully targeted ES clone carrying both the 15 kb endogenous allele and the 10 kb targeted Fv allele. Approximately 10 of 100 neo-resistant ES cell clones carried the targeted Fv deletion, thus giving a targeting efficiency of 10%.

C. Generation Of Transgenic Fv Null Mice

Eight independent ES clones (seven from D3 and one from CJ7) which carried the targeted Fv deletion were injected into mouse E3.5 blastocysts from C57BL/6J mice (Jackson Laboratory, Bar Harbor, Me.) and transplanted into pseudo-pregnant females using standard techniques [Zheng et al., Proc. Natl. Acad. Sci. USA 92:12426–12430 (1995)]. Chimeric mice derived from these blastocysts were mated with C57BL/6J mice. Heterozygous mice derived from the original injected ES cells were obtained from these crosses, indicating successful germline transmission.

Figure 9A:
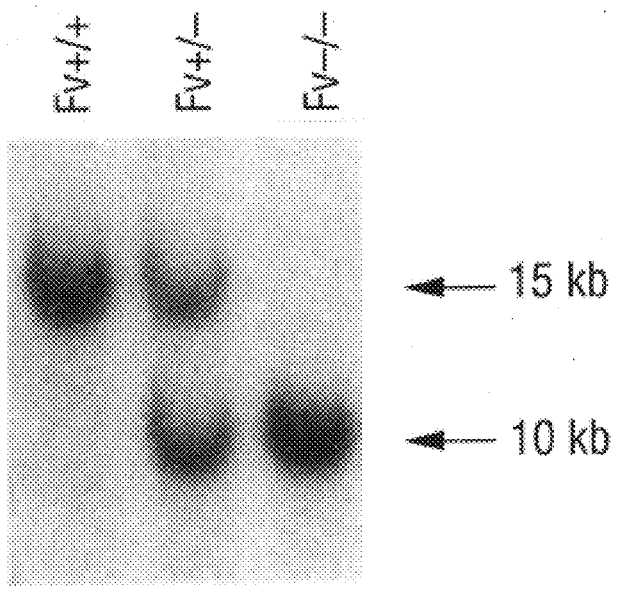
FIGS. 9A and B show the results of Southern blot analysis of genomic DNA isolated from Fv+/+, Fv+/−, and Fv−/− transgenic mice.
Figure 9B:
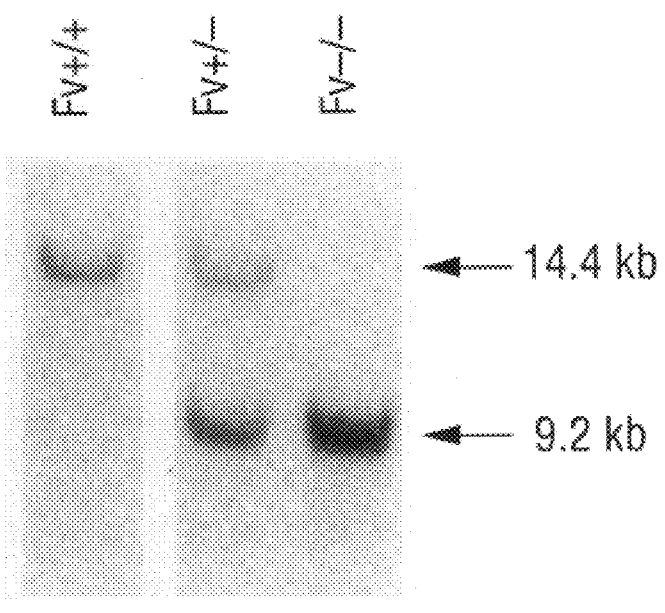

F1 mice heterozygous for the targeted allele (Fv+/−) were intercrossed to generate homozygous Fv null progeny. Genotypes of mice were established using DNA prepared from tail biopsies analyzed by either Southern blotting analysis as described above, or PCR. Southern blot analysis demonstrating the expected genomic structure at the 5' end of the locus is shown in FIG. 9A, and at the 3' end in FIG. 9B. Genomic DNA prepared from tail biopsies of Fv+/+, Fv+/−, and Fv−/− was analyzed by restriction digestion with SpeI and hybridization with probe A (FIG. 9A), or restriction digestion with HpaI and hybridization with probe B (FIG. 9B). The Southern blots of FIG. 9 show that novel genomic fragments of the expected size (10 kb and 9.2 kb) were seen in the Fv+/− and Fv−/− mice, and that the normal allele (15 kb and 14.4 kb) was absent from Fv−/− mice. In FIG. 9A, DNA from a homozygous wild type mouse Fv+/+, showed only the endogenous 15 kb SpeI fragment from the intact Fv gene. DNA from a heterozygous mouse Fv+/− showed both the 15 kb endogenous and the 10 kb targeted allele. The DNA from a homozygous null mouse Fv−/−, showed only the 10 kb targeted allele.

In the PCR assay, the wild-type and targeted Fv alleles were distinguished using primers specific for exon-10 of the murine Fv gene [5'-ACGATCAGACCAGTT CAACC-3' (SEQ ID NO:45) and 5'-CCTTGTAACGTCCACATCAC-3' (SEQ ID NO:46)] and the neo gene [5'-GGACTGGCTGCTATTGGGCGAAGTG-3' (SEQ ID NO:47) and 5'-GAAGAACTCGTCAAGAAGGCGATAGAAGG-3' (SEQ ID NO:48)].

Genotypes of progeny from Fv+/− intercrosses were analyzed at varying stages and the results are shown in Table 2. Statistical significance was calculated using the $\chi^2$ test to compare the observed and expected frequencies.

TABLE 2

Genotypes Of Progeny From Fv +/− Intercrosses At Various Stages

|  | Total | +/+ | +/− | −/− |  |
|---|---|---|---|---|---|
| Term Pups | 297 | 89 (30.0%) | 176 (59.2%) | 32 (10.8)% | $p < 1 \times 10^4$ |
| E18.5 | 109 | 37 (34.0%) | 60 (55.0%) | 12 (11.0%) | $p < 0.002$ |
| E15.5 | 110 | 32 (29.1%) | 65 (59.1%) | 13 (11.8%) | $p < 0.01$ |
| E11.5 | 72 | 20 (27.8%) | 41 (56.9%) | 11 (15.3%) | $p \sim 0.16$ |
| E10.5 | 141 | 31 (22.0%) | 76 (54.0%) | 34 (24.0%) | $p > 0.5$ |
| E9.5 | 137 | 36 (26.2%) | 62 (45.3%) | 39 (28.5%) | $p > 0.5$ |
| C57BL/6J Background | | | | | |
| Term Pups | 117 | 36 (30.8%) | 69 (59%) | 12 (10.3%) | $p < 0.002$ |
| E18.5 | 50 | 20 (40%) | 23 (46%) | 7 (14%) | $p < 0.03$ |

The expected Mendelian ratio of genotypes is 25% wild-type (+/+), 50% heterozygous (+/−), and 25% homozygous Fv null (−/−). DNA analysis of approximately 300 progeny mice at term, derived from an intercross of Fv+/− mice, identified a highly significant decrease in the observed number of Fv−/− progeny, compared to the expected 25% frequency. The surprising decrease in the observed number of Fv−/− term pups suggests that ~½ of the homozygous null mice were either being lost around the time of birth or dying during embryonic development. Analysis of DNA obtained from embryos at multiple time points demonstrated that fetal loss was occurring before E11.5 (Table 2). Although the expected number of Fv−/− embryos were present at E10.5 and E9.5, a decrease was evident by E11.5, with highly significant differences observed at E15.5 and E18.5 (Table 2). Approximately ½ of the Fv−/− embryos were lost after E10.5 with the remaining half surviving to term.

In order to exclude a contribution from a strain-specific modifier gene to the observed phenotypes, a four generation backcross of Fv+/− mice to C57BL/6J was performed. The results of an intercross between Fv+/− mice derived from four successive backcrosses to C57BL/6J are shown in Table 2 under the heading "C57BL/6J background". The distribution of genotypes among progeny showed a similar decrease in the number of observed Fv−/− mice at term (12/117) [10.3%]) and at E18.5 (7/50 [14%]). The Fv−/− offspring surviving to term all developed similar, fatal perinatal hemorrhage within the first few hours of birth. In addition, the original chimeric founders were backcrossed to 129SV to produce Fv+/− mice on a pure 129SV background. Analysis of an intercross between these 129Sv Fv+/− mice identified only 3/26 [11.5%] Fv−/− progeny at E18.5, consistent with the patterns observed on the C57BL6/J background, as well as the original intercross. These results provide strong evidence against a C57BL/6J or 129SV-specific modifying gene(s) as the explanation for the approximately equal distribution of the Fv−/−embryonic and perinatal lethal phenotypes.

To detect a potential sex-limited modification of the embryonic lethal phenotype, 15 Fv−/− term pups were typed by PCR for the Y-chromosome-specific sequence Sry [Han et al., J. Assist. Reprod. Genet. 10:151–156 (1993)]. Eight pups were identified as male and 7 as female, thus excluding a modifying effect of the sex chromosomes as the explanation for this unexpected survival data.

1. Gross Morphology And Histology

Fv-deficient animals were immediately evident at birth and generally died within 2 hours of birth due to massive intra-abdominal hemorrhage. Cutaneous bleeding, particularly over the head, was occasionally evident and scattered microscopic hemorrhages were detected in a variety of tissues. No other gross or microscopic abnormalities were identified. One of 60 homozygous null pups survived until day 10 and a second pup died immediately following a tail biopsy at day 14.

The fatal neonatal hemorrhage observed in Fv−/− mice was unexpected, given the much milder phenotype associated with human factor V deficiency [Tracy et al., Hum. Pathol. 18:162–169 (1987)]. The severity of the defect observed in these animals also contrasts with the phenotype of afribrinogenemic humans [Galanakis, Hematol. Oncol. Clin. North Am. 6:1171–1187 (1992)] and fibrinogen knockout mice [Suh, et al., Genes Dev. 9:2020–2033 (1995)]; both generally survive into adulthood.

By E9.5, Fv+/+ and Fv+/− embryos (and approximately 60% of Fv−/− embryos) had 20–25 somites, with a well developed heartbeat and yolk sac circulation. However, 17/43 Fv−/− E9.5 embryos demonstrated some degree of developmental delay, many having only 12–16 somites. Embryos were photographed at autopsy, fixed in 1% glutaraldehyde in 0.1 M phosphate buffer for 1 hour at room temperature, embedded in paraffin and sectioned at 6 micrometers [Kaufman, Academic Press, Inc. New York, (1992)]. Sections were stained with hematoxylin and eosin and examined and photographed using a Leitz Orthoplan photomircroscope. Portions of yolk sacs or of embryos were removed for PCR genotyping.

The wild type (+/+) embryos and the null (−/−) embryos developed to the 20–24 somite stage, whereas the null embryo was developmentally delayed. The most common anomalies observed in these embryos were focal hemorrhages (14/43 null embryos), anomalous positioning of the first branchial arch, as well as cardiac and pericardial anomalies. Both developmentally delayed and 20–25 somite stage null embryos were characterized by anomalies of the "turning" process in which the early murine embryo reverses its inverted U-shape to adopt the dorsal curvature (C-shape) typical of the day 10 embryo. While defects of axial rotation were observed in 23/43 null embryos, positional defects were also seen in 12/108 embryos identified as heterozygous (+/−) or wild type (+/+).

When examined histologically, Fv−/− embryos exhibited defective development of cardiac muscle as demonstrated by the delayed or absent trabeculation of the myocardium. Small hemorrhages in the mesenchyme, particularly in the cephalic region were observed. In these embryos, the mesenchyme was often abnormally condensed, and a lack of development of the posterior region was commonly observed. Histologic sections of a wild type visceral yolk sac illustrated the normal appearance of outer endodermal layer, and blood islands contained hematopoietic stem cells within the extraembryonic mesoderm. A similar pattern was seen in yolk sacs isolated from the subset of null embryos that had developed to the 20-24 somite stage. In contrast, vascular channels in yolk sacs from a population (5/11) of null embryos appeared collapsed.

Anomalies of yolk sac organization were also present in a number of null embryos at E9.5. Grossly, the yolk sac circulation was sluggish, and in many null embryos the yolk sac had a granular appearance, rather than the smooth surface typical of control embryos. On histologic analysis, visceral yolk sacs from these embryos were strikingly abnormal. By E9.5, the visceral yolk sac consisted of an outer endodermal layer and inner mesodermal layer with large vascular plexes containing hematopoietic stem cells, the blood islands. In 5/11 yolk sacs from null embryos examined histologically, the visceral endoderm appeared flattened, with few blood islands. The additional six null yolk sacs appeared to have slightly fewer hematopoietic precursors, but vascular plexes were present in the mesoderm.

These results demonstrate that complete deficiency of Fv results in an incomplete block to murine embryonic development, leading to loss of approximately ½ of Fv−/− embryos at E9.5–10.5, with the remaining animals continuing to term. These results also demonstrate that the incomplete embryonic lethal and perinatal hemorrhagic phenotypes were not the result of an unrelated second mutation or clone-specific effect, as these phenotypes were observed in animals derived from 3 independent ES clones, from 2 different established ES cell lines.

These results also demonstrate that the incomplete embryonic lethal and perinatal hemorrhagic phenotypes were not the result of a genomic imprinting mechanism and a potential sex-limited modification, since this was excluded by genotyping for the Y-chromosome-specific sequence SRY. Nor was the pattern of lethality the result of a potential contribution of genetic background differences among mouse strains, since this possibility was excluded by analysis of Fv+/− mice derived from four successive backcrosses to C57BL/6J or backcrosses onto a pure 129SV background (Table 2).

2. Factor V Clotting Activity

Figure 10:
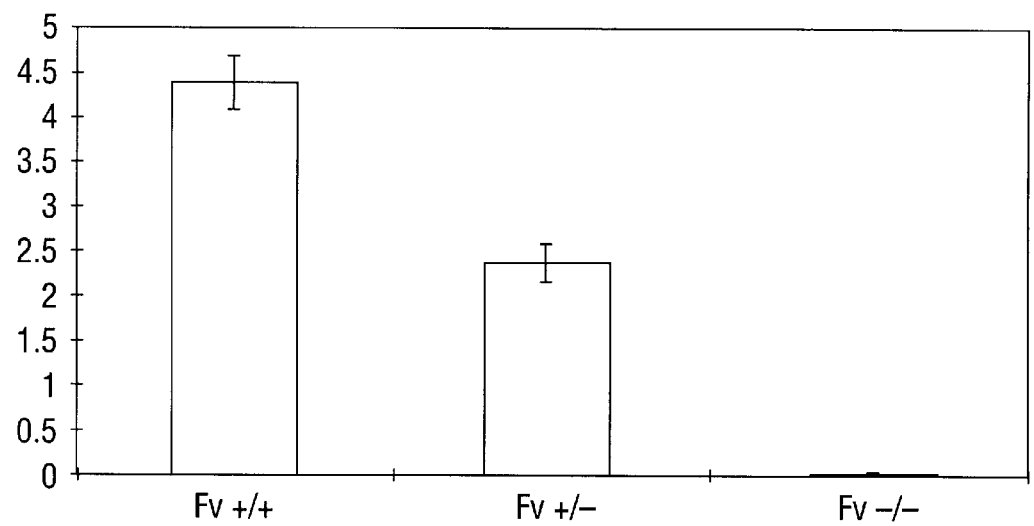
FIG. 10 shows plasma factor V functional activity in Fv+/+, Fv+/−, and Fv−/− mice.

Factor V clotting activity in transgenic mouse plasma was measured and the results are shown in FIG. 10. Whole blood from anesthetized Fv+/+and Fv+/− mice was collected into sodium citrate (0.0129 M final concentration) by cardiac puncture at 6 weeks of age. Fv−/− blood was collected directly from the abdominal cavity of newborn Fv−/− mice. Clotting assays were performed as described above using factor V-deficient human plasma. Units of factor V activity are defined relative to human factor V. The values shown in FIG. 10 are the mean +/− SD of determinations in 5 (Fv+/+ and Fv+/−) or 3 (Fv−/−) animals.

Blood present intra-abdominally was uniformly unclotted and was completely deficient in factor V functional activity. Fv+/− mice appeared entirely normal and exhibited normal hemostasis following tail biopsy. The level of factor V activity measured in this assay was significantly higher in mouse plasma than in human. Plasma from heterozygous (+/−) mice contained approximately half of the factor V clotting activity (2.4 U/ml±0.2) observed in wild-type (+/+) littermates (4.4 U/ml±0.3). No factor V activity was detectable in the factor V null mice (<0.01 U/ml).

Taken together, the results obtained in this Example suggest that thrombin activation, in addition to playing a role in the formation of fibrin blood clot, also has a homeostatic function related to the presumed role of thrombin in platelet activation [Vu et al., Cell 64:1057–1068 (1991); Hanson, et al. Proc. Natl. Acad. Sci. USA 85:3184–3188 (1988)]. Without limiting the invention to any particular mechanism, these data demonstrate that factor V is an essential component of the prothrombinase complex and that FXa has little or no prothrombinase activity in vivo in the absence of factor V, consistent with previous in vitro kinetic studies [Krishnaswamy, et al., J. Biol. Chem. 262:3291–3299 (1987)]. These results also suggest the absence of any significant alternative pathway for the generation of thrombin.

Although generation of thrombin activity may be essential for platelet function in hemostasis, mice with complete absence of platelets, as a result of targeted disruption of the hematopoietic specific transcription factor NFE-2 [Shivdasani et al., Cell 81:695–704 (1995)], also demonstrate less severe bleeding than that observed here. Without limiting the invention to a particular mechanism of action, the profound hemorrhage exhibited in Fv−/− mice likely results from the simultaneous interruption of both platelet activation and fibrin formation.

EXAMPLE 3

Generation Of Fv R504Q Transgenic Mice Using a R504Q Transgene Which Contains A TK/neo Cassette Inserted Into Fv Intron 10

In order to generate Fv R504Q transgenic mice, a targeting vector containing the R504Q mutation in exon 10 of mouse Fv gene (as well as the TK and neo genes flanked by loxP sites) was homologously recombined into the Fv gene in embryonic stem cells. This Example involved (a) construction of a Fv R504Q transgene which contains a TK/neo cassette inserted into Fv intron 10, (b) transfection of ES cells and screening by Southern blotting, and (c) generation of Fv R504Q/TK/neo transgenic mice.

A. Construction Of A Fv R504Q Transgene Which Contains A TK/neo Cassette Inserted Into Fv Intron 10

A schematic representation of the construction of a Fv R504Q transgene is shown in FIG. 11A. An 11.8 kb fragment of Fv genomic sequence (cloned as described in Example 1), from the NcoI site upstream of exon 7 to an artificial NotI site 500 bp into intron 11, was cloned into the pSL301 plasmid vector (Stratagene). A SatI/lXhoI fragment from pFlox [Gu et al., Science 265:103 (1994)] was blunt-end ligated into the SmaI site in intron 10 to generate the Fv R504Q targeting vector. This fragment of pFlox contains an HSV-TK cassette and a neo cassette driven by a PGK promoter, with the whole segment flanked on either side by loxP sites.

B. Transfection Of Embryonic Stem Cells And Screening By Southern Blotting

Figure 12:
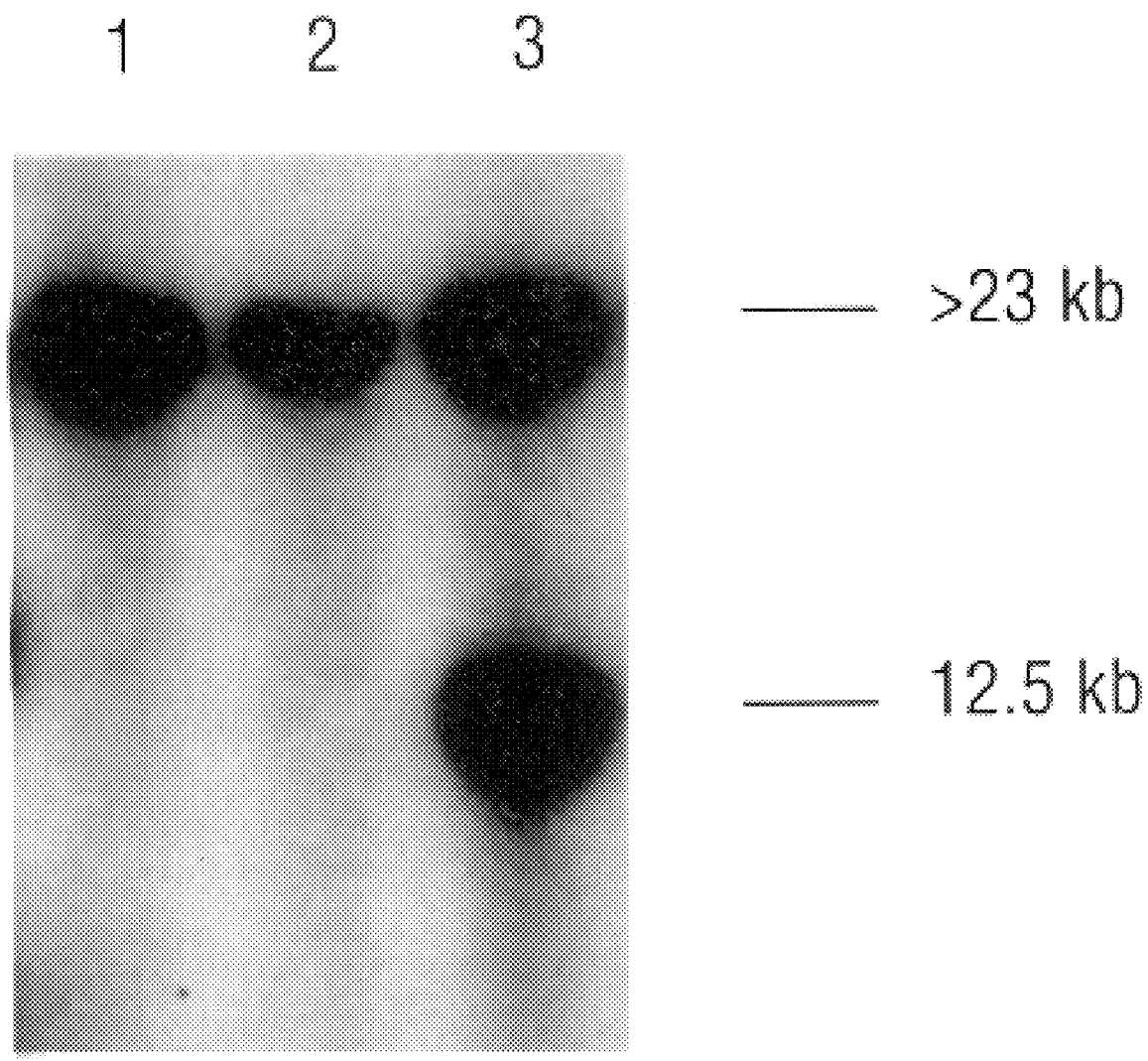
FIG. 12 shows the results of Southern blot analysis of embryonic cells transfected with a R504Q transgene which contains a TK/neo cassette inserted into intron 10 of Fv.

The ES mouse cell lines D3 and CJ7 were transfected and neo-resistant colonies analyzed by Southern blotting as described in Example 2. A high targeting efficiency was again observed, with ~10% of neo resistant colonies demonstrating a Southern blot pattern consistent with successful homologous recombination. The exon 13 Southern blot probe (described in Example 2) detects a >23 kb germline EcoRV fragment. Successful targeting introduces a new EcoRV site within the insert in intron 10, resulting in a 12.5 kb band from the targeted allele (FIG. 11A). The Southern blot in FIG. 12 shows 2 nontargeted ES cell lines (lanes 1 and 2) exhibiting only the germline >23 kb band. The successfully targeted ES cell line in lane 3 contains both the single germline >23 kb allele, along with the targeted 12.5 kb allele.

Since homologous recombination in the left arm is likely to occur upstream of exon 10, the mutant sequence would be expected to be delivered to the target allele along with the intron 10 insertion. However, if the recombination in the left arm occurs between the exon 10 mutation and the intron 10 insertion, the target allele might still carry the normal sequence in exon 10. Therefore, in order to identify the presence of normal or mutant sequence at codon 504 in exon 10, five targeted ES cell lines were screened by PCR using the primers 5'-AGGAGCTCAGTGAGAAC-3' (SEQ ID NO:49) and 5'-GGCAGGCTCAAACTTCACTA-3' (SEQ ID NO:50) at 94° C. for 80 sec., 60° C. for 60 sec., and 72° C. for 2 min. Three of the colonies contained the mutant exon 10 whereas 2 were wild-type. Without limiting the invention to any particular mechanism, this surprisingly high frequency of the wild-type sequence suggests that the junction between the intron 10 insertion and the left arm of genomic DNA may be a particular hot spot for recombination.

C. Generation Of Fv R504Q/TK/neo Transgenic Mice

In order to generate Fv R504Q transgenic mice, each of the three targeted ES lines (described above) carrying the R504Q mutation (as well as the TK and neo genes) were injected into blastocysts as described in Example 2. High level chimeric mice have been obtained. However, to date, germline transmission of this allele to progeny of these chimeric mice has not yet been achieved. Without limiting the present invention to any particular mechanism, failure to achieve germline transmission may be due to the presence of a functional HSV-tk gene. It has been reported that expression of HSV-tk is incompatible with spermatogenesis.

EXAMPLE 4

Generation Of Fv R504Q Transgenic Mice Using Cre-Mediated Homologous Recombination In order to generate Fv R504Q transgenic mice, the TK/neo genes were excised from the homologously recombined ES cell clones containing the R504Q mutation in exon 10 of the mouse Fv gene (described in Example 3). This excision was accomplished by transfecting the ES cells containing the targeting vector with a Cre recombinase-expression plasmid. In the presence of Cre recombinase, DNA located between two loxP sites (i.e., the TK/neo genes) is efficiently excised leaving behind a single loxP site. ES cells containing the R504Q mutation (and a single loxP site) were then used to generate transgenic mice. This Example involved: (a) Excision of the TK/neo inset by Cre-mediated homologous recombination; and (b) Generation and characterization of R504Q transgenic mice.

A. Excision Of The TK/neo Insert By Cre-Mediated Homologous Recombination

Figure 13:
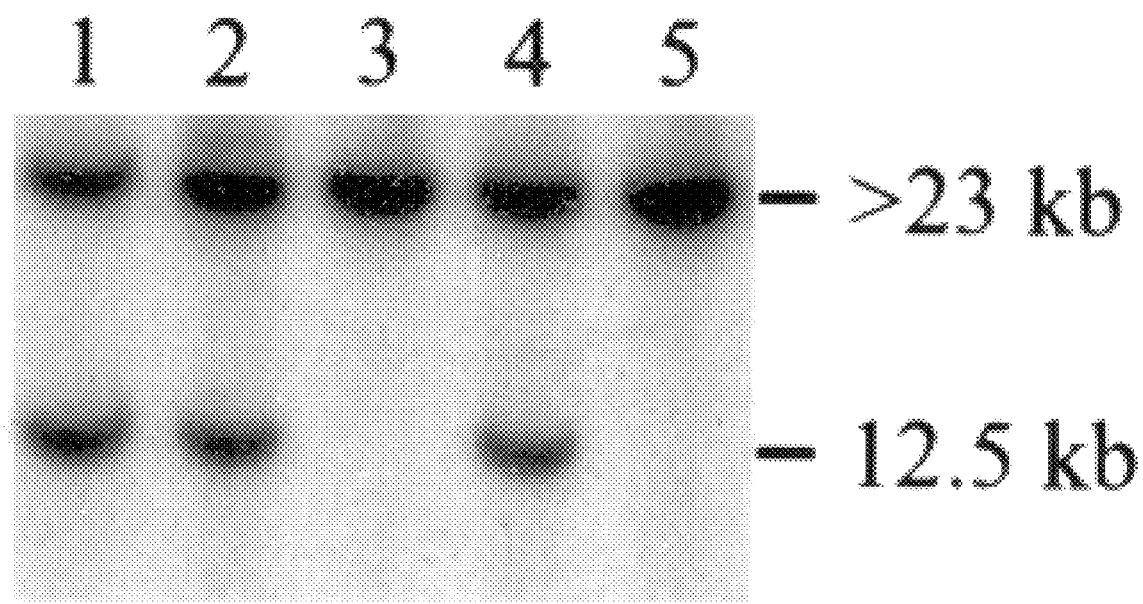
FIG. 13 shows the results of Southern blot analysis of embryonic stem cells carrying TK/neo and the R504Q mutation following transfection with the Cre-expression plasmid, pMC-Cre.

In order to excise the TK/neo insert from the Fv R504Q mutant (described above in Example 3), ES cells carrying the targeted allele and the R504Q mutation were transiently transfected with the Cre-expression plasmid, pMC-Cre [Gu el al., Science 265:103 (1994)]. Transfected cells were then grown without selection and individual colonies were screened by Southern blot analysis. Successful excision of the TK!neo insert by Cre-mediated homologous recombination between the loxP sites is expected to yield the genomic structure depicted in FIG. 11B. In this excised allele, the additional EcoRV site in the insert has been removed and thus Southern blot analysis (as described above) is expected to now reveal a >23 kb allele in place of the 12.5 kb targeted allele. Southern blot analysis of ES colonies screened following transient transfection with the Cre expression plasmid is shown in FIG. 13. Lanes 1–5 contain DNA from individual ES colonies which had been transfected with the Fv R504Q/TK/Ineo transgene and with the pMC-Cre plasmid. Although the 12.5 kb band associated with the intron 10 insertion was still present on 1 allele of the ES colonies in lanes 1, 2 and 4, the colonies in lanes 3 and 5 demonstrate successful excision with the loss of the 12.5 kb band. The excised allele now contains only 143 bp of additional sequence in intron 10 (derived from the loxP site and surrounding polylinker sequences). This small difference in size cannot be distinguished from the wild-type >23 kb allele on the Southern blot. PCR analysis confirmed the retention of the R504Q amino acid substitution on the excised allele. A remarkably high efficiency of Cre-mediated recombination was observed with ~15% of screened colonies demonstrating excision of the loxP flanked segment. This high efficiency obviated the need for negative selection against TK with gancyclovir.

The effect of the small additional sequence (143bp) remaining in intron 10 after Cre excision (FIG. 11B) on Fv gene expression was investigated in order to exclude the possibility of a negative effect of the small remaining loxP intron 10 insertion on RNA processing. An ~5 kb BamHI/NotI genomic fragment containing murine Fv exons 8–11 (FIG. 11A) with and without the loxP insertion was cloned into the exon trapping vector pSPL3 which contains splicing donor and acceptor fragments and carries an Amp$^r$ gene. The single loxP intron 10 insertion was generated by passing the targeting vector plasmid shown in FIG. 11A through a Cre-expressing *E. coli* host to excise the TK/neo cassette. Following transient transfection of the exon trapping vectors into COS-1 cells, total RNA was prepared and RNA PCR performed using primers specific for Fv exons 10 and 11 [5'-CTCTTG TTCTCGTCAAACAC-3' (SEQ ID NO:31) and 5'-TTGCCTCTGGGCTGATAGGG-3' (SEQ ID NO:51) at 94° C. for 80 sec., 60° C. for 60 sec., and 72° C. for 2 min.]. Equal quantities of the appropriately spliced Fv mRNA were obtained from both plasmids, with no evidence for aberrant splicing or inhibition of normal splicing.

These results demonstrate that the additional 143 bp sequence which remained in intron 10 after Cre excision did not have a significant effect on Fv gene expression. The absence of a negative effect on gene expression confirms recent findings by Gu et al. In a recent report, Gu et al. [Gu et al., Science 265:103 (1994)], used the same pFlox sequences which were used in this Example, and inserted these sequences into the DNA polymerase β-gene. Gu et al. observed a normal level of gene expression from a targeted allele carrying inserted loxP sites in 2 adjacent introns, thus excluding a negative effect of additional inserted sequences on gene expression.

B. Generation And Characterization Of R504Q Transgenic Mice

Figure 14:
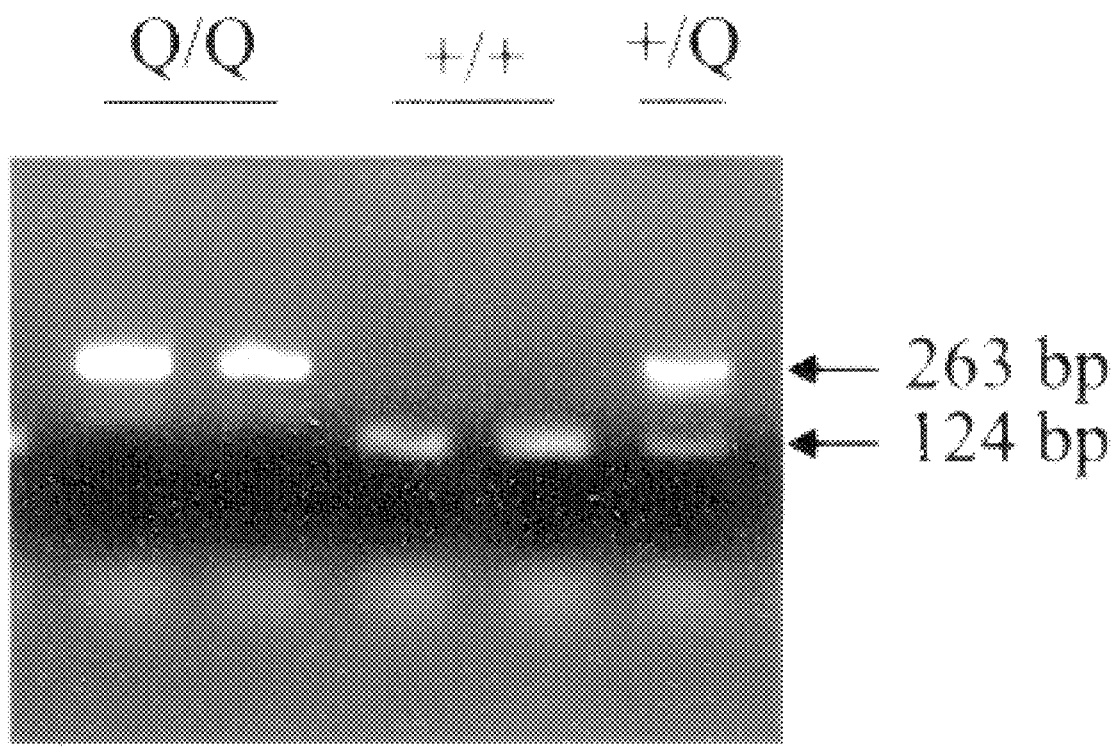
FIG. 14 shows a photograph of an ethidum bromide-stained gel containing DNA from PCR analysis of transgenic mice carrying the R504Q mutation.

ES cells carrying the excised allele were injected into blastocysts of E3.5 blastocysts from C57BL/6J mice as described in Example 2. High level chimeric mice were obtained. In addition, germline transmission of ES cells carrying the R504Q mutation was obtained and stable lines of transgenic mice were established. The genotype of progeny mice was determined by PCR of tail DNA using primers [primer 1: 5'-AGGAGCTCAGTGAGAAC-3' (SEQ ID NO:52) and primer 2: 5'-GGCAGGCTCAAACTTCACTA-3' (SEQ ID NO:53)] that amplify an intron 10 segment containing the loxP site. The results of PCR analysis of progeny transgenic mice are shown in FIG. 14. In FIG. 14 lanes 1 and 2 ("Q/Q") contain PCR products amplified from progeny mice homozygous for the R504Q allele, lanes 3 and 4 (+/+) contain PCR products amplified from wild-type mice and lane 5 (+Q) contains PCR products amplified from progeny mice heterozygous for the R504Q allele. The wild-type allele produces a 124 base pair band whereas the presence of the single remaining loxP site results in a 267 base pair product from the R504Q allele. These results demonstrate the generation of homozygous (R504Q/R504Q) and heterozygous (R504Q/+) transgenic mice.

1. Factor V Clotting Activity

Figure 15:
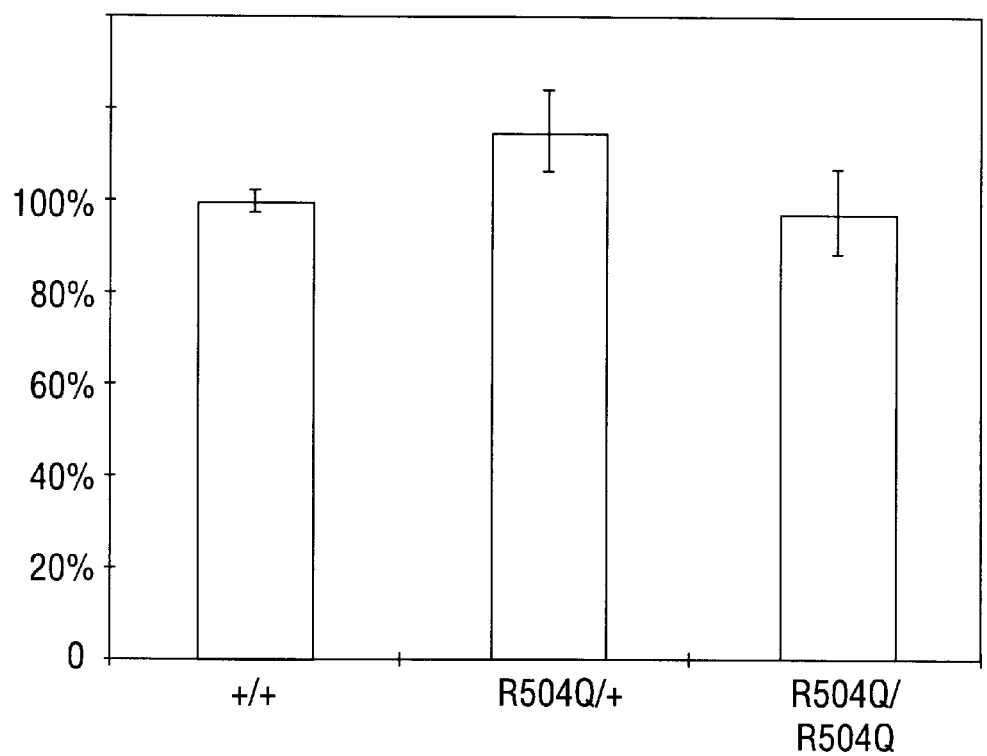
FIG. 15 shows plasma factor V clotting activity in heterozygous (R504Q/+), homozygous (R504Q/R504Q), and control (+/+) mice.
Figure 16A:
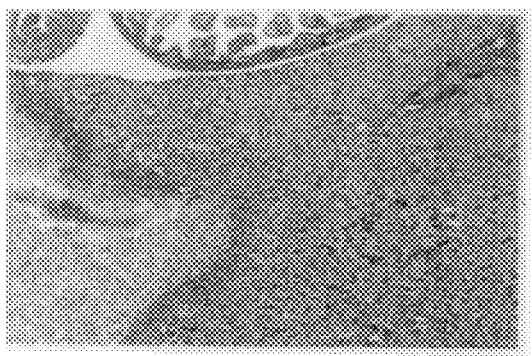
FIGS. 16A–D shows histological sections of liver (16A), mesenteric vessels (16B), atrium (16C) and brain vessels (16D) from a homozygous R504Q/R504Q transgenic pup.
Figure 16B:
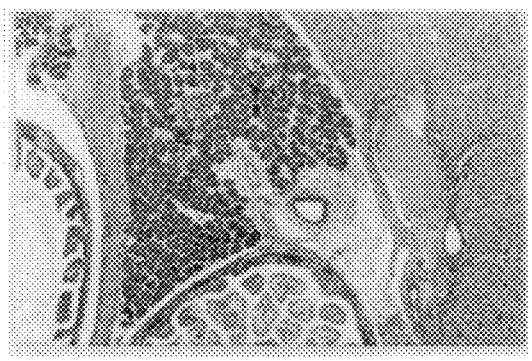
Figure 16C:
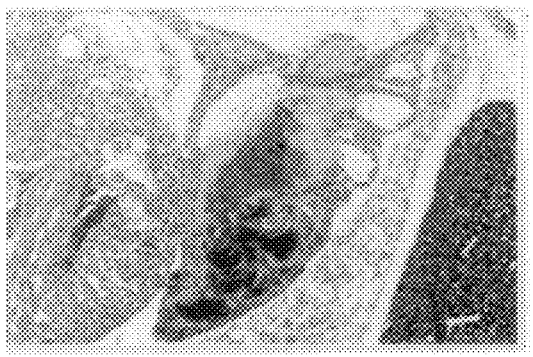
Figure 16D:
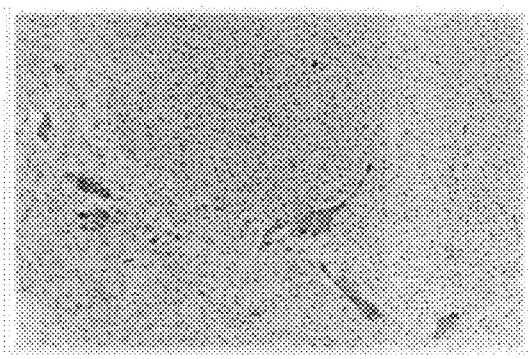

Plasma obtained from Fv (R504Q/+) heterozygous, Fv (R504Q/R504Q) homozygous, and wild-type Fv+/+control mice were analyzed for factor V clotting function as described above in Example 2 and the results are shown in FIG. 15. In FIG. 15 factor V is activity is shown for wild-type (+/+), heterozygotes (R504Q/+) and homozygotes (R504Q/R504Q). These results demonstrate that factor V clotting activity in both the heterozygous (R504Q/+) and homozygous (R504Q/R504Q) mice is indistinguishable from that observed in control (+/+) mice. These results also demonstrate that the targeted Fv R504Q allele maintains the normal pattern of gene regulation and expression and confirms the in vitro expression studies described above in Example 1 in which normal functional activity for the recombinant mutant factor V R504Q protein was demonstrated.

2. APC Resistance Assay

Plasma obtained from Fv R504Q/+ heterozygous, Fv R504Q/R504Q homozygous, and wild-type Fv+/+ control mice were analyzed for APC resistance using a commercial kit for human APC resistance (Chromogenix, Molendal, Sweden). Consistent with the in vitro analysis of recombinant mutant murine factor V shown in FIG. 6, plasma from R504Q/R504Q homozygous mice showed significant APC resistance (ratio=1.37±0.1 compared to wild type ratio of 2.1±0.1) with an intermediate value in heterozygous mice (ratio=1.5±0.1) (FIG. 15). These data are remarkably similar to those observed with plasma from human patients carrying the factor V R506Q mutation.

Taken together, the retention of wild-type factor V clotting activity and of APC resistance in Fv R504Q mice confirms the suitability of the Fv R504Q mouse as an animal model for human factor V R506Q thrombophilia, a common disorder in humans.

3. Gross Morphology And Histology

Morphological examination of genotyped 135 term pups and 112 E18.5 embryos from an intercross between heterozygous (R504Q/+) mice showed that heterozygous (R504Q/+) and homozygous (R504Q/R504Q) mice develop normally to term, but that ⅓ to ½ of the homozygous (R504Q/R504Q) progeny are lost in the immediate postnatal period.

Histologic analysis of R504Q homozygous pups revealed widespread microvascular thrombi as shown in FIGS. 16A–D. FIG. 16 shows histological sections of paraffin embedded tissues derived from transgenic mice prepared using standard methods known in the art. The upper left panel (16A) shows a hepatic venous thrombus with an associated segment of infarction. The lower left panel (16B) shows several fresh venous thrombi in mesenteric vessels adjacent to the pancreas and liver. The upper right panel (16C) shows a large thrombus in the left atrium and the lower right panel (16D) multiple microthrombi in small vessels in the brain. The thrombosis observed in the Fv R504Q/R504Q mice appears to be predominantly venous. Occasional arterial thrombi may represent emboli from the left atrial thrombi which are commonly observed. Although scattered thrombi have been observed in all homozygous pups examined to date, the severity of thrombosis appears to directly correlate with the gross clinical state of the pup at the time of sacrifice. These results suggest that the observed perinatal death in ⅓ to ½ of the homozygote R504Q mice is due to thrombotic complications. Remarkably, homozygous Fv R504Q/R504Q mice surviving this immediate postnatal period appear normal (to date, several animals have survived greater than 4 months) and fertile.

EXAMPLE 5

Generation Of Fv R504Q/R305Q Double Mutant Transgenic Mice

Although the common R506Q APC resistance mutation in human factor V was initially reported to result in complete resistance to APC [Bertina, Nature 369:64 (1994)], recent biochemical studies have demonstrated that the defect is only partial [Kalafatis, J. Biol. Chem. 270:4053 (1995)]; Heeb, Blood 85:3405 (1995)]. While cleavage at Arg 506 is required for optimum exposure of the additional APC cleavage sites at Arg 306 and Arg 679, cleavage at these latter two sites results in complete inactivation of factor Va. The in vitro results reported in Example 1, and the in vivo data shown in Example 4 using recombinant murine Fv are consistent with this model in that murine factor V R504Q (homologous to human R506Q) exhibited delayed inactivation by APC, whereas mutations at both R504 and R305 resulted in a molecule which was highly resistant to APC inactivation.

Therefore, in order to provide an in vivo mouse model having a more completely APC resistant factor V, transgenic mice in which the transgene carries both R504Q and R305Q were generated. An approximately ~9.9 kb ApaLI fragment was excised from the expression plasmids pFV-R305Q:R504Q and pFV-WT (described in Example 1; See, FIG. 1). The ApaLI fragments were injected into C57BL/6J oocytes, and the injected oocytes implanted using techniques well known in the art [Hogan et al., supra].

Tail DNAs were prepared from progeny mice and transgene positive animals identified by screening PCR using primer 5'-CTTCTCTCCTTACGAAGATG-3' (SEQ ID NO:29), and primer 5'-CTCTTGTTCTCGTCAAACAC-3' (SEQ ID NO:31). Southern blot analysis was performed using a murine Fv exon 13 probe B (described above in Example 2) (FIG. 2A) to confirm the presence of the transgene, and allow quantification of copy number.

Using Southern blot analysis, a total of 8 transgenic founders carrying the double mutant APC resistant factor V (FV-R305Q:R504Q) have been identified with copy numbers ranging from 1–38. In addition, eight transgenic founders carrying the control wild-type Fv transgene have been identified with copy numbers ranging from 1–32. The Fv transgenic founder mice are crossed with heterozygous knockout mice [Fv+/−] (described in Example 2) to generate transgene positive (Tg+) Fv−/− progeny.

EXAMPLE 6

Plasma And Platelet Pools Of Factor V In The Mouse

In order to determine the relative localization of factor V activity in the plasma and platelet compartments of mouse blood, the levels of factor V in normal mouse plasma and platelets were measured using the factor V functional clotting assay described above (See, Examples 1 and 2). Washed platelet lysates and platelet-poor plasma were prepared using standard methods [Tracy et al., Blood 60:59 (1982)]. factor V activity in platelet poor murine plasma was approximately 4 times that of humans (similar to the higher levels of factor V observed in bovine plasma [Tracy et al., supra (1982)]. The factor V activity observed in highly washed murine platelet lysates was similar to the level of activity observed in platelet poor plasma. Based on these measurements, it is estimated that approximately 48% of the total blood factor V activity in the mouse is localized to the platelet compartment with the remaining 52% in the plasma compartment. This contrasts with the measurements of Tracy et al. [Tracy et al., supra (1982)] in humans where the platelet pool of factor V was estimated to contribute 18–25% of the factor V in whole blood. Tracy et al. also noted a much smaller relative platelet factor V pool in the bovine system, constituting 2–5% of whole blood factor V.

Since the normal murine platelet count is approximately 5-fold higher than that of humans, these data suggest that the relative amount of factor V activity per platelet when compared to plasma, is quite similar for mouse and humans. These results are also consistent with the identification of Fv mRNA in murine bone marrow by cDNA cloning (See, Example 1), which is presumed to represent primary biosynthesis of factor V in the megakaryocyte. The similarity of the relative distribution of factor V activity in mouse and human plasma and platelets further demonstrates the suitability of the transgenic mice provided herein as a model for human factor V-related abnormalities.

EXAMPLE 7

Expression Of Recombinant Fragments Of Murine Fv in *E. coli*

In order to prepare murine-specific protein fragments as immunogens, three separate fragments of the murine Fv cDNA coding sequence were expressed in an *E. coli* expression system. A 2069 base pair cDNA fragment encoding amino acids −26 to 662 (FIG. 2), including most of the A1 and A2 repeats (FIG. 3), was cloned into the polylinker of the vector pGEX (Pharmacia) for the expression of a GST fusion protein. Similarly, GST fusion expression constructs were assembled containing the B domain (a 1502 bp fragment encoding amino acids 1002–1501) and a 1251 bp fragment encoding amino acids 1507–2155 (the A3 and C domains) (FIGS. 2 and 3). All three murine factor V fragments were expressed as GST fusions and the resulting fusion proteins were purified on glutathione-Sepharose resins (Pharmacia) following the manufacturer instructions. High yields of the A1–A2 fragment and the A3-C1-C2 fragment were obtained. In contrast, no expression of the B domain fusion was obtained (i.e., no protein of the expected size was observed on PAGE gels).

Factor V fusion proteins containing thioredoxin may be generated using the pTRXFUS and hpTRXFUS vectors (Invitrogen and Genetics Institute, Cambridge, Mass.). The presence of thioredoxin on fusion proteins has been reported to increase the solubility of the fusion protein. Thioredoxin-containing fusion proteins are generated and purified using methods well known to the art [*Current Protocols in Molecular Biology*, Ausubel et al. (eds), John Wiley & Sons, Inc., pp. 16.8.1–16.8.14].

EXAMPLE 8

Production Of Anti-Murine Factor V Antibodies

Murine factor V substantially purified using polyacrylamide gel electrophoresis (PAGE) (Sambrook, supra) is used to immunize suitable animals (e.g., rabbits, hamsters, rats, goats, sheep, etc.) and to produce antibodies using standard protocols [alternatively, recombinant factor V fusion proteins may be purified by affinity (e.g., glutathione-Sepharose) or metal chelation chromatography and used to immunize animals]. The amino acid sequence translated from factor V is analyzed using DNAStar software (DNAStar, Inc.) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel FM et al. (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with maleimidobenzoyl-N-hydroxysuccinimide ester (MBS; Ausubel FM et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

Purified factor V (native or fusion proteins) may be used to generate antibodies which react specifically with the factor V protein. The production of both polyclonal and monoclonal antibodies utilize techniques standard to the art. Polyclonal antibodies contain a mixture of different types of antibodies that are specific for many different antigens present on the immunogen. Monoclonal antibodies contain a single species of antibody having a defined specificity.

Briefly, polyclonal antibodies are generated by immunization of a host animal with a purified protein. The serum of the immunized animal will contain antibodies directed against one or more epitopes of the injected protein. When rabbits are used for the production of polyclonal antibodies specific for factor V, 50 to 1000 μg of purified factor V is mixed with complete Freund's or another suitable adjuvant and administered subcutaneously (s.c.) to the rabbit. Typically, multiple s.c. injections, each containing a maximum volume of about 400 μl are administered (up to approximately 10 injections may be performed per animal). Alternatively, the immunogen may administered by intramuscular or intradermal injection. Four to six weeks following the initial or primary injection, secondary or booster injections are administered (these may utilize incomplete Freund's or another suitable adjuvant). Additional boosts are given in 4–6 week intervals following the last injection. Immunized rabbits are bled (e.g., using the marginal ear vein) and the serum is screened for the presence of antibodies which react specifically with factor V (e.g., by ELISA screening). Polyclonal antibodies can be produced using purified recombinant mouse FV proteins by a variety of companies (e.g., Rockland, Inc., Gilbertsville, Pa.).

Monoclonal antibodies are produced by immunizing a host animal with purified factor V protein (native or fusion). Once the host has produced antibodies specific for factor V protein, the spleen of the host is removed. The plasma cells present in the spleen of the immune host are then fused with a myeloma cell (the "fusion partner") to produce hybridoma cells. When rats are immunized for the production of plasma cells to be used to generate hybridomas, suitable fusion partners include the YB2/0 and IR983F cell lines [*Antibodies: A Laboratory Manual*, Harlow and Lane, Eds. (1988) Cold Spring Harbor Laboratory Press, Cold Spring Harbor, N.Y.]. Rats are immunized as described above. Following the generation of specific anti-factor V antibodies in the animals (typically following 2 to 3 booster injection and about 56 days following the initial injection), spleens are removed and splenocytes are fused (e.g., using polyethylene glycol) with the desired fusion partner. The fused cells are diluted in the appropriate selective medium and plated in multiwell culture plates. Each hybridoma cell produces a single type of antibody. Culture supernatant from individual hybridoma cells (removed from the hybridomas about 1 week following plating) is screened using standard techniques to identify those hybridoma cells expressing monoclonal antibodies reactive with factor V (see Harlow and Lane, supra for a review of screening techniques).

When a fusion protein is utilized for the production of antibodies, the resulting antibodies may contain antibodies directed against the fusion partner (e.g., GST). These anti-fusion partner antibodies may be removed from polyclonal sera by chromatography of the sera on a column containing the fusion partner immobilized to a solid support such as Sepharose beads (Pharmacia). For example, to remove anti-GST antibodies from polyclonal sera raised against a GST fusion protein, the sera are chromatographed on a resin comprising the GST protein covalently linked to glutathione Sepharose. Anti-fusion partner antibodies may be excluded during the routine screening of hybridomas during the production of monoclonal antibodies.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology and related fields are intended to be within the scope of the following claims.

We claim:

1. A transgenic mouse expressing an activated protein C (APC) resistant factor V, wherein the genome of said transgenic mouse contains a non-naturally occurring point mutation which results in an amino acid substitution within exon 10 of the factor V gene, and wherein said transgenic mouse expresses said exon 10 of said factor V gene, wherein said amino acid substitution causes said mouse to display spontaneous thrombosis.

2. The transgenic mouse of claim 1, wherein said genome further comprises a loxP site within the factor V gene.

3. The transgenic mouse of claim 1, wherein said APC resistant factor V is factor V-R504Q.

4. The transgenic mouse of claim 1, wherein said APC resistant factor V is factor V-R305Q:R504Q.

5. The transgenic mouse of claim 1, wherein said transgenic mouse does not express wild-type factor V.

6. A transgenic mouse that does not, in express functional wild-type factor V, wherein said transgenic mouse displays spontaneous hemophilia, the genome of said transgenic mouse contains a deletion of one or more exons of the factor V gene.

7. The transgenic mouse of claim 6, wherein said genome further comprises a frameshift mutation within said factor V gene.

8. The transgenic mouse of claim 6, wherein said genome further comprises a heterologous selectable marker gene.

9. A method for screening compounds for anticoagulant activity, comprising:
   a) providing:
      i) a transgenic mouse expressing an APC resistant factor V, wherein the genome of said transgenic mouse contains a non-naturally occurring point mutation which results in an amino acid substitution within exon 10 of the factor V gene, and wherein said transgenic mouse expresses said exon 10 of said factor V gene, wherein said amino acid substitution causes said mouse to display spontaneous thrombosis;
      ii) a composition comprising a test compound in a form suitable for administration such that said compound is bioavailable in the blood of said mouse;
   b) administering said test compound to said transgenic mouse; and
   c) measuring a reduction in the incidence of microvascular thrombi and thereby identifying a compound as therapeutic.

10. The method of claim 9, wherein said test compound is selected from the group consisting of heparin, oral anticoagulants, antithrombotics, and thrombolytics.

11. The method of claim 9, wherein said transgenic mouse expressing an APC resistant factor V is a pregnant female containing at least one fetus in uterus of said pregnant female, and said test compound is administered under conditions such that said test compound is administered to said fetus of said pregnant female in utero.

12. The method of claim 11, further comprising permitting said fetus to progress to term and to be delivered.

13. The method of claim 12, further comprising measuring an increased rate of postnatal survival of said delivered animal.

14. A method for producing a transgenic mouse predisposed to spontaneous thrombosis, said method comprising:
   a) providing a DNA sequence comprising:
      i) at least a portion of a non-human factor V gene, said portion comprising one or more point mutations within exon 10 of said factor V gene, said point mutations resulting in the production of an APC resistant factor V protein; and
      ii) a positive selectable marker gene, said marker gene flanked by loxP sites;
   b) introducing said DNA sequence into an embryonic stem cell of a mouse under conditions such that said DNA sequence is homologously recombined into at least one of the naturally occurring factor V genes in the genome of said embryonic stem cell to produce a homologously recombined embryonic stem cell containing at least one factor V allele containing said one or more point mutations and said selectable marker gene;
   c) injecting said homologously recombined embryonic stem cell into the blastocyst of a mouse;
   d) introducing said injected blastocyst into a pseudo-pregnant female mouse; and
   e) permitting said pseudo-pregnant female mouse to deliver one or more transgenic mice containing said homologously recombined DNA sequence, wherein said one or more transgenic mice express said at least one factor V allele containing said one or more point mutations, and is characterized by being predisposed to spontaneous thrombosis.

15. The method of claim 14, further comprising prior to step c), introducing a source of Cre recombinase into said embryonic stem cell containing at least one factor V allele containing said one or more point mutations and said selectable marker gene under conditions such that said selectable marker gene is excised to produce an embryonic stem cell containing at least one factor V allele containing said one or more point mutations and lacking said selectable marker gene.

16. The method of claim 14, wherein said DNA sequence comprises the R504Q mutation.

17. The method of claim 14, wherein said DNA sequence comprises the R305Q and R504Q mutations.

18. The method of claim 14, wherein said one or more transgenic mice are further characterized by displaying spontaneous thrombosis.

19. A method for producing a transgenic mouse expressing an APC resistant factor V and displaying spontaneous thrombosis, comprising:
   a) providing:
      i) a female transgenic mouse expressing an APC resistant factor V, wherein the genome of said female trarisgenic mouse contains a non-naturally occurring point mutation which results in an amino acid substituion within exon 10 of the factor V gene, and wherein said female transgenic mouse expresses said exon of said factor V gene and does not display spontaneous thrombosis; and
      ii) a male transgenic mouse expressing an APC-resistant factor V, wherein the genome of said male transgenic mouse contains a non-naturally occurring point mutation which results in an amino acid substitution within exon 10 of the factor V gene, and wherein said male transgenic mouse expresses said exon of said factor V gene and does not display spontaneous thrombosis; and
   b) mating said female transgenic mouse with said male transgenic mouse to produce progeny comprising at least one transgenic offspring expressing an APC resistant factor V, wherein the genome of said at least one transgenic offspring contains said non-naturally occurring point mutation within said exon of said factor V gene, and wherein said at least one transgenic offspring expresses said exon of said factor V gene and displays spontaneous thrombosis.

20. A method for producing a transgenic mouse that does not express functional wild-type factor V and displaying spontaneous hemophilia, comprising:
   a) providing:
      i) a female transgenic mouse that does not express functional wild-type factor V, wherein the genome of said female transgenic mouse contains a deletion of one or more exons of the factor V gene, and wherein said female transgenic mouse does not display spontaneous hemophilia; and
      ii) a male transgenic mouse that does not express functional wild-type factor V, wherein the genome of said male transgenic mouse contains a deletion of one or more exons of the factor V gene, and wherein said male transgenic mouse does not display spontaneous hemophilia; and
   b) mating said female transgenic mouse with said male transgenic mouse to produce progeny comprising at least one transgenic offspring that does not express wild-type factor V, wherein the genome of said at least one transgenic offspring contains said deletion of one or more exons of said factor V gene, and wherein said at least one transgenic offspring displays spontaneous hemophilia.

* * * * *